(12) United States Patent
Stoessel et al.

(10) Patent No.: US 10,205,106 B2
(45) Date of Patent: Feb. 12, 2019

(54) POLYCYCLIC COMPOUNDS

(71) Applicant: Merck Patent GmbH, Darmstadt (DE)

(72) Inventors: Philipp Stoessel, Frankfurt am Main (DE); Dominik Joosten, Frankfurt am Main (DE); Nils Koenen, Darmstadt (DE)

(73) Assignee: Merck Patent GmbH (DE)

( * ) Notice: Subject to any disclaimer, the term of this patent is extended or adjusted under 35 U.S.C. 154(b) by 57 days.

(21) Appl. No.: 14/902,093

(22) PCT Filed: Jun. 6, 2014

(86) PCT No.: PCT/EP2014/001556
§ 371 (c)(1),
(2) Date: Dec. 30, 2015

(87) PCT Pub. No.: WO2015/000546
PCT Pub. Date: Jan. 8, 2015

(65) Prior Publication Data
US 2016/0204358 A1     Jul. 14, 2016

(30) Foreign Application Priority Data

Jul. 2, 2013   (WO) ............... PCT/EP2013/001926
Jul. 18, 2013  (EP) .................................. 13003625

(51) Int. Cl.
| | | |
|---|---|---|
| H01L 51/00 | (2006.01) | |
| C07D 221/22 | (2006.01) | |
| C07D 401/04 | (2006.01) | |
| C07D 471/08 | (2006.01) | |
| C07D 495/08 | (2006.01) | |
| C09K 11/02 | (2006.01) | |
| C07D 405/04 | (2006.01) | |
| C07D 491/08 | (2006.01) | |
| C07D 413/04 | (2006.01) | |
| C07D 471/04 | (2006.01) | |
| C07D 491/18 | (2006.01) | |
| C07D 495/04 | (2006.01) | |
| H01L 51/50 | (2006.01) | |

(52) U.S. Cl.
CPC ........ *H01L 51/0072* (2013.01); *C07D 221/22* (2013.01); *C07D 401/04* (2013.01); *C07D 405/04* (2013.01); *C07D 413/04* (2013.01); *C07D 471/04* (2013.01); *C07D 471/08* (2013.01); *C07D 491/08* (2013.01); *C07D 491/18* (2013.01); *C07D 495/04* (2013.01); *C07D 495/08* (2013.01); *C09K 11/025* (2013.01); *H01L 51/0052* (2013.01); *H01L 51/0058* (2013.01); *H01L 51/0067* (2013.01); *H01L 51/0071* (2013.01); *H01L 51/0073* (2013.01); *H01L 51/5012* (2013.01); *H01L 51/5056* (2013.01); *H01L 51/5096* (2013.01)

(58) Field of Classification Search
None
See application file for complete search history.

(56) References Cited

U.S. PATENT DOCUMENTS 8,679,645 B2    3/2014   Heil et al.

FOREIGN PATENT DOCUMENTS

| WO | 2006131192 A1 | 12/2006 | |
|---|---|---|---|
| WO | WO 2013123081 A2 * | 8/2013 | ........... C07D 221/16 |
| WO | WO-2014/023377 A2 | 2/2014 | |

OTHER PUBLICATIONS

Bosco et al., "Rational Design of Small Molecule Inhibitors Targeting the Rac GTPase-p67$^{phase}$ Signaling Axis in Inflammation", Chemistry & Biology, 2012, vol. 19, pp. 228-242.
Smith, et al., "Lewis Acid Catalyzed Three-Component Hetero-Diels-Alder (Povarov) Reaction of N-Arylimines with Strained Norbornene-Derived Dienophiles", J.Org. Chem., 2009, vol. 75, pp. 702-715.
International Search Report for International Application No. PCT/EP2014/001556; Application filing date: Jun. 6, 2014.

* cited by examiner

Primary Examiner — Katie L. Hammer
(74) Attorney, Agent, or Firm — Kim Winston LLP

(57) ABSTRACT

The present invention relates to compounds having polycyclic structural units and to electronic devices, in particular organic electroluminescent devices, containing said compounds.

16 Claims, No Drawings

POLYCYCLIC COMPOUNDS

RELATED APPLICATIONS

This application is a national stage entry, filed pursuant to 35 U.S.C. § 371, of PCT/EP2014/001556, filed Jun. 6, 2014, which claims the benefit of European Patent Application No. 13003625.4, filed Jul. 18, 2013, and PCT/EP2013/001926, filed Jul. 2, 2013, both of which are incorporated herein by reference in their entirety.

The present invention relates to compounds suitable for use in electronic devices. The present invention further relates to processes for preparation thereof and to electronic devices.

Electronic devices containing organic, organometallic and/or polymeric semiconductors are becoming increasingly important, and are being used in many commercial products for reasons of cost and because of their performance. Examples here include organic-based charge transport materials (for example triarylamine-based hole transporters) in photocopiers, organic or polymeric light-emitting diodes (OLEDs or PLEDs) and in readout and display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may have great future significance.

Many of these electronic devices, irrespective of the respective end use, have the following general substrate structure which can be adjusted for the particular application:
(1) substrate,
(2) electrode, frequently metallic or inorganic, but also composed of organic or polymeric conductive materials,
(3) charge injection layer(s) or interlayer(s), for example to compensate for unevenness in the electrode ("planarization layer"), frequently composed of a conductive doped polymer,
(4) organic semiconductor,
(5) possibly further charge transport, charge injection or charge blocker layers,
(6) counterelectrode, materials as specified in (2),
(7) encapsulation.

The above arrangement is the general structure of an organic electronic device, it being possible to combine various layers, such that the result in the simplest case is an arrangement composed of two electrodes with an organic layer in between. In this case, the organic layer fulfills all functions including the emission of light in the case of OLEDs. A system of this kind is described, for example, in WO 90/13148 A1, based on poly(p-phenylenes).

Known electronic devices have a useful profile of properties. However, there is a constant need to improve the properties of these devices.

These properties especially include the lifetime of electronic devices. A further particular problem is the energy efficiency with which an electronic device achieves the specified object. In the case of organic light-emitting diodes, which may be based-either on low molecular weight compounds or on polymeric materials, the light yield in particular should be sufficiently high that a minimum amount of electrical power has to be applied to achieve a particular luminous flux. In addition, a minimum voltage should also be necessary to achieve a defined luminance.

It is therefore an object of the present invention to provide novel compounds which lead to electronic devices having improved properties. It is a particular object to provide hole injection materials, hole transport materials, hole blocker materials, electron injection materials, electron blocker materials and/or emitter materials which exhibit improved properties in relation to efficiency, operating voltage, lifetime, color coordinates and/or color purity, i.e. breadth of the emission band. Moreover, the compounds should be processible in a very simple manner, and especially exhibit good solubility and film formation.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, these objects and others which are not specified explicitly but can be inferred or discerned directly from the connections discussed herein by way of introduction are achieved by compounds having all the features of claim 1. Appropriate modifications to the compounds of the invention are protected in the dependent claims that refer back to claim 1.

The invention thus provides a compound comprising at least one structure of the formulae (I) and/or (II)

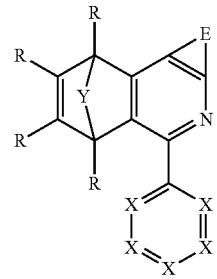

Formula (I)

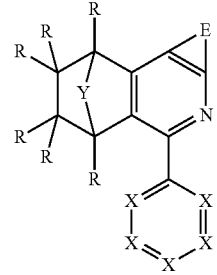

Formula (II)

where the symbols used are as follows:

X is the same or different at each instance and is CR or N;

E is a bivalent bridge, where the E group together with the carbon atoms bonded thereto forms a five- or six-membered ring;

Y is a bivalent bridge selected from O, S, $C(R)_2$, $C(R)=C(R)$, $N(R)$, $B(R)$, $Si(R)_2$, $C=O$, $C=NR$, $C=C(R)_2$, $S=O$, $SO_2$, $C(R)_2—C(R)_2$, $P(R)$ and $P(=O)R$;

R is the same or different at each instance and is H, D, F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, each of which may be substituted by one or more R¹ radicals, where one or more nonadjacent CH₂ groups may be replaced by R¹C═CR¹, C≡C, Si(R¹)₂, C═O, NR¹, O, S or CONR¹ and where one or more hydrogen atoms may be replaced by D, F, Cl, Br, I or CN, or an aromatic or heteroaromatic ring system which has 5 to 60 aromatic ring atoms and may be substituted in each case by one or more R¹ radicals, or an aryloxy or heteroaryloxy group which has 5 to 40 aromatic ring atoms and may be substituted by one or more R¹ radicals, or an aralkyl or heteroaralkyl group which has 5 to 40 aromatic ring atoms and may be substituted by one or more R¹ radicals, or a diarylamino group, diheteroarylamino group or arylheteroarylamino group which has 10 to 40 aromatic ring atoms and may be substituted by one or more R¹ radicals; at the same time, two adjacent R radicals together may form a mono- or polycyclic, aliphatic, aromatic or heteroaromatic ring system;

R¹ is the same or different at each instance and is H, D, F, Cl, Br, I, N(R²)₂, CN, NO₂, Si(R²)₃, B(OR²)₂, C(═O)R², P(═O)(R²)₂, S(═O)R², S(═O)₂R², OSO₂R², a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, each of which may be substituted by one or more R² radicals, where one or more nonadjacent CH₂ groups may be replaced by R²C═CR², C≡C, Si(R²)₂, C═O, NR², O, S or CONR² and where one or more hydrogen atoms may be replaced by D, F, Cl, Br, I, CN or NO₂, or an aromatic or heteroaromatic ring system which has 5 to 60 aromatic ring atoms and may be substituted in each case by one or more R² radicals, or an aryloxy or heteroaryloxy group which has 5 to 40 aromatic ring atoms and may be substituted by one or more R² radicals, or an aralkyl or heteroaralkyl group which has 5 to 40 aromatic ring atoms and may be substituted by one or more R² radicals, or a diarylamino group, diheteroarylamino group or arylheteroarylamino group which has 10 to 40 aromatic ring atoms and may be substituted by one or more R² radicals; at the same time, two or more adjacent R¹ radicals together, or R¹ together with R, may form a mono- or polycyclic, aliphatic, aromatic or heteroaromatic ring system;

R² is the same or different at each instance and is H, D, F or an aliphatic, aromatic and/or heteroaromatic hydrocarbyl radical having 1 to 20 carbon atoms, in which one or more hydrogen atoms may also be replaced by F; at the same time, two or more R² substituents together may also form a mono- or polycyclic aliphatic ring system.

In this context, "adjacent carbon atoms" or adjacent "CH₂ groups" means that the carbon atoms are bonded directly to one another.

The wording that two or more radicals together may form a ring, in the context of the present application, shall be understood to mean, inter alia, that the two radicals are joined to one another by a chemical bond. This is illustrated by the following scheme:

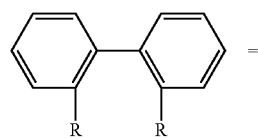

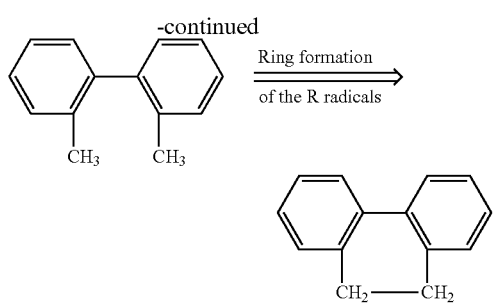

In addition, however, the abovementioned wording shall also be understood to mean that, if one of the two radicals is hydrogen, the second radical binds to the position to which the hydrogen atom was bonded, forming a ring. This shall be illustrated by the following scheme:

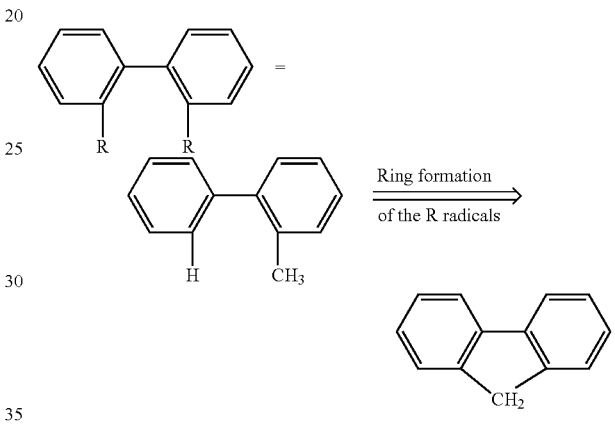

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms in the ring system. A heteroaromatic ring system in the context of this invention contains 1 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9'-diarylfluorene, triarylamine, diaryl ethers, stilbene, etc. are also to be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl or terphenyl, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may also be replaced by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl- and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-60 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-Indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds comprising structures of the formulae (I) and/or (II), characterized in that E is selected from groups of the formula X=X—X=X, X—W—X, W—X=X, X=X—W, in which W is selected from O, S, $C(R)_2$, N(R), B(R), $Si(R)_2$, C=O, S=O, $SO_2$, P(R) and P(=O)R, where X and R are the same or different at each instance and are as defined above. Preferably, W is selected from O, S and N(R). More preferably, E together with the carbon atoms bonded thereto forms an aromatic or heteroaromatic ring having five or six members.

Preference is further given to compounds are those comprising at least one structure of the formulae (Ia) and/or (IIa)

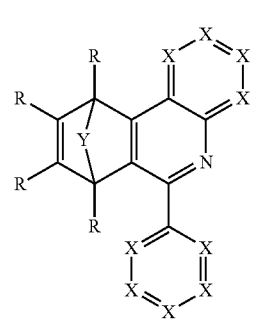

Formula (Ia)

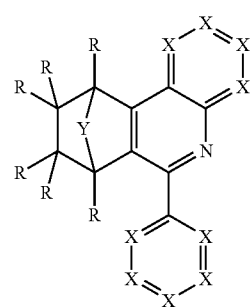

Formula (IIa)

where the symbols used have the definitions given above.

Particular preference is given to compounds comprising at least one structure of the formulae (Ia1), (Ia2), (IIa1) and/or (IIa2)

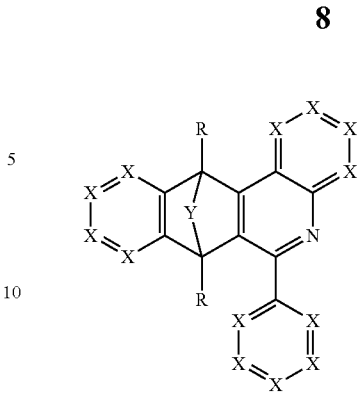

Formula (Ia1)

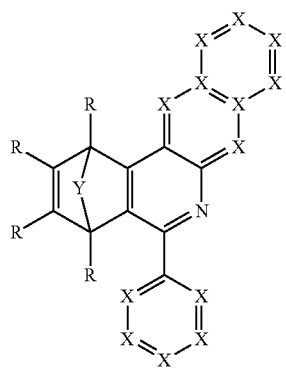

Formula (IIa1)

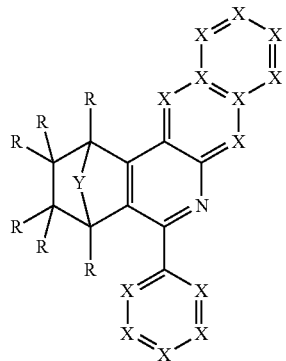

Formula (Ia2)

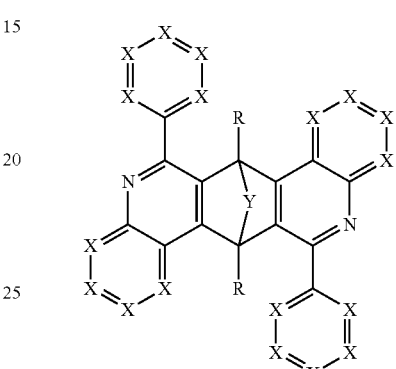

Formula (Ia3)

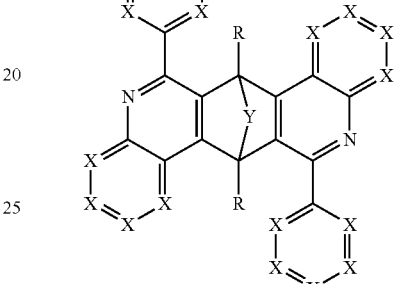

Formula (Ia4)

where the symbols used have the definitions given above.

According to a further configuration of the present invention, preferred compounds are those comprising at least one structure of the formulae (Ib) and/or (IIb)

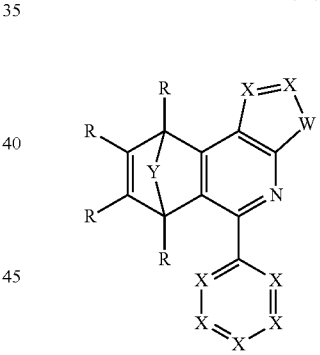

Formula (Ib)

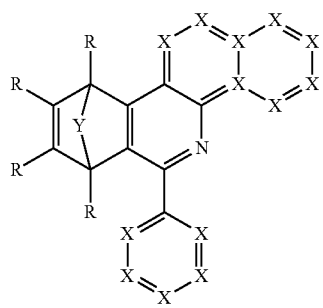

Formula (IIa2)

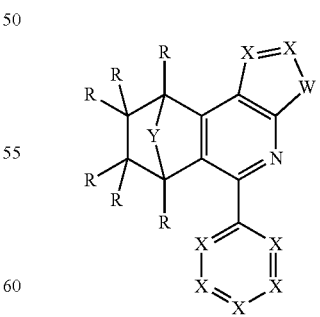

Formula (IIb)

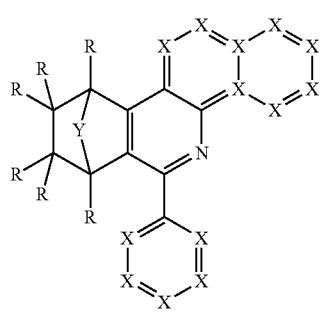

where the symbols used have the definitions given above.

Further preferred are compound having at least one structure of the formulae (Ia3) and/or (Ia4)

where the symbols used have the definitions given above.

According to yet a further configuration of the present invention, very preferred compounds are those comprising at least one structure of the formulae (Ib-1) and/or (IIb-1)

Formula (Ib-1)

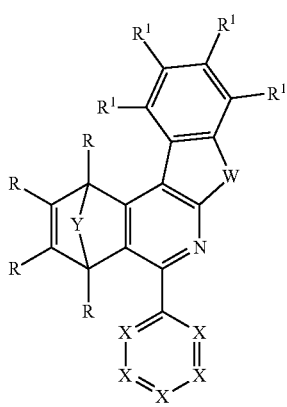

Formula (IIb-1)

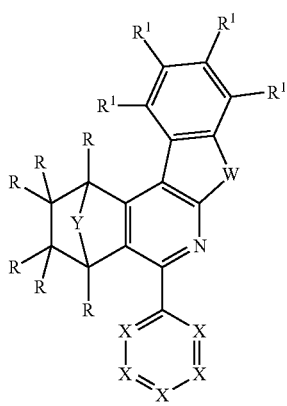

where the symbols used have the definitions given above.

Further preferred compounds are those comprising structures of the formula (Ic)

Formula (Ic)

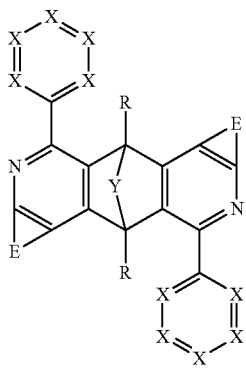

where the symbols used have the definitions given above and E may be the same or different at each instance.

It may further be the case that the compounds have at least two bicyclic groups which are formed by a structural element comprising a Y group, where Y may be the same or different at each instance and is as defined above.

Preferably, the compound may have structures of the formula CyE-(CyF)$_n$ where the symbols and indices are as follows:

n is 2 or 3

CyE is a structural element selected from the formulae

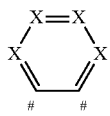 (CyE-1)

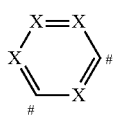 (CyE-2)

 (CyE-3)

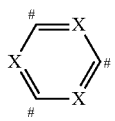 (CyE-4)

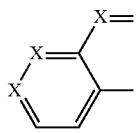 (CyE-5)

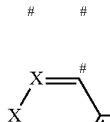 (CyE-6)

 (CyE-7)

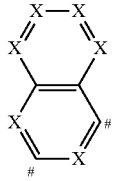 (CyE-8)

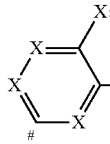 (CyE-9)

 (CyE-10)

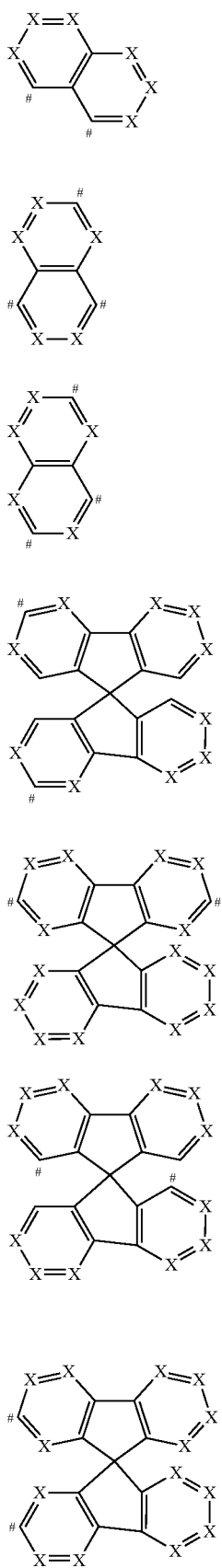
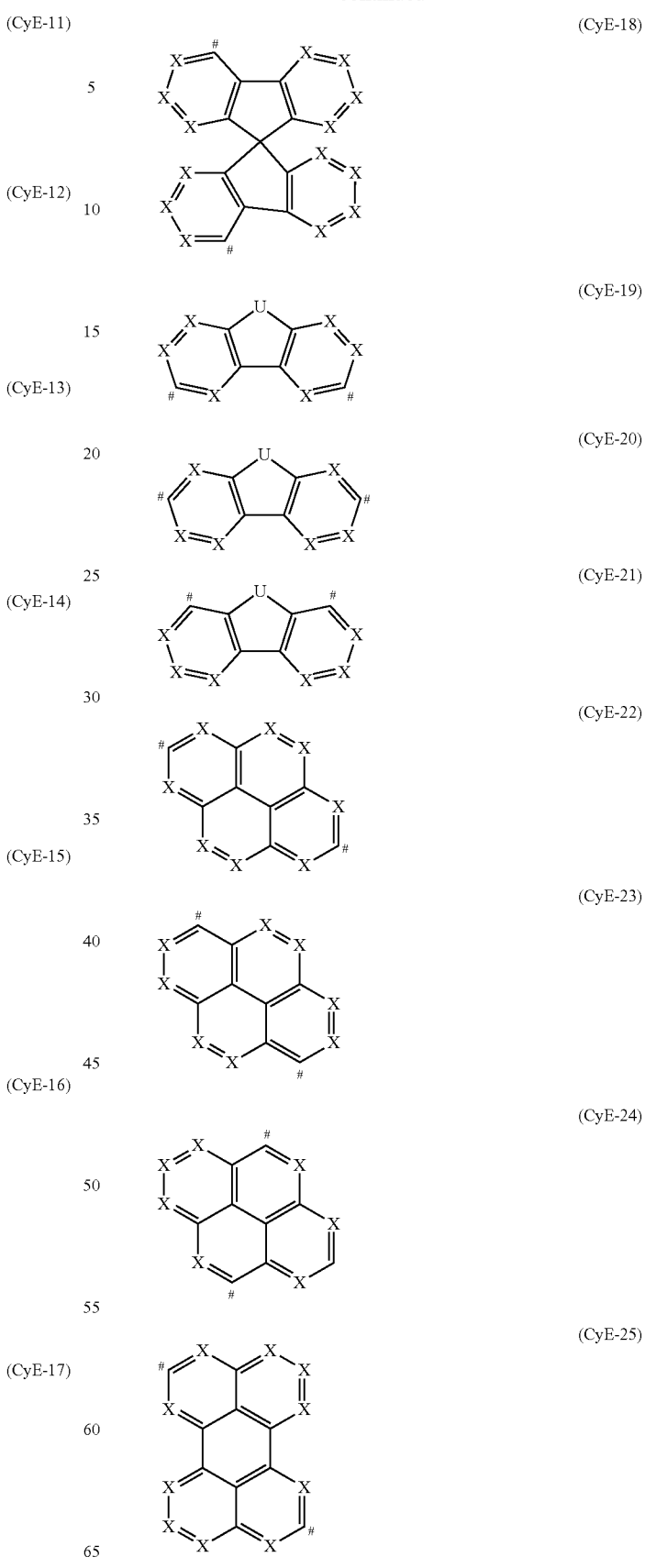

(CyE-26)
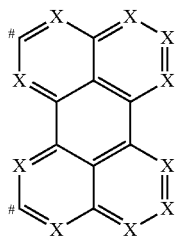

(CyE-27)
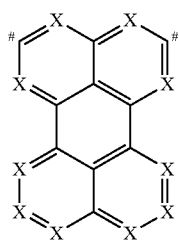

and CyF is at least one structural element selected from the formulae (CyF-1)
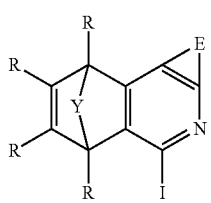

(CyF-2)
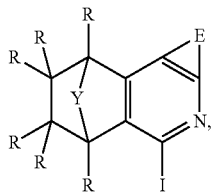

where the symbols E, R, Y and X used have the definitions given above, U is selected from O, S, C(R)$_2$, N(R), B(R), Si(R)$_2$, C=O, S=O, SO$_2$, P(R) and P(=O)R, where U is preferably O, N(R) and C(R)$_2$, very preferably O and C(R)$_2$ and especially preferably C(R)$_2$, the dotted line in the formulae CyF-1 and CyF-2 indicates the bond to the CyE group, and CyF group binds to CyE in each case at the position indicated by #.

In a further preferred embodiment of the present invention, U is O.

It may especially preferably be the case that CyF is at least one structural element selected from the formulae (CyF-3)
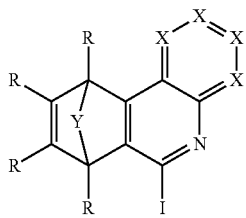

(CyF-4)
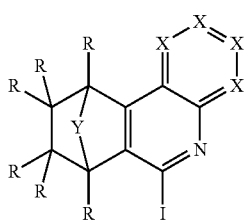

where the symbols R, Y and X used have the definitions given in claim 1, the dotted line in the formulae CyF-3 and CyF-4 indicates the bond to CyE, and CyF binds to CyE in each case at the position indicated by #.

Preferably not more than three X symbols in CyE and/or CyF are N, more preferably not more than two X symbols in CyC are N, and even more preferably not more than one X symbol in CyC is N. Especially preferably, all X symbols are CR.

Preferred embodiments of the CyE group are the structures of the following formulae (CyE-28) to (CyE-52) where U is selected from O, S, C(R)$_2$, N(R), B(R), Si(R)$_2$, C=O, S=O, SO$_2$, P(R) and P(=O)R, where U is preferably C(R)$_2$, and the CyE group binds to CyF in each case at the position indicated by #, (CyE-28)

(CyE-29)

(CyE-30)

(CyE-31)

(CyE-32)
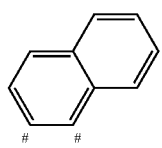

(CyE-33)
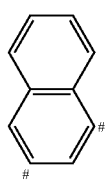

(CyE-34)
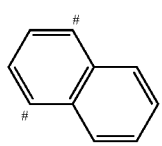
(CyE-35)
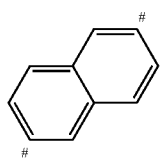
(CyE-36)
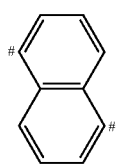
(CyE-37)
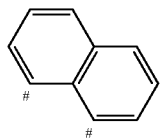
(CyE-38)
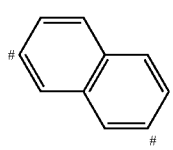
(CyE-39)
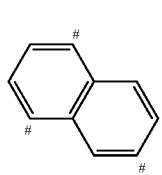
(CyE-41)
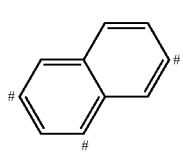
(CyE-42)
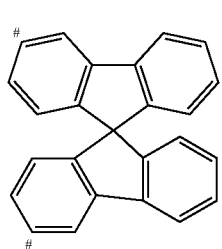
(CyE-43)
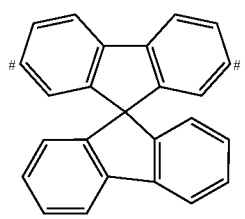
(CyE-44)
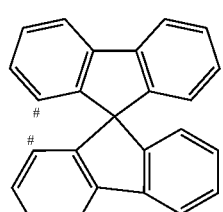
(CyE-45)
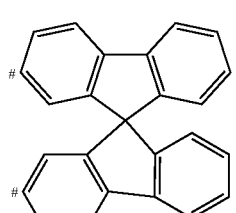
(CyE-46)
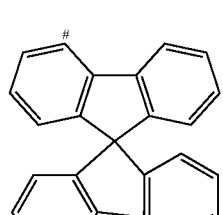
(CyE-47)
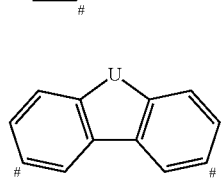
(CyE-48)
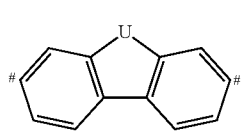
(CyE-49)
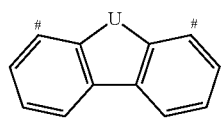
(CyE-50)
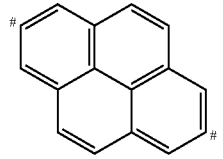

-continued
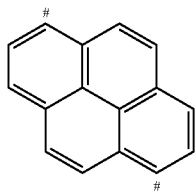 (CyE-51)
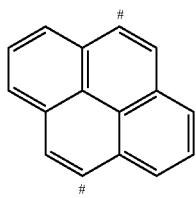 (CyE-52)
It may additionally be the case that the compounds have structures of the formula CyG(CyH)$_n$ where CyG and CyH together in each case form a ring and the symbols and indices are as follows:
n is 2 or 3
CyG is a structural element selected from the formulae
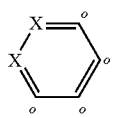 (CyG-1)
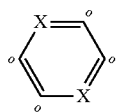 (CyG-2)
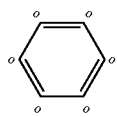 (CyG-3)
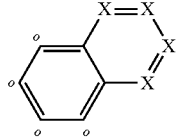 (CyG-4)
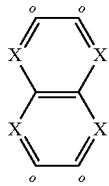 (CyG-5)
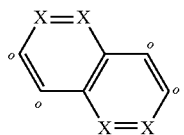 (CyG-6)
-continued
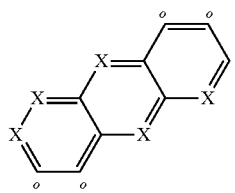 (CyG-7)
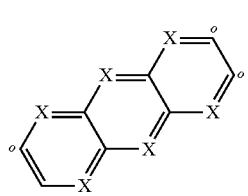 (CyG-8)
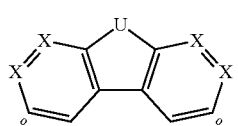 (CyG-9)
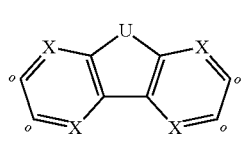 (CyG-10)
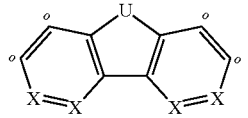 (CyG-11)
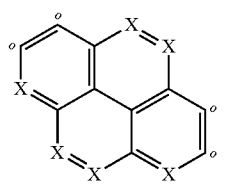 (CyG-12)
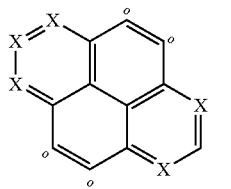 (CyG-13)
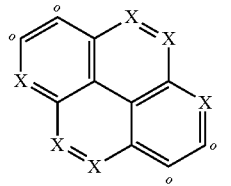 (CyG-14)

-continued

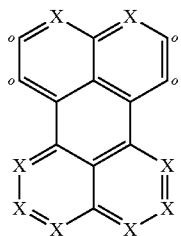
(CyG-15)

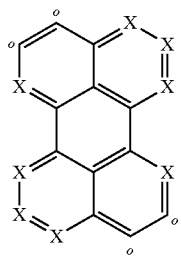
(CyG-16)

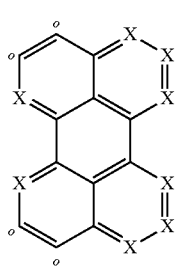
(CyG-17)

and CyH is at least one structural element selected from the following formulae:

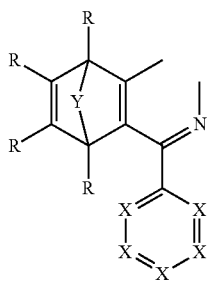
(CyH-1)

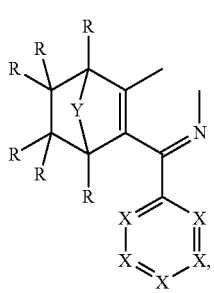
(CyH-2)

where the symbols R, Y and X used have the definitions given above, U is selected from O, S, C(R)$_2$, N(R), B(R), Si(R)$_2$, C=O, S=O, SO$_2$, P(R) and P(=O)R, where U is preferably C(R)$_2$, the dotted line in the formulae CyH-1 and CyH-2 indicates the bond to CyG, and CyH binds to CyG in each case at the positions indicated by o to form a ring.

Preferably not more than three X symbols in CyG and/or CyH are N, more preferably not more than two X symbols in CyC are N, and even more preferably not more than one X symbol in CyC is N. Especially preferably, all X symbols are CR.

Particularly preferred CyG groups are the groups of the following formulae (CyG-16) to (CyG-28):

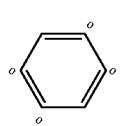
(CyG-18)

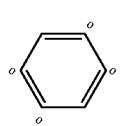
(CyG-19)

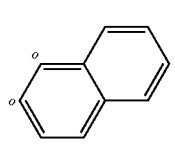
(CyG-20)

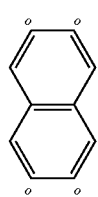
(CyG-21)

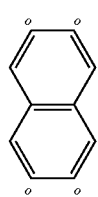
(CyG-22)

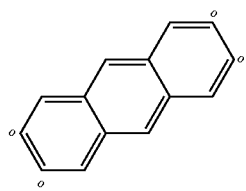
(CyG-23)

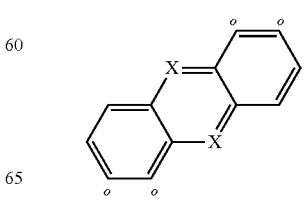
(CyG-24)

-continued (CyG-24)
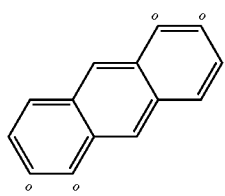

(CyG-25)
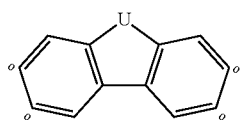

(CyG-26)
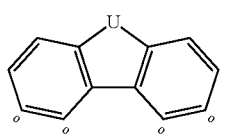

(CyG-27)
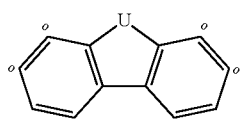

(CyG-28)
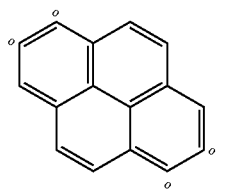

(CyG-29)
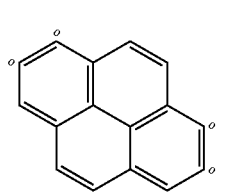

(CyG-30)
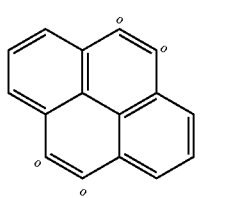

-continued (CyG-25)

(CyG-24)

(CyG-25)

(CyG-26)

(CyG-31)
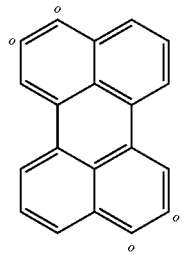

(CyG-32)
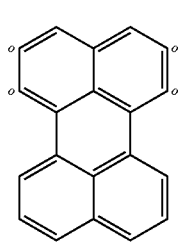

where the symbol X used has the definition given above, U is selected from O, S, C(R)$_2$, N(R), B(R), Si(R)$_2$, C=O, S=O, SO$_2$, P(R) and P(=O)R, where U is preferably C(R)$_2$, and CyH binds to CyG in each case at the positions indicated by o to form a ring.

When R radicals are bonded within the structure of the formula (I) and/or (II), these R radicals are the same or different at each instance and are preferably selected from the group consisting of H, D, F, Br, I, N(R$^1$)$_2$, CN, Si(R$^1$)$_3$, B(OR$^1$)$_2$, C(=O)R$^1$, a straight-chain alkyl group having 1 to 10 carbon atoms or an alkenyl group having 2 to 10 carbon atoms or a branched or cyclic alkyl group having 3 to 10 carbon atoms, each of which may be substituted by one or more R$^1$ radicals, where one or more hydrogen atoms may be replaced by D or F, or an aromatic or heteroaromatic ring system which has 5 to 30 aromatic ring atoms and may be substituted in each case by one or more R$^1$ radicals; at the same time, two adjacent R radicals together or R together with R$^1$ may also form a mono- or polycyclic, aliphatic or aromatic ring system. More preferably, these R radicals are the same or different at each instance and are preferably selected from the group consisting of H, D, F, N(R$^1$)$_2$, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more R$^1$ radicals; at the same time, two adjacent R radicals together or R together with R$^1$ may also form a mono- or polycyclic, aliphatic or aromatic ring system.

The compounds of the invention comprising structures of the formula (I) and/or (II) may also be chiral according to the structure. This is the case especially when they contain substituents, for example alkyl, alkoxy, dialkylamino or aralkyl groups, having one or more stereocenters. Since the base structure of the complex may also be a chiral structure, the formation of diastereomers and multiple pairs of enantiomers is possible. In that case, the compounds of the invention include both the mixtures of the different diastereomers or the corresponding racemates and the individual isolated diastereomers or enantiomers.

Preferably, the compound may be in the form of an enantiomer mixture, more preferably of a diastereomer mixture. As a result, it is unexpectedly possible to enhance the properties of electronic devices obtainable using the compounds of the invention. These properties especially include the lifetime of the devices.

According to a preferred embodiment, compounds of the formulae

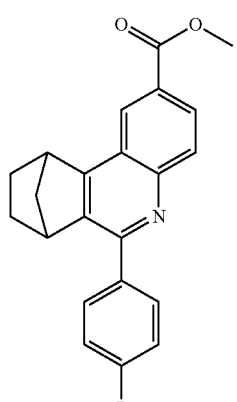
1204473-24-4

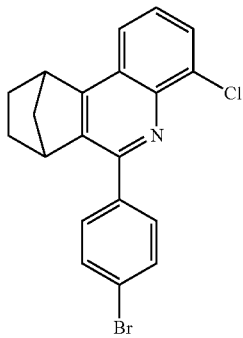
1204473-32-4

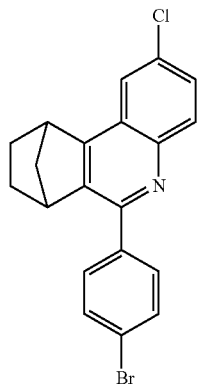
1204473-31-3 are excluded.

It may further be the case that the structures of the formulae (I) and/or (II) preferably have a maximum content of bromine atoms of 18% by weight, more preferably of 10% by weight and especially preferably of 5% by weight. According to a preferred aspect of the present invention, the compounds of the invention have a preferably a maximum content of bromine atoms of 18% by weight, more preferably of 10% by weight and especially preferably of 5% by weight.

It may additionally be the case that, in the structures of formulae (I), (II), (Ia), (IIa), (Ia1), (IIa1), (Ia2), (IIa2), (Ia3), (Ia4), (Ib), (IIb) and (Ic) and the structures of formula CyE-(CyF)$_n$ and CyG(CyH)$_n$, the symbols X are chosen such that the ratio of CR to N is preferably greater than or equal to 2, preferably greater than or equal to 3 and more preferably greater than or equal to 4.

Particularly preferred compounds include structures according to the following formulae 1 to 59:

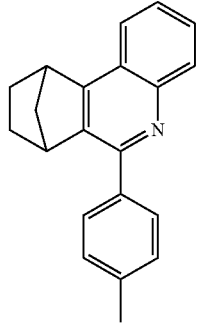
1

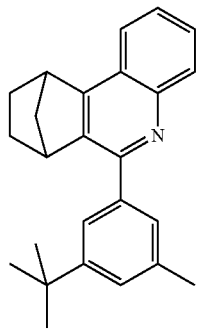
2

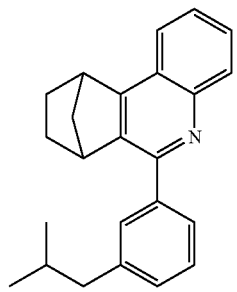
3

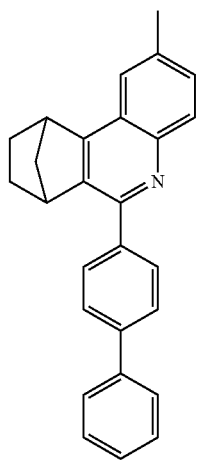
4

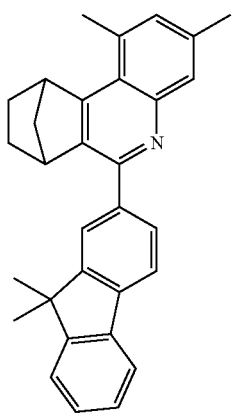
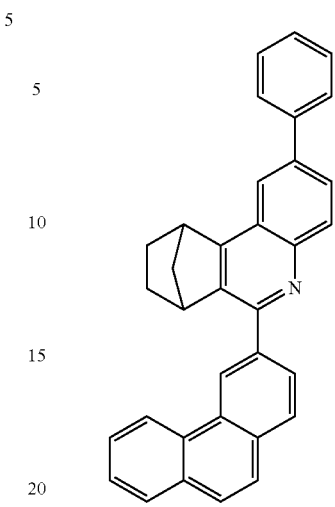
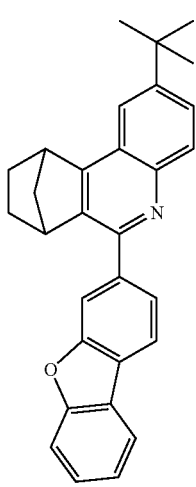
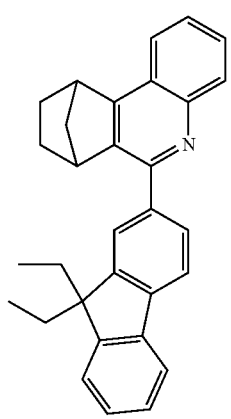
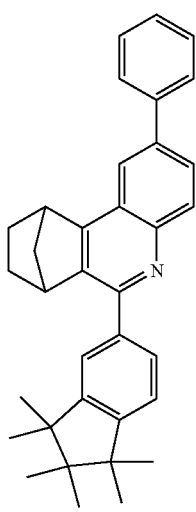
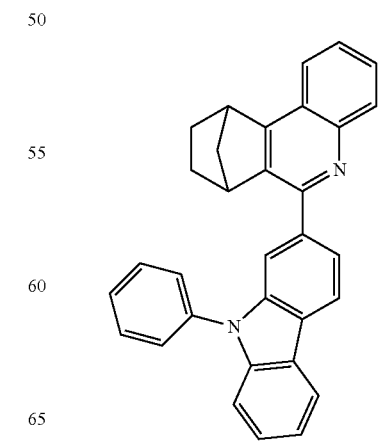

-continued
11
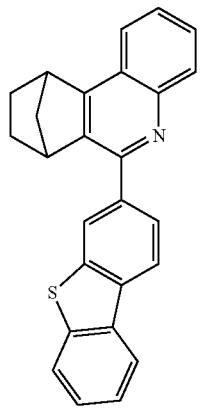
12
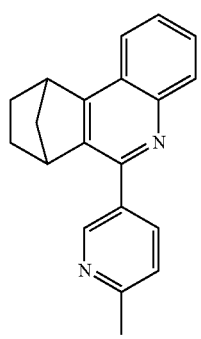
13
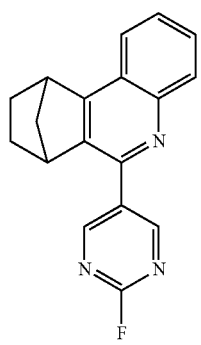
14a
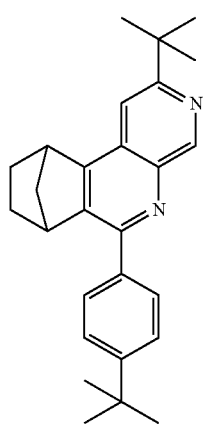
-continued
14b
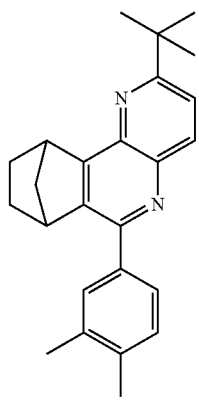
15
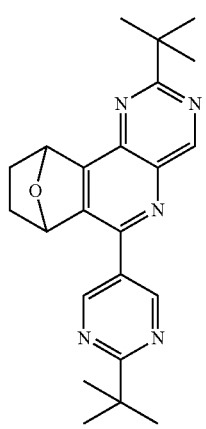
16
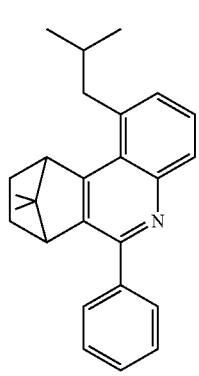
17
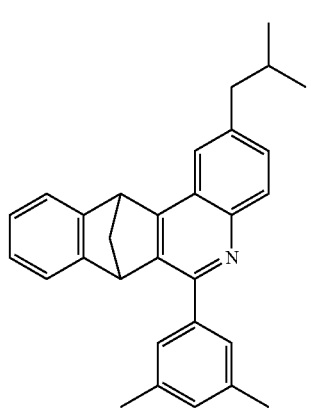

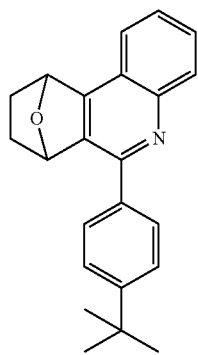
18
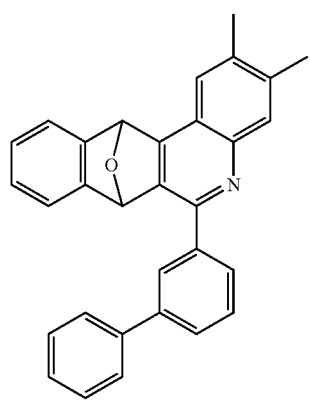
19
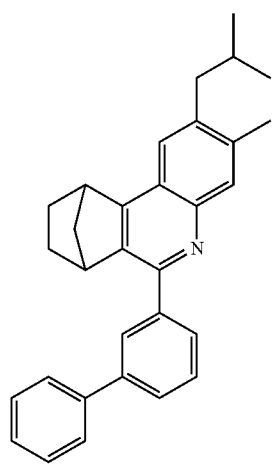
20
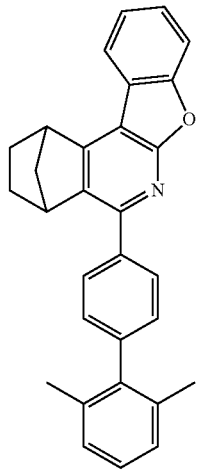
21
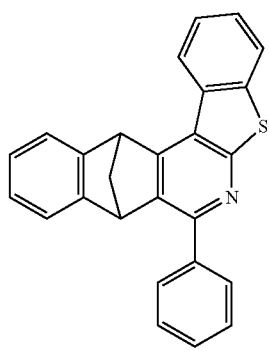
22
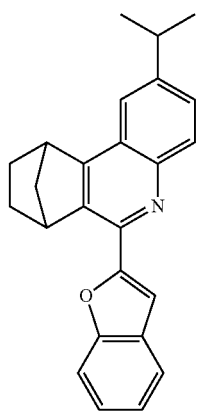
23
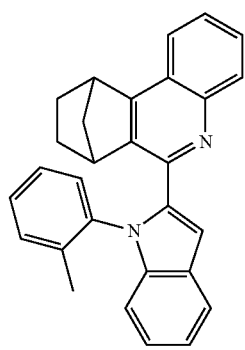
24

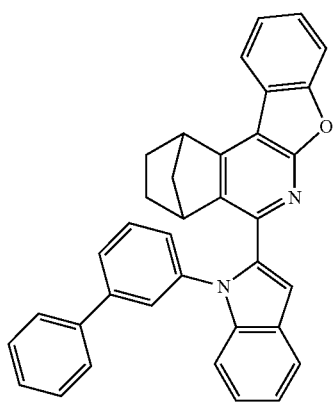
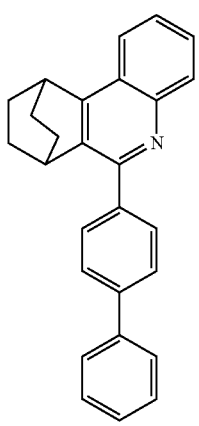
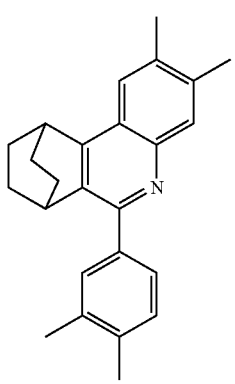
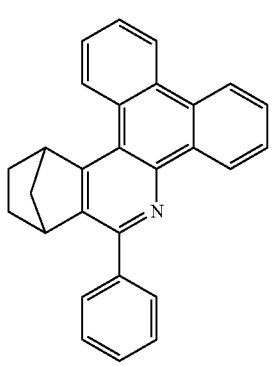
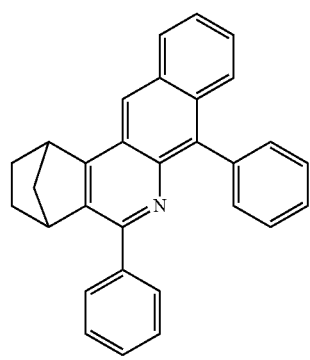

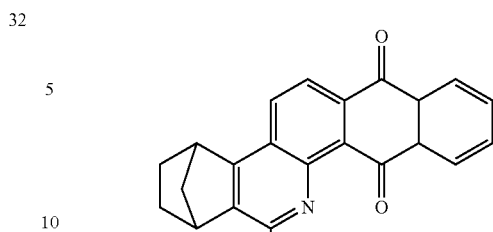
32
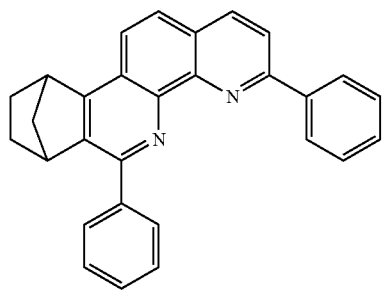
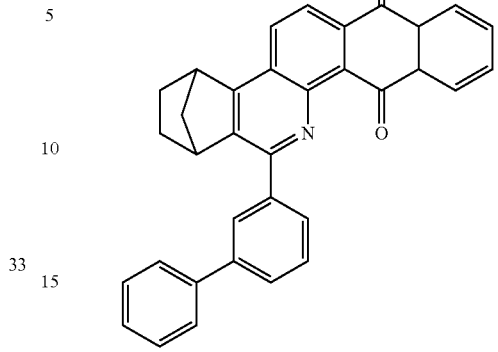
33
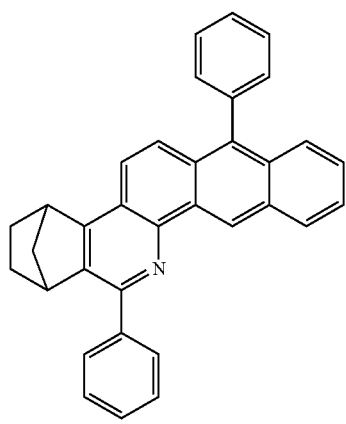
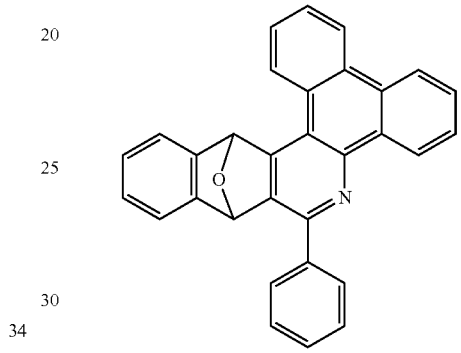
34
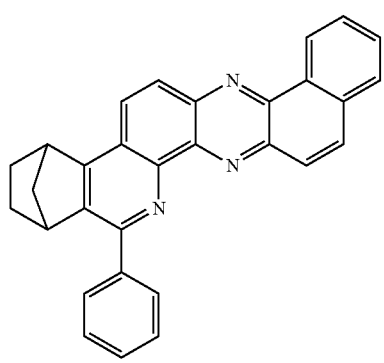
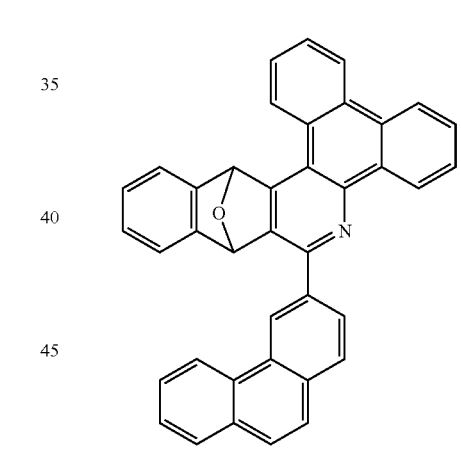
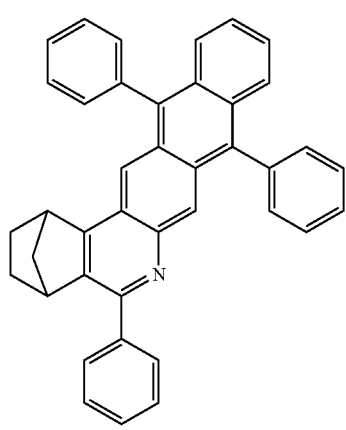
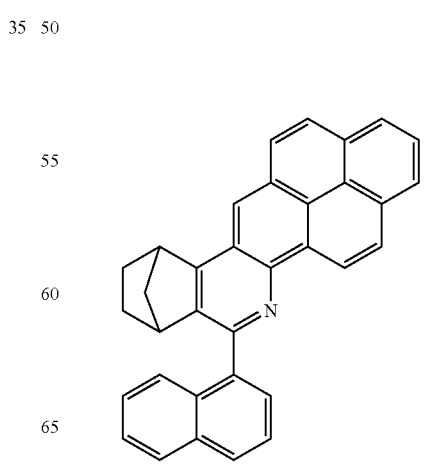

40
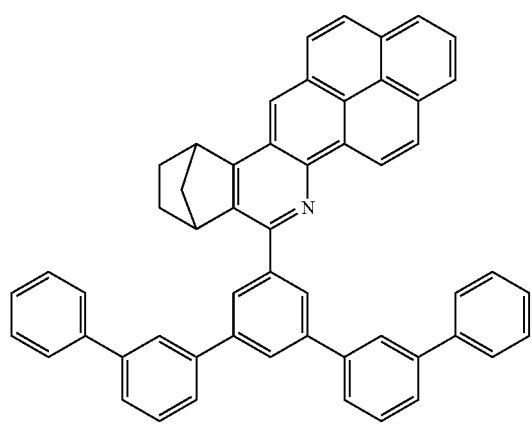
41
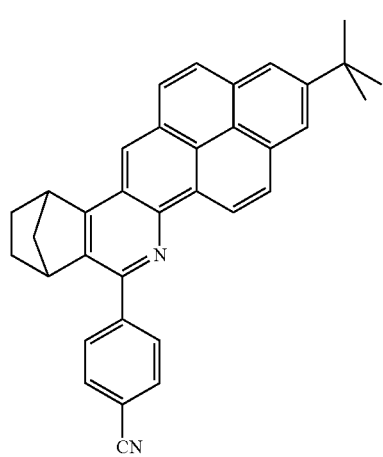
42
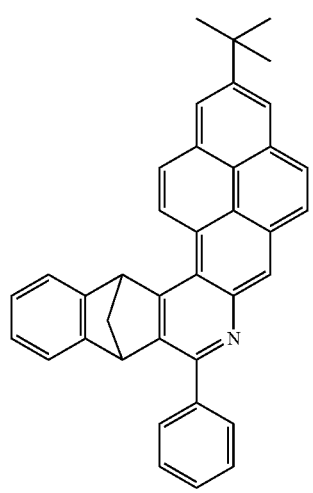
43
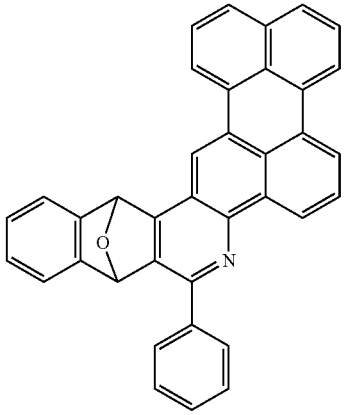
44
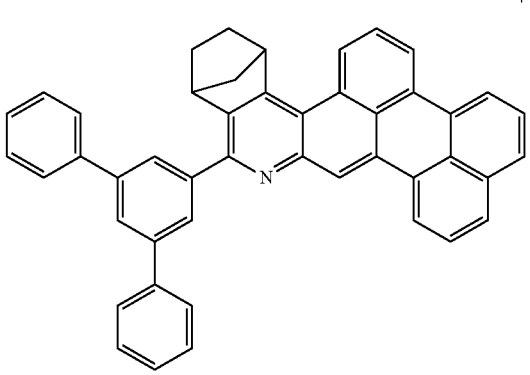
45
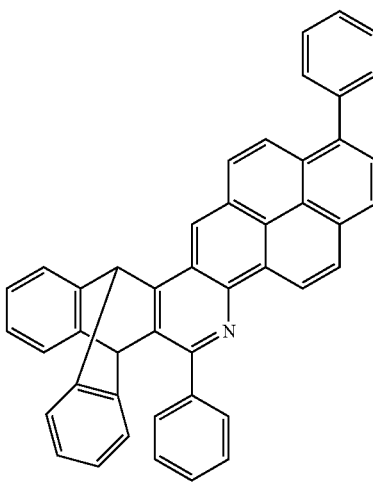
46
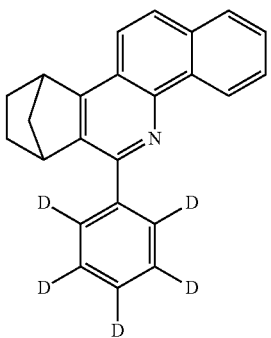

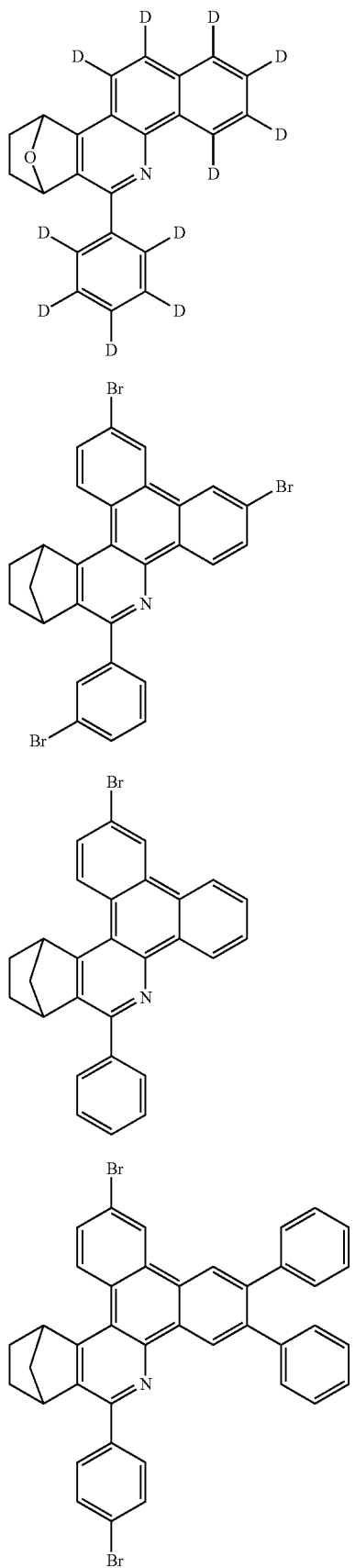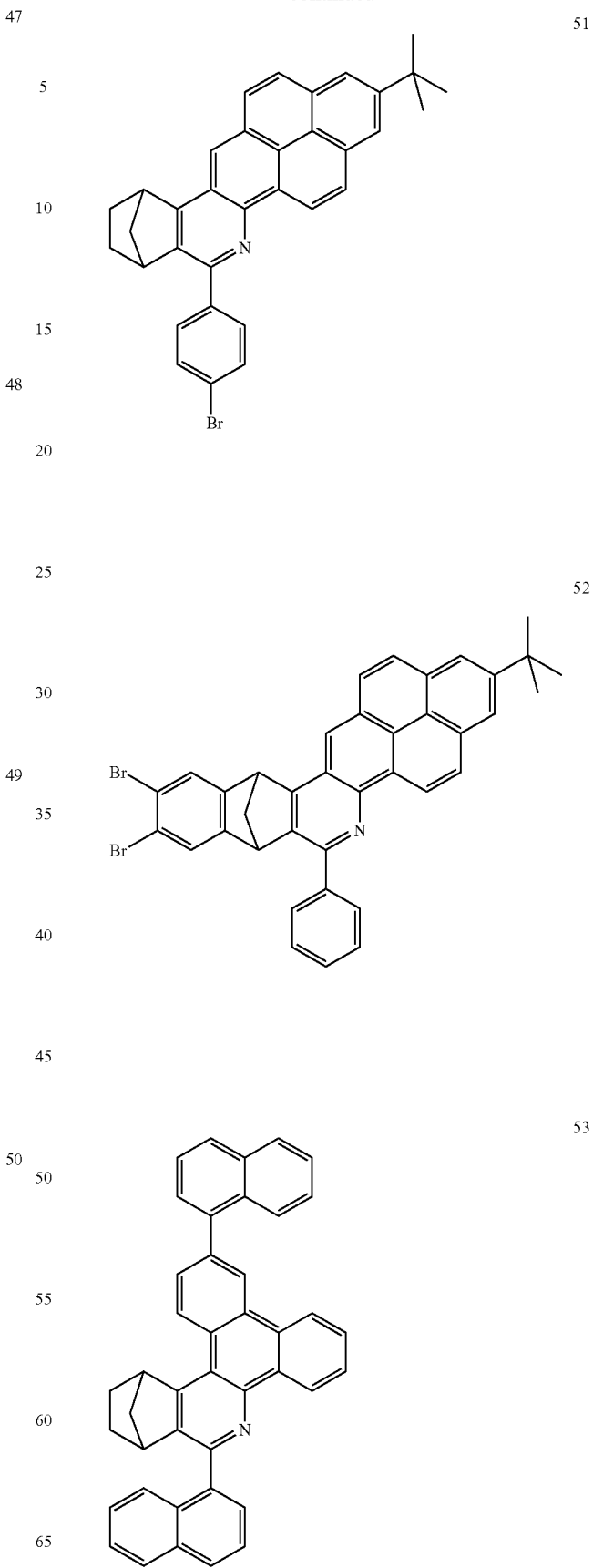

54
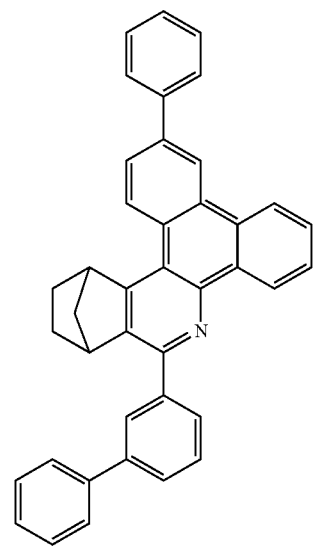
55
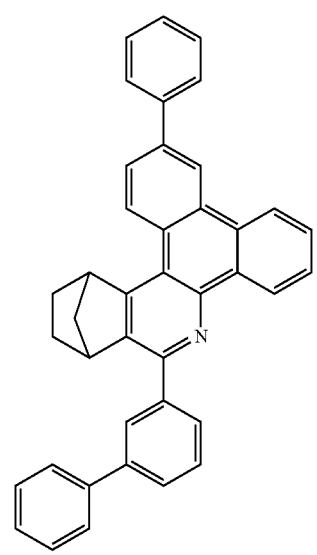
56
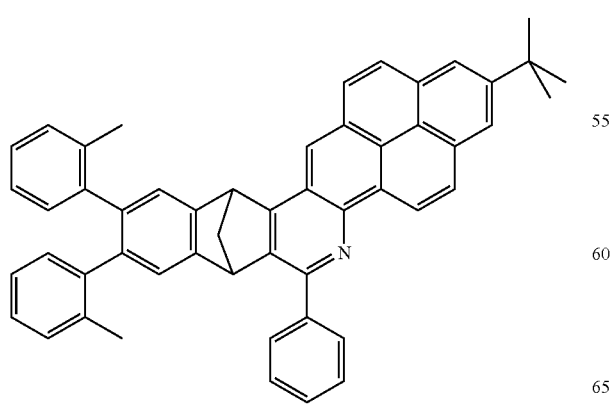
57
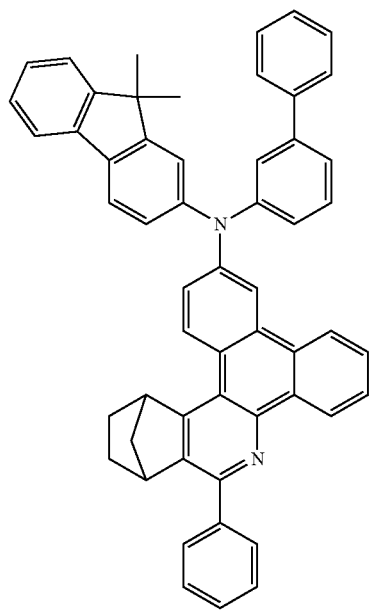
58
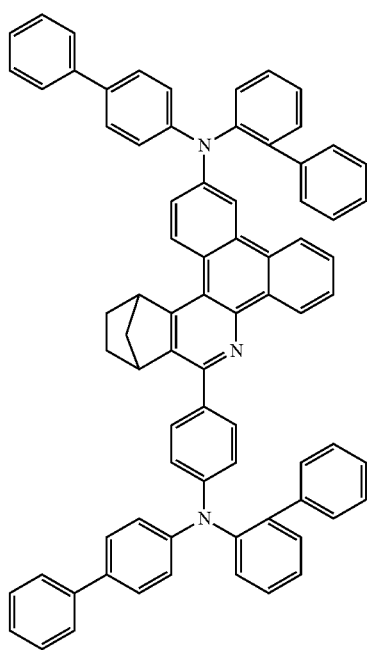

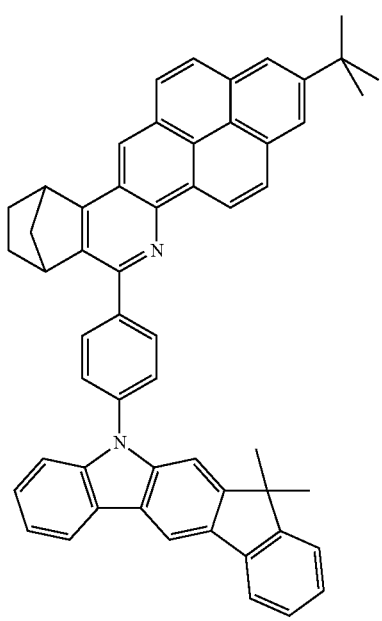
59
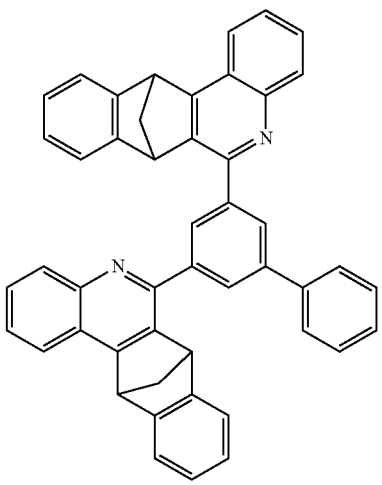
61
In addition, particularly preferred compounds include structures according to the following formulae 60 to 67:
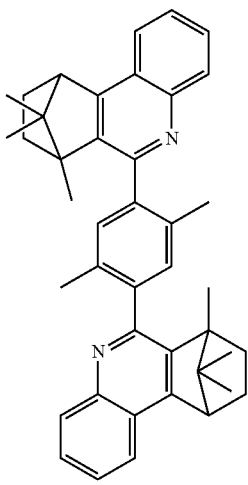
62
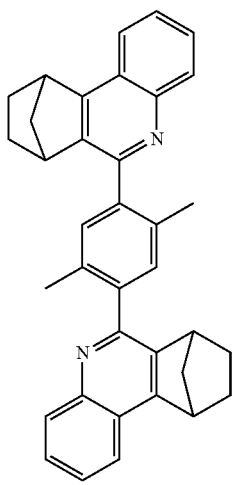
60
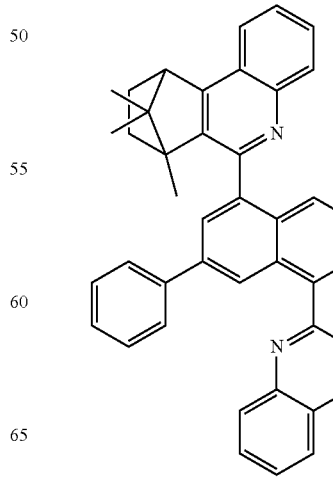
63

64
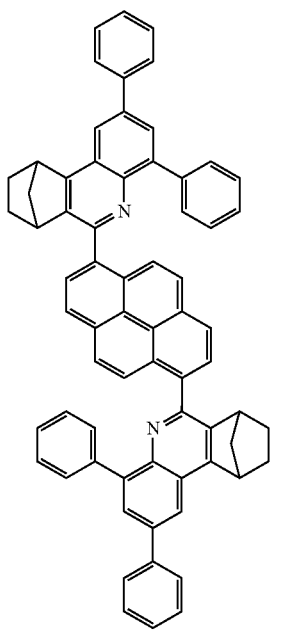
66
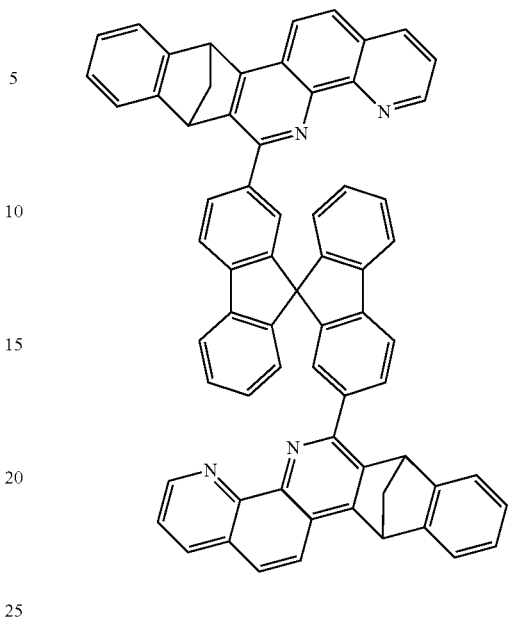
65
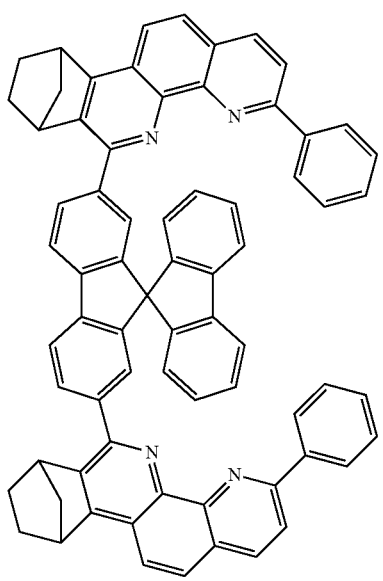
67
The compounds having at least one structure of the formulae 60, 61, 64 to 67 may preferably be present and/or be used in the form of a diastereomer mixture.
Particular preference is further given to compounds comprising structures of the following formulae 68 to 77:

68
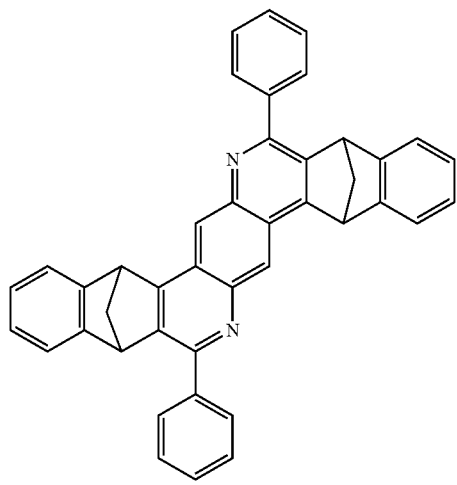
69
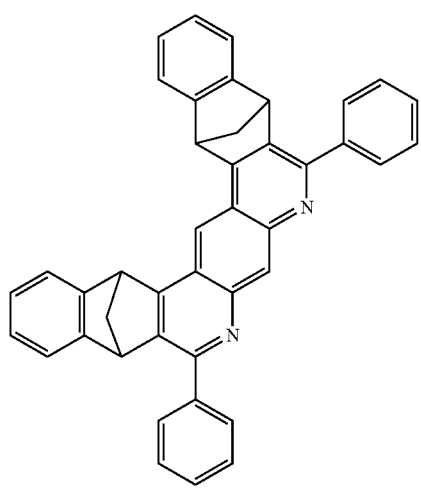
70
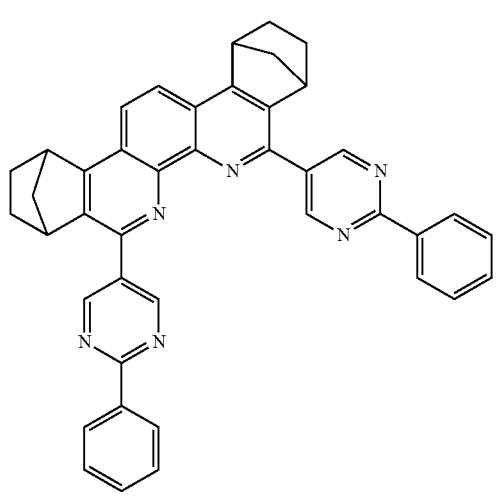
71
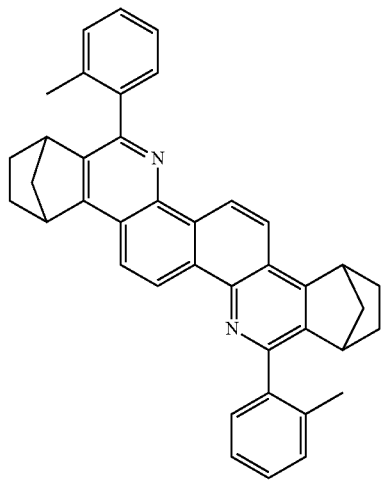
72
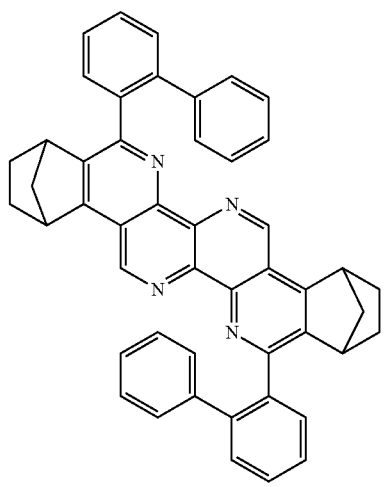
73
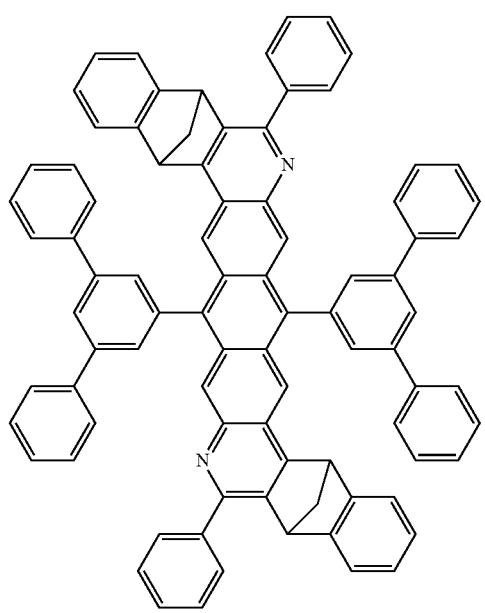

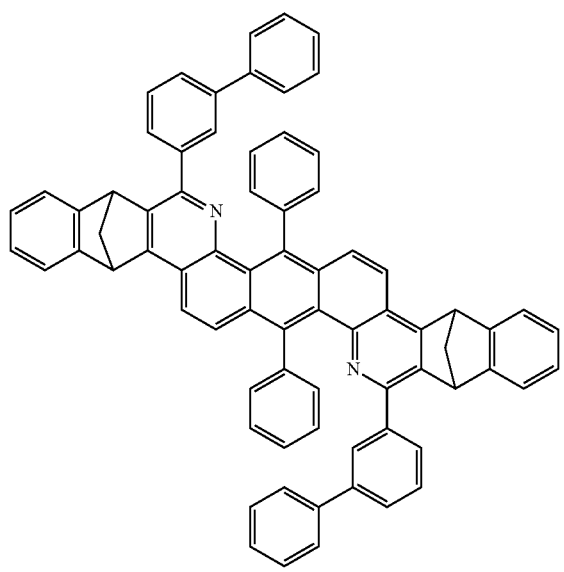
74
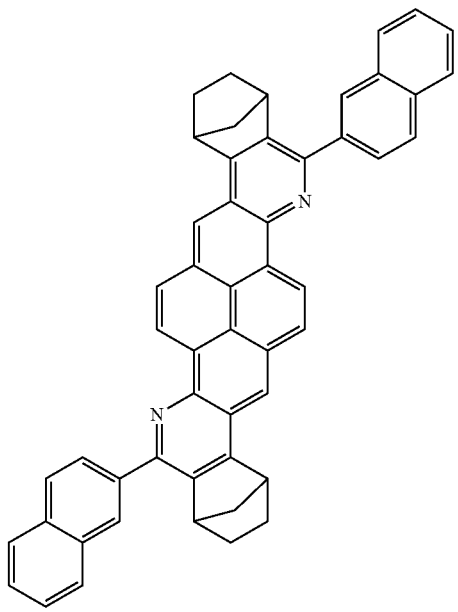
76
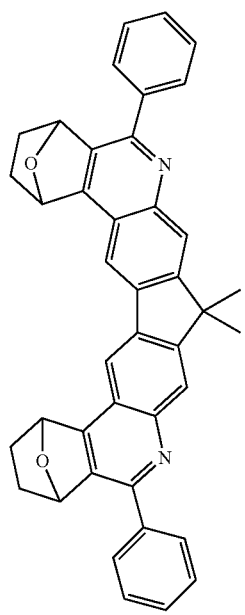
75
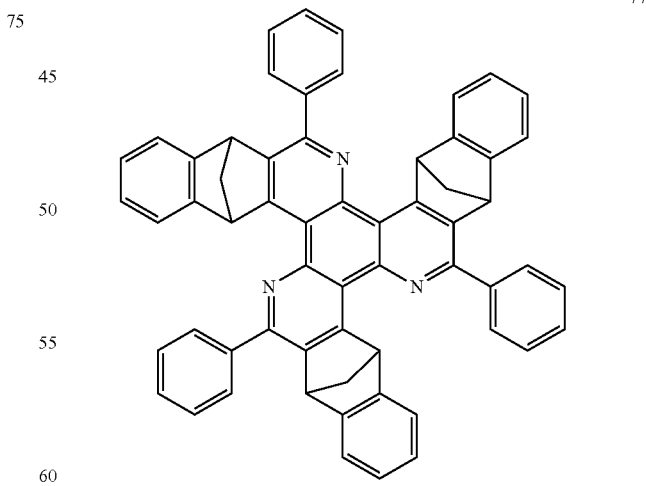
77
The compounds having at least one structure of the formulae 68 to 77 may preferably be present and/or be used in the form of a diastereomer mixture.
In addition, particularly preferred compounds include structures according to the following formulae 78 to 85:

78
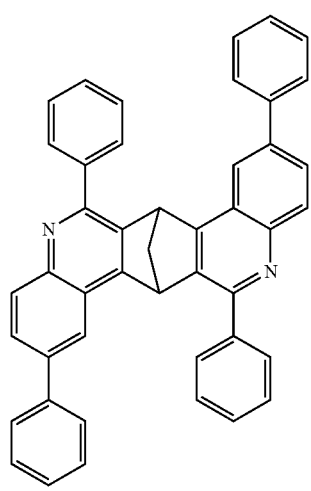
81
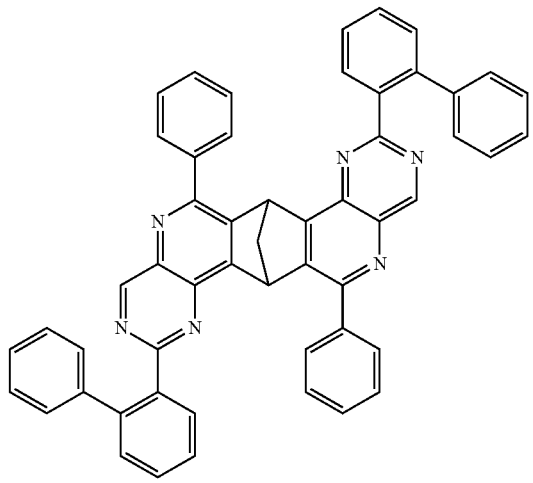
79
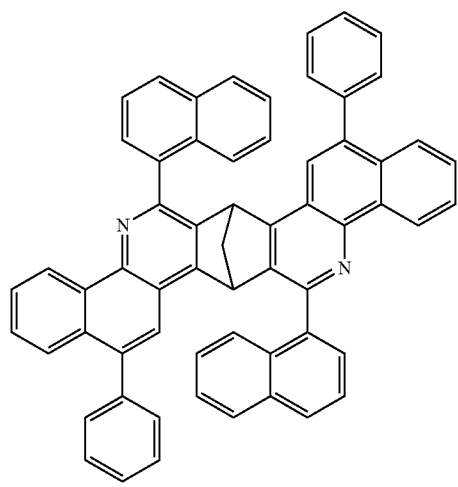
82
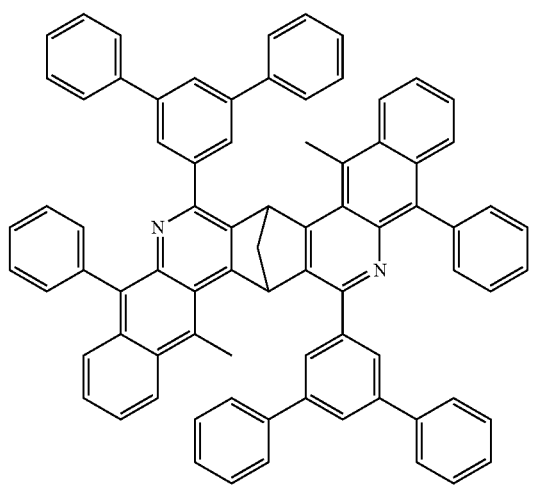
80
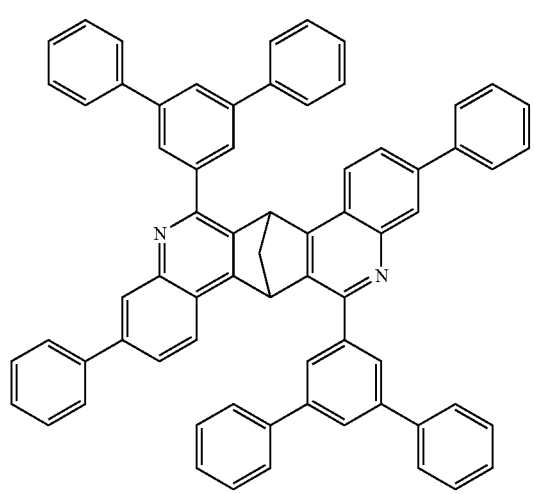
83
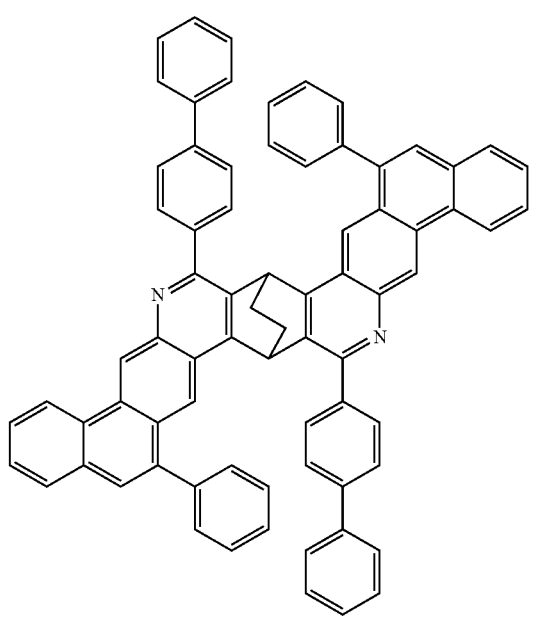

-continued

84

85

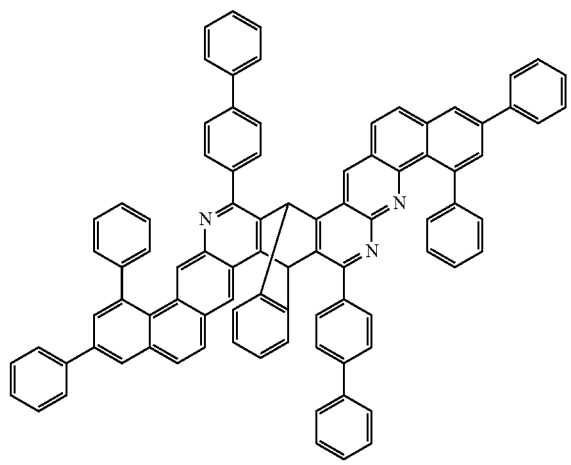

The abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing compounds comprising structures of formula (I) and/or (II) by reacting at least one aldehyde with at least one aromatic or heteroaromatic amine and at least one bicyclic olefin. Reaction may also be effected using mixtures of aldehydes, aromatic amines and/or bicyclic olefins. Preference is given, however, to reaction of pure substances in order to obtain a defined product.

An illustrative example of a reaction is shown by the following scheme:

The compounds of the invention are preferably obtainable by Lewis acid-catalyzed reaction of arylamines with aldehydes to give imines and subsequent Povarov reaction with activated olefins to give tetrahydrolisoquinolines and subsequent dehydrogenation thereof. The reaction sequence of imine formation and Povarov reaction can preferably be conducted as a one-pot process. Activated olefins used are bi- and tricyclic olefins, for example of the bicyclo[2.2.1](norbornene) and bicyclo[2.2.2](barrelene) types.

Lewis acids used include main group element compounds such as boron halides, aluminum halides, gallium halides and indium halides and adducts thereof, more preferably boron trifluoride, boron trifluoride etherates, aluminum trichloride, gallium trichloride, indium trichloride, phosphorus halides, bismuth halides and antimony halides such as bismuth trichloride, or else transition metal and lanthanoid compounds, preferably Zr, Cu, Ag, Au, Zn, Y, La, Yb salts such as halides, acetates and triflates.

The dehydrogenation of the substituted tetrahydroisoquinoline can be effected by processes known from the literature, for example by transition metal-catalyzed dehydrogenation or transfer dehydrogenation, or by oxidation with metal oxides (e.g. manganese dioxide) or quinones (e.g. DDQ).

In addition, it is possible to use aldehydes having one and preferably two or more aldehyde group(s), preference being given to using aromatic or heteroaromatic aldehydes. The preferred aldehydes include the compounds detailed in the synthesis examples.

The preferred monoaldehydes include, for example, benzaldehyde (CAS 100-52-7), benzaldehydes substituted by alkyl groups, 2-naphthaldehyde (CAS 66-99-9), 6-tert-butyl-3-formylpyridine (CAS 391900-69-9), 2-tert-butylpyrimidine-5-carbaldehyde (CAS 104461-06-5), 3-phenylbenzaldehyde (CAS 1204-60-0), 2-benzofurancarboxaldehyde (CAS 4265-16-1), 3-dibenzofurancarboxaldehyde (CAS 51818-91-8), 9,9'-spirobi[9H-fluorene]-2-carboxaldehyde (CAS 124575-66-2) and [1,1':3',1''-terphenyl]-5'-carboxaldehyde (CAS 220955-80-6).

The preferred dialdehydes include 1,3-phthalaldehyde (CAS 626-19-7), 1,4-phthalaldehyde (CAS 623-27-8), 1,5-naphthalenedicarboxaldehyde (CAS 7141-15-3), 1,6-pyrenedicarboxaldehyde (CAS 252338-01-5) and 9,9'-spirobi[9H-fluorene]-2,7-dicarboxaldehyde (CAS 856014-12-5).

In addition, it is possible to use aromatic or heteroaromatic amines having one and preferably two or more amine group(s). The preferred aromatic or heteroaromatic amines include the compounds detailed in the synthesis examples.

The preferred monoamines include, for example, aniline (CAS 62-63-3), 4-methylaniline (CAS 106-49-0), 3,5-dimethylaniline, 4-t-butylaniline (CAS 769-92-6), 4-phenylaniline (CAS 92-67-1), 2-tert-butyl-5-aminopyrimidine (CAS 59950-55-9), 2-benzofuranamine (CAS 139266-08-3), 2-aminobenzo[b]thiophene (CAS 4521-30-6), 1-aminonaphthalene (CAS 134-32-7), 8-aminoquinoline (CAS 578-66-5), 1-anthracenamine (CAS 610-49-1), 2-anthracenamine (CAS 613-13-8) and 1-phenazinamine (9CI) (CAS 2876-22-4).

The preferred diamines include p-phenylenediamine (CAS 106-50-3), m-phenylenediamine (CAS 108-45-2), o-phenylenediamine (CAS 95-54-5), 1,5-naphthalenediamine (CAS 2243-62-1) and 1,5-naphthyridine-4,8-diamine (CAS 64761-26-8).

In addition, it is possible to use bicyclic olefins having one, two or more double bond(s). The preferred bicyclic olefins include the compounds detailed in the synthesis examples.

The preferred bicyclic olefins include norbornene (CAS 498-66-8), norbornadiene (CAS 121-46-0), 7,7-dimethylnorbornene (CAS 6541-60-2), benzonorbornadiene (CAS 4453-90-1), 7-oxanorbornene (CAS 6705-50-6), 7-oxabenzonorbornadiene (CAS 573-57-9), bicyclo[2.2.2]-2-octene (CAS 931-64-6), bicyclo[2.2.2]octa-2,5-diene (CAS 500-23-2), bicyclo[2.2.2]octa-2,5,7-triene (CAS 500-24-3) and 1,4-dihydro-1,4-ethenonaphthalene (CAS 7322-47-6).

It is possible with preference to use a Lewis acid as catalyst in a reaction, and it is advantageously possible to use boron trifluoride etherate (CAS 60-29-7).

To obtain compounds having the structures of the invention, an oxidation is generally conducted. For this purpose, standard oxidizing agents are suitable, for example manganese dioxide or quinones.

The reactions detailed above are known to the person skilled in the art in principle by the name "Povarov reaction" and are described extensively in the literature with further references, for example in J. Org. Chem. 75 (2010) 702-715 and in Tetrahedron 65 (2009) 2721-2750.

An intermediate obtained after the reaction of at least one aldehyde with at least one aromatic amine and at least one bicyclic olefin can be converted in a coupling reaction.

Suitable reactions for formation of C—C bonds and/or C—N bonds are known to those skilled in the art and are described in the literature. Particularly suitable and preferred coupling reactions which all lead to C—C bonds are those according to BUCHWALD, SUZUKI, YAMAMOTO, STILLE, HECK, NEGISHI, SONOGASHIRA and HIYAMA.

It is possible by these processes, if necessary followed by purification, for example recrystallization or sublimation, to obtain the compounds of the invention comprising structures of the formula (I) and/or formula (II) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in sufficient concentrations soluble, in order to be able to process the complexes from solution. These soluble compounds are of particularly good suitability for processing from solution, for example by printing methods. In addition, it should be emphasized that the compounds of the invention comprising at least one structure of the formulae (I) and/or (II) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formulae (I) and/or (II) or compounds of the invention, wherein one or more bonds of compounds of the invention or of the structures of the formulae (I) and/or (II) to the polymer, oligomer or dendrimer are present. According to the linkage of the structures of the formulae (I) and/or (II) or of the compounds, these therefore form a side chain of the oligomer or polymer or are bonded within the main chain. The polymers, oligomers or dendrimers may be conjugated, partly conjugated or non-conjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the Invention are homopolymerized or copolymerized with further monomers. Preference is given to copolymers wherein the units of formula (1) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In addition, the present compounds may have a relatively low molecular weight. The present invention accordingly further provides a compound having a molecular weight of preferably not more than 10 000 g/mol, more preferably not more than 5000 g/mol and especially preferably not more than 3000 g/mol.

In addition, it is a feature of preferred compounds that they are sublimable. These compounds generally have a molar mass of less than about 1200 g/mol.

Additionally of particular interest are compounds of the invention which feature a high glass transition temperature. In this connection, preference is given especially to compounds of the invention comprising structures of the general formulae (I) and (II) having a glass transition temperature of at least 70° C., more preferably of at least 110° C., even more preferably of at least 125° C. and especially preferably of at least 150° C., determined in accordance with DIN 51005.

The compounds of the invention may include at least one metal atom selected from iridium, ruthenium, palladium, platinum, osmium or rhenium, preferably iridium or platinum. These compounds are especially suitable as phosphorescent emitters. For example, the above-detailed compounds 1 to 27 and the compounds A1 to A27 detailed in the examples may be reacted with platinum and/or iridium to give emitting metal complexes.

Preference is given especially to metal complexes of the formula (M-1)

  Formula (M-1)

where the symbols and indices used are as follows:
M is iridium or platinum;
L is the same or different at each instance and is a ligand comprising at least one structure of the formulae (I) and/or (II);
L' is the same or different at each instance and is any coligand;
n is 1, 2 or 3;
m is 0, 1, 2, 3 or 4.

For example, the corresponding free ligands L and optionally L' may with metal alkoxides of the formula (M-2), with metal ketoketonates of the formula (M-3), with metal halides of the formula (M-4), with dimeric metal complexes of the formula (M-5) or with metal complexes of the formula (M-6)

  Formula (M-2)

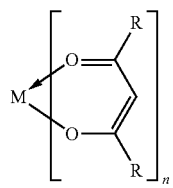  Formula (M-3)

  Formula (M-4)

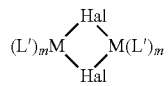  Formula (M-5)

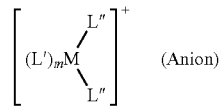  Formula (M-6)

where the symbols M, m, n and R have the definitions given above, Hal=F, Cl, Br or I, L" is an alcohol, especially an alcohol having 1 to 4 carbon atoms or a nitrile, especially acetonitrile or benzonitrile, and (Anion) is a noncoordinating anion, for example triflate.

It is likewise possible to use metal compounds, especially iridium compounds, bearing both alkoxide and/or halide and/or hydroxyl and ketoketonate radicals. These compounds may also be charged. Corresponding iridium compounds of particular suitability as reactants are disclosed in WO 2004/085449. Particularly suitable are $[IrCl_2(acac)_2]^-$, for example $Na[IrCl_2(acac)_2]$, metal complexes with acetylacetonate derivatives as ligand, for example $Ir(acac)_3$ or tris(2,2,6,6-tetramethylheptane-3,5-dionato)iridium, and $IrCl_3 \cdot xH_2O$ where x is typically a number from 2 to 4.

Suitable platinum reactants are, for example, $PtCl_2$, $K_2[PtCl_4]$, $PtCl_2(DMSO)_2$, $Pt(Me)_2(DMSO)_2$ or $PtCl_2(benzonitrile)_2$.

The synthesis of the complexes is preferably conducted as described in WO 2002/060910, WO 2004/085449 and WO 2007/065523. Heteroleptic complexes can be synthesized, for example, according to WO 2005/042548 as well. In this case, the synthesis can, for example, also be activated by thermal or photochemical means and/or by microwave radiation. In a preferred embodiment of the invention, the reaction is conducted without the use of an additional solvent in the melt. "Melt" here means that the ligand is in molten form and the metal precursor is dissolved or suspended in this melt. For activation of the reaction, it is additionally also possible to add a Lewis acid, for example a silver salt or $AlCl_3$.

The present invention still further provides a formulation comprising a compound of the invention or an oligomer, polymer or dendrimer of the invention and at least one further compound. The further compound may, for example, be a solvent. The further compound may alternatively be a further organic or inorganic compound which is likewise used in the electronic device, for example a matrix material. This further compound may also be polymeric.

The present invention still further provides a composition comprising a compound of the invention and at least one further organic functional material selected from the group consisting of fluorescent emitters, phosphorescent emitters, host materials, matrix materials, electron transport materials, electron injection materials, hole conductor materials, hole injection materials, electron blocker materials and hole blocker materials.

The above-described compound comprising structures of the formulae (I) and/or (II) or the above-detailed preferred embodiments can preferably be used as active component in an electronic device. An electronic device is understood to mean any device comprising anode, cathode and at least one layer, said layer comprising at least one organic or organometallic compound. The electronic device of the invention thus comprises anode, cathode and at least one layer containing at least one compound comprising structures of the formulae (I) and/or (II). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) and organic laser diodes (O-lasers), containing at least one compound comprising structures of the formulae (I) and/or (II) in at least one layer. Particular preference is given to organic electroluminescent devices. Active components are generally the organic or inorganic materials introduced between the anode and cathode, for example charge injection, charge transport or charge blocker materials, but especially emission materials and matrix materials. The compounds of the invention exhibit particularly good properties as emission material in organic electroluminescent devices. A preferred embodiment of the invention is therefore organic electroluminescent devices. In addition, the compounds of the invention can be used for production of singlet oxygen or in photocatalysis.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) and/or (II) or the above-detailed preferred embodiments as emitting compound and/or as matrix material in one or more emitting layers, preferably in combination with a further matrix material and/or a further emitting compound.

In this case, at least one compound of the invention, preferably a metal complex of the invention comprising structures of the formula (I) and/or (II), can be used as emitting compound in an emitting layer, preferably in combination with a matrix material comprising compounds having structures of formula (I) or (II). In addition, it is possible to combine a metal complex of the invention comprising structures of formula (I) and/or (II) with a matrix material lacking structures of formula (I) and/or (II). Furthermore, it is possible to use a compound of the invention comprising structures of formula (I) and/or (II) as matrix material, in which case this matrix material can be combined with the metal complex lacking structures of formula (I) and/or (II).

When the compound of the invention comprising structures of the formula (I) and/or (II) is used as emitting compound in an emitting layer, it is preferably used in combination with one or more matrix materials. The mixture of the compound of the invention comprising structures of formula (I) and/or (II) and the matrix material contains between 0.1% and 99% by volume, preferably between 1% and 90% by volume, more preferably between 3% and 40% by volume and especially between 5% and 15% by volume of the compound of the invention comprising structures of formula (I) and/or (II), based on the overall mixture of emitter and matrix material. Correspondingly, the mixture contains between 99.9% and 1% by volume, preferably between 99% and 10% by volume, more preferably between 97% and 60% by volume and especially between 95% and 85% by volume of the matrix material, based on the overall mixture of emitter and matrix material.

The matrix materials used may generally be any materials which are known for the purpose according to the prior art. The triplet level of the matrix material is preferably higher than the triplet level of the emitter.

Suitable matrix materials for the compounds of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

In addition, the compounds of the invention can be used as matrix materials. In this case, the matrix materials of the invention can be used together either with emitting compounds comprising at least one structure of formulae (I) and/or (II) or with emitting compounds having no structure of formulae (I) and/or (II). In this connection, it should be emphasized that the aforementioned ratios of matrix material to emitting compounds apply correspondingly.

It may also be preferable to use a plurality of different matrix materials as a mixture, especially of at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex of the invention. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum. For example, it is possible to use the compounds of the invention comprising structures of formula (I) and/or (II) as co-matrix for longer-wave emitting triplet emitters, for example for green- or red-emitting triplet emitters.

The compounds of the invention can also be used in other functions in the electronic device, for example as hole transport material in a hole injection or transport layer, as charge generation material or as electron blocker material. It is likewise possible to use the complexes of the invention as matrix material for other phosphorescent metal complexes in an emitting layer.

The present invention further provides an electronic device, preferably an organic electroluminescent device, one or more compounds of the invention and/or at least one oligomer, polymer or dendrimer of the invention in one or more electron-conducting layers, as electron-conducting compound.

The present invention additionally provides an electronic device, preferably an organic electroluminescent device, one or more compounds of the invention and/or at least one oligomer, polymer or dendrimer of the invention in one or more hole-conducting layers, more preferably as hole-conducting compound.

Preferred cathodes are metals having a low work function, metal alloys or multilayer structures composed of various metals, for example alkaline earth metals, alkali metals, main group metals or lanthanolds (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. On the other hand, metal/metal oxide electrodes (e.g. $Al/Ni/NiO_x$, $Al/PtO_x$) may also be preferred. For some applications, at least one of the electrodes has to be transparent or partly transparent in order to enable the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices Is severely shortened in the presence of water and/or air.

Additionally preferred is an electronic device, especially an organic electroluminescent device, characterized in that one or more layers are coated by a sublimation process. In this case, the materials are applied by vapor deposition in vacuum sublimation systems at an initial pressure of typically less than $10^{-5}$ mbar, preferably less than 10\$ mbar. It is also possible that the initial pressure is even lower or even higher, for example less than $10^{-7}$ mbar.

Preference is likewise given to an electronic device, especially an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, especially an organic electroluminescent device, characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device can also be produced as a hybrid system by applying one or more layers from solution and applying one or more other layers by vapor deposition. For example, it is possible to apply an emitting layer comprising a compound of the invention comprising structures of formula (I) and/or (II) and a matrix material from solution, and to apply a hole blocker layer and/or an electron transport layer thereto by vapor deposition under reduced pressure.

These methods are known in general terms to those skilled in the art and can be applied without difficulty to electronic devices, especially organic electroluminescent devices comprising compounds of the invention comprising structures of formula (I) and/or (II) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (I) and/or (II) as emitting materials, as electron-conducting materials or as hole-conducting materials have a very good lifetime.
2. Electronic devices, especially organic electroluminescent devices, comprising compounds, oligomers, polymers or dendrimers having structures of formula (I) and/or (II) as emitting materials, as electron-conducting materials or as hole-conducting materials have excellent efficiency. More particularly, efficiency is much higher compared to analogous compounds containing no structural unit of formula (I) or formula (II).

3. The compounds of the invention comprising at least one metal atom, preferably selected from Ir and Pt, have a very narrow emission spectrum in some cases, which leads to a high color purity in the emission, as is desirable particularly for display applications.

4. The compounds of the invention comprising at least one metal atom, preferably selected from Ir and Pt, have reduced aggregation compared to analogous compounds containing no structural unit of formula (I) or formula (II). This is manifested in a lower sublimation temperature and a higher solubility, and in reduced triplet-triplet quenching in the electroluminescent device.

5. The compounds, oligomers, polymers and dendrimers of the invention having structures of the formula (I) and/or (II) exhibit very high stability and lead to compounds having a very long lifetime.

6. With compounds, oligomers, polymers or dendrimers having structures of formula (I) and/or (II), it is possible to avoid the formation of optical loss channels in electronic devices, especially organic electroluminescent devices. As a result, these devices feature a high PL efficiency and hence high EL efficiency of emitters, and excellent energy transmission of the matrices to dopants.

7. The use of compounds, oligomers, polymers or dendrimers having structures of formula (I) and/or (II) in layers of electronic devices, especially organic electroluminescent devices, leads to a high mobility of the electron conductor structures.

8. Compounds, oligomers, polymers and dendrimers having structures of formula (I) and/or (II) feature excellent thermal stability, and compounds having a molar mass of less than about 1200 g/mol have good sublimability.

9. Compounds, oligomers, polymers and dendrimers having structures of formula (I) and/or (II) have excellent glass film formation.

10. Compounds, oligomers, polymers and dendrimers having structures of formula (I) and/or (II) form very good films from solutions.

These abovementioned advantages are not accompanied by a deterioration in the further electronic properties.

The present invention further provides for the use of a compound of the invention and/or an oligomer, polymer or dendrimer of the invention in an electronic device as hole injection material, hole transport material (HTM), hole blocker material (HBM), electron transport material (ETM), electron injection material, electron blocker material and/or emitter material, for example as triplet emitter material (TTM) or blue singlet emitter (SEB).

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example from a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is Illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

General Preparation Method:
Reaction of Monoaldehyde with Monoamine and Monoolefin

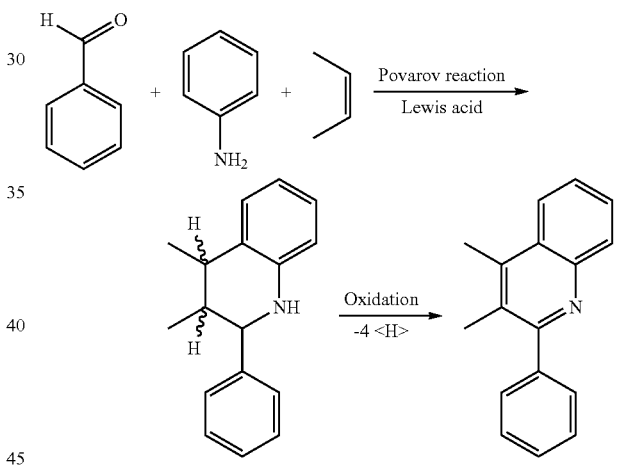

To a well-stirred mixture of 500 mmol of the arylamine, 550 mmol of the arylaldehyde, 1 mol of the activated olefin and 1300 mL of dichloromethane are added 100 mmol of the Lewis acid, and then the mixture is heated under reflux for 40 h. After cooling, the reaction mixture is washed twice with 400 mL each time of water, the organic phase is dried over magnesium sulfate and then the dichloromethane is removed under reduced pressure. The residue is taken up in 1000 mL of o-dichlorobenzene, 5 mol of manganese dioxide are added and the mixture is heated under reflux on a water separator for 16 h. After cooling, 1000 mL of ethyl acetate are added, the manganese dioxide is filtered off with suction through a Celite layer, the manganese dioxide is washed with 1000 mL of ethyl acetate and the combined filtrates are freed of the solvents under reduced pressure. The residue is recrystallized and finally freed of low boilers and nonvolatile secondary components by fractional sublimation (p about $10^{-4}$-$10^{-6}$ mbar, T about 150-400° C.). Compounds having a molar mass greater than about 1200 g/mol are preferably freed of solvent residues by heat treatment under high vacuum.

Example A1

7,8,9,10-Tetrahydro-7,10-methano-6-phenylphenanthridine

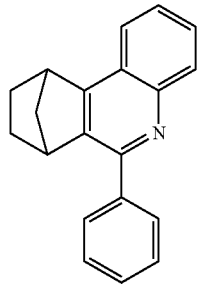 [SMILES: c1ccc(-c2nc3ccccc3c3c2C2CCC3C2)cc1]

If polyfunctional starting materials are used, the stoichiometry is adjusted correspondingly.

To a well-stirred mixture of 46.6 g (500 mmol) of aniline [62-63-3], 58.4 g (550 mmol) of benzaldehyde [100-52-7], 94.2 g (1 mol) of norbornene [498-66-8] and 1300 mL of dichloromethane are added dropwise 14.2 g (100 mmol) of boron trifluoride etherate [60-29-7], and then the mixture is heated under reflux for 40 h. After cooling, the reaction mixture is washed twice with 400 mL each time of water, the organic phase is dried over magnesium sulfate and then the dichloromethane is removed under reduced pressure. The residue is taken up in 1000 mL of o-dichlorobenzene, 435 g (5 mol) of manganese dioxide are added and the mixture is heated under reflux on a water separator for 16 h. After cooling, 1000 mL of ethyl acetate are added, the manganese dioxide is filtered off with suction through a Celite layer, the manganese dioxide is washed with 1000 mL of ethyl acetate and the combined filtrates are freed of the solvents under reduced pressure. The residue is recrystallized twice from cyclohexane and finally freed of low boilers and nonvolatile secondary components by fractional sublimation (p about $10^{-4}$-$10^{-5}$ mbar, T about 230° C.). Yield: 76.0 g (280 mmol), 56%; purity: about 99.5% by $^1$H NMR.

In an analogous manner, it is possible to prepare the following compounds:

| Ex. | Reactants | Product | Yield |
|---|---|---|---|
| Type A: Monoaldehyde + monoamine + monoolefin ||||

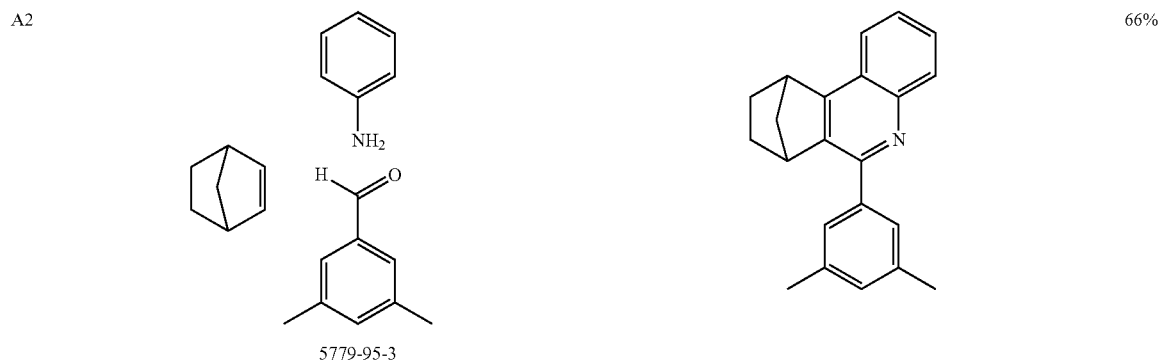

A2, 66%

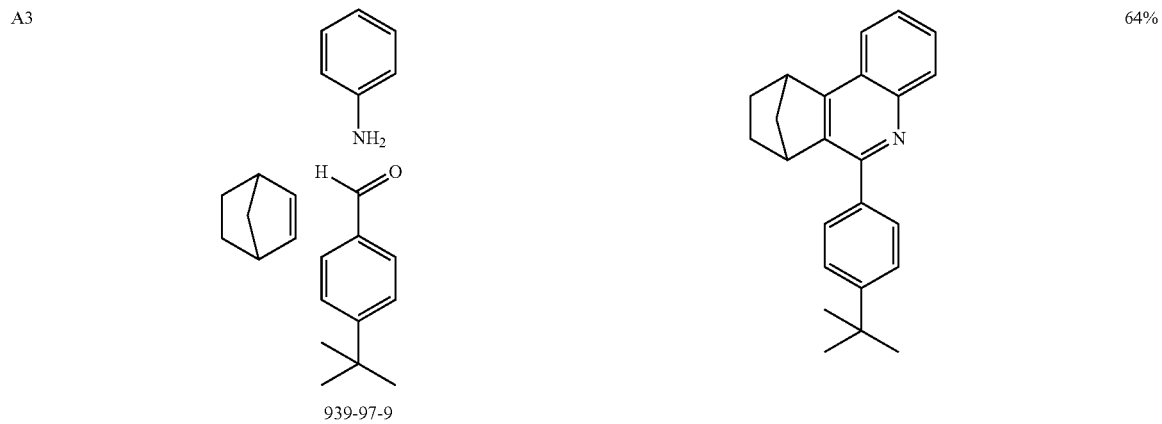

A3, 64%

-continued
| Ex. | Reactants | Product | Yield |
|---|---|---|---|
| A4 | 106-49-0 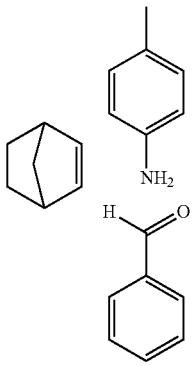 | 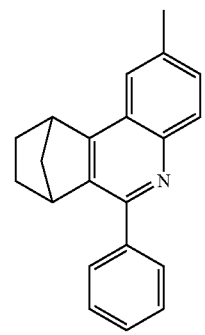 [SMILES: Cc1ccc2nc(-c3ccccc3)c3c(c2c1)C1CCC3C1] | 56% |
| A5 | 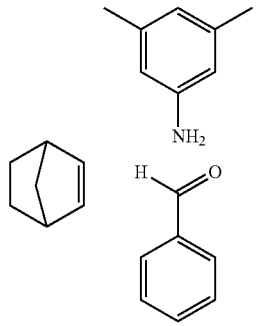 100-52-7 | 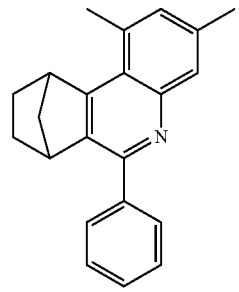 [SMILES: Cc1cc(C)c2c3c(c(-c4ccccc4)nc2c1)C1CCC3C1] | 58% |
| A6 | 769-92-6 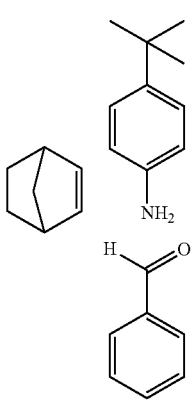 | 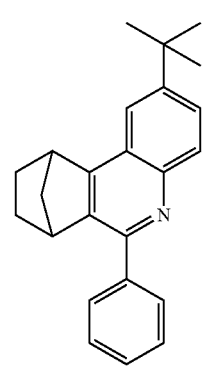 [SMILES: CC(C)(C)c1ccc2nc(-c3ccccc3)c3c(c2c1)C1CCC3C1] | 61% |

-continued
| Ex. | Reactants | Product | Yield |
|---|---|---|---|
| A7 | 92-67-1 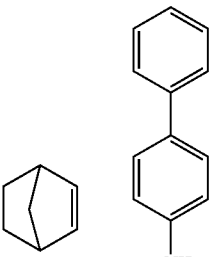 | 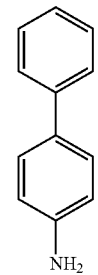 | 63% |
| A8 | 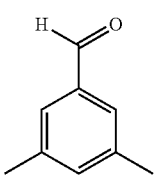 66-99-9 | 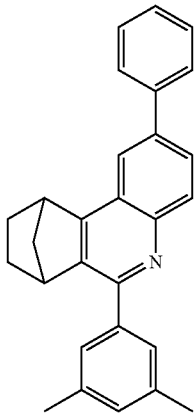 [SMILES: Cc1cc(C)cc(-c2nc3ccc(-c4ccccc4)cc3c3c2C2CCC3C2)c1] | 58% |
| A9 | 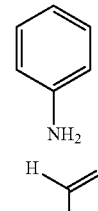 848300-71-8 |  | 55% |

US 10,205,106 B2
| Ex. | Reactants | Product | Yield |
|---|---|---|---|
| A10 | 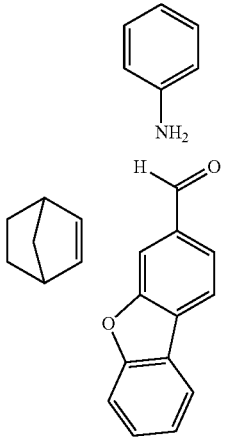 51818-91-8 | 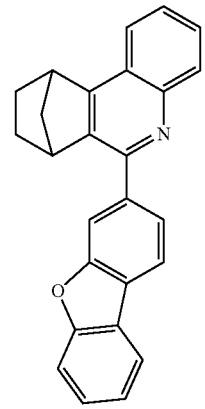 [SMILES: c1ccc2c3c(c(-c4ccc5c(c4)oc4ccccc45)nc2c1)C1CCC3C1] | 60% |
| A11 | 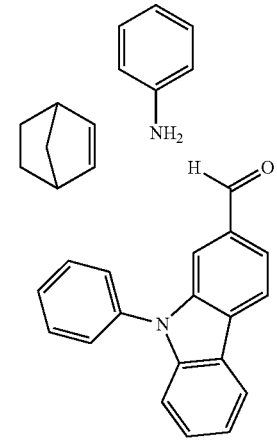 1353684-87-3 | 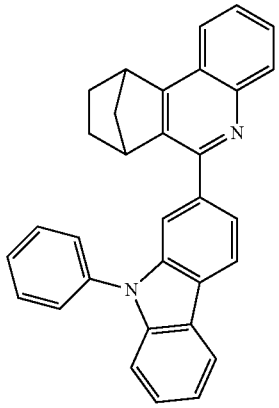 [SMILES: c1ccc(-n2c3ccccc3c3ccc(-c4nc5ccccc5c5c4C4CCC5C4)cc32)cc1] | 34% |
| A12 | 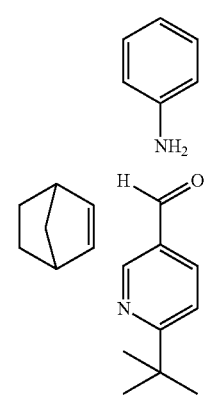 391900-69-9 | 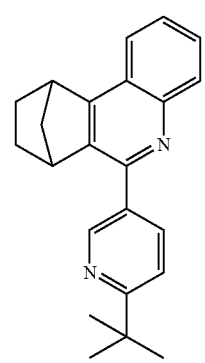 [SMILES: CC(C)(C)c1ccc(-c2nc3ccccc3c3c2C2CCC3C2)cn1] | 69% |

-continued
| Ex. | Reactants | Product | Yield |
|---|---|---|---|
| A13 | 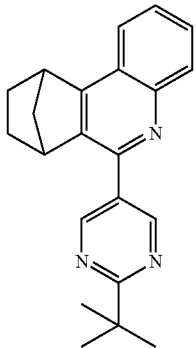 [SMILES: CC(C)(C)c1ncc(-c2nc3ccccc3c3c2C2CCC3C2)cn1] 104461-06-5 | 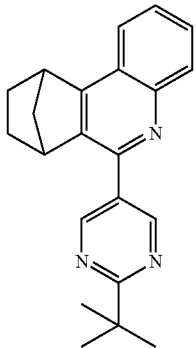 [SMILES: CC(C)(C)c1ncc(-c2nc3ccccc3c3c2C2CCC3C2)cn1] | 67% |
| A14 | 39919-70-5 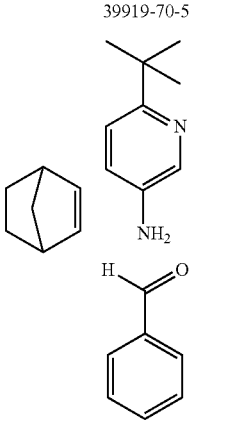 | 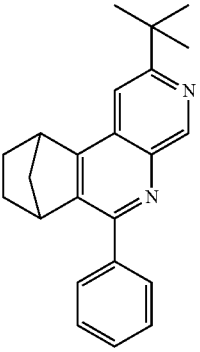 [SMILES: CC(C)(C)c1cc2c3c(c(-c4ccccc4)nc2cn1)C1CCC3C1] | 23% |
| | | 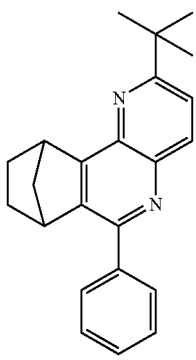 [SMILES: CC(C)(C)c1ccc2nc(-c3ccccc3)c3c(c2n1)C1CCC3C1] Chromatographic separation of the regioisomers | 17% |

-continued
| Ex. | Reactants | Product | Yield |
|---|---|---|---|
| A15 | 59950-55-9 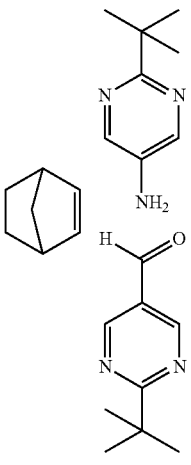 | 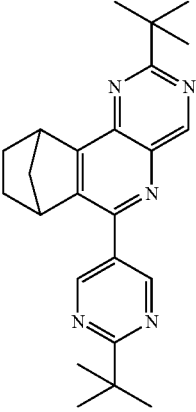 | 50% |
| A16 | 6541-60-2 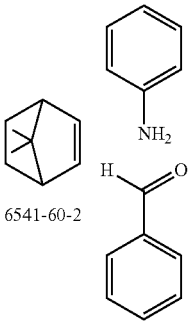 | 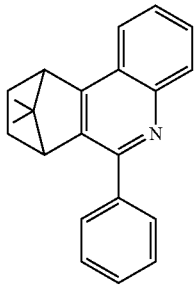 [SMILES: CC1(C)C2CCC1c1c2c(-c2ccccc2)nc2ccccc12] | 48% |
| A17 | 4453-90-1 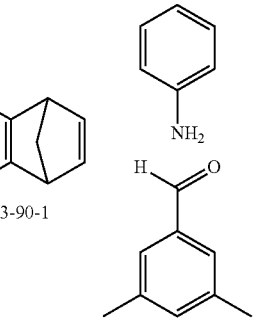 | 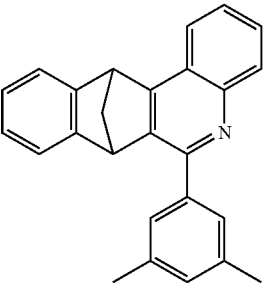 [SMILES: Cc1cc(C)cc(-c2nc3ccccc3c3c2C2CC3c3ccccc32)c1] | 68% |
| A18 | 6705-50-6 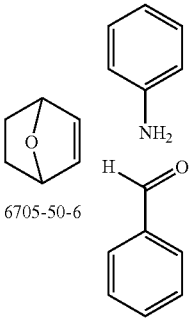 | 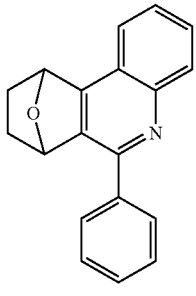 [SMILES: c1ccc(-c2nc3ccccc3c3c2C2CCC3O2)cc1] | 45% |

| Ex. | Reactants | Product | Yield |
|---|---|---|---|
| A19 | 95-64-7<br>573-57-9<br> |  | 65% |
| A20 | 1204-60-0<br>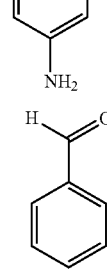 | 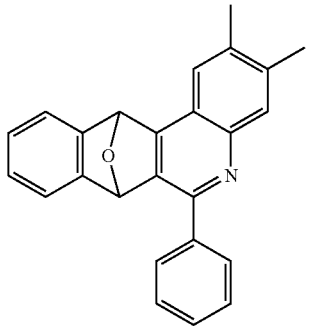 [SMILES: Cc1cc2nc(-c3ccccc3)c3c(c2cc1C)C1OC3c2ccccc21] | 54% |
| A21 | 139266-08-3<br>4521-30-6<br> | 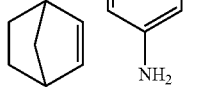 | 38% |

-continued
| Ex. | Reactants | Product | Yield |
|---|---|---|---|
| A22 | 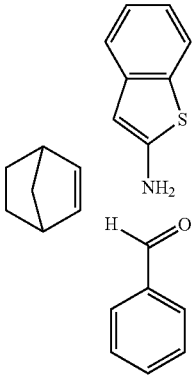 | 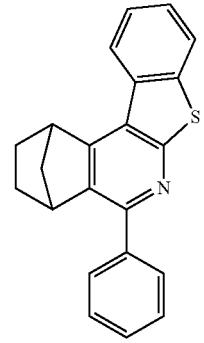 [SMILES: c1ccc(-c2nc3sc4ccccc4c3c3c2C2CCC3C2)cc1] | 34% |
| A23 | 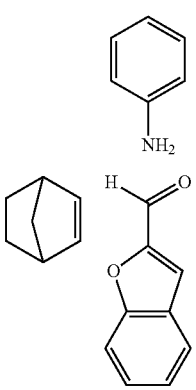<br>4265-16-1 | 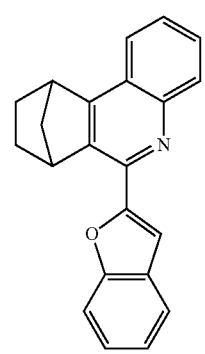 [SMILES: c1ccc2oc(-c3nc4ccccc4c4c3C3CCC4C3)cc2c1] | 36% |
| A24 | 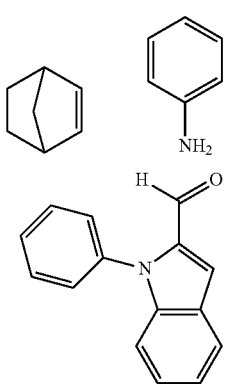<br>343238-30-2 | 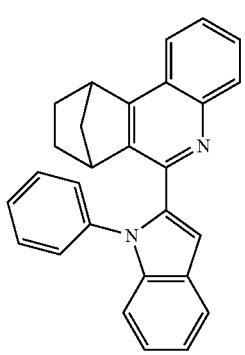 [SMILES: c1ccc(-n2c(-c3nc4ccccc4c4c3C3CCC4C3)cc3ccccc32)cc1] | 28% |

-continued
| Ex. | Reactants | Product | Yield |
|---|---|---|---|
| A25 | 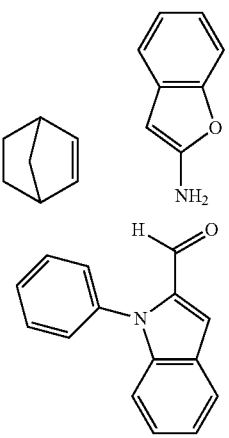 | 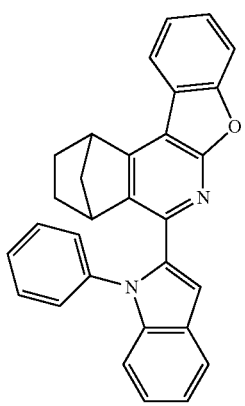 [SMILES: c1ccc(-n2c(-c3nc4oc5ccccc5c4c4c3C3CCC4C3)cc3ccccc32)cc1] | 32% |
| A26 | 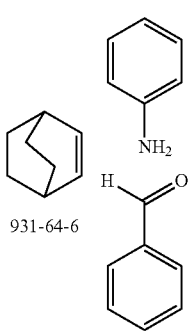 931-64-6 | 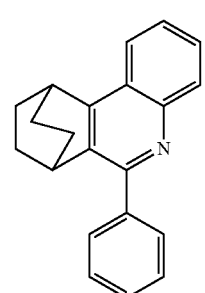 | 25% |
| A27 | 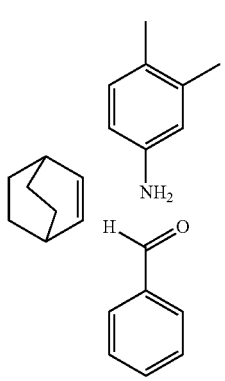 | 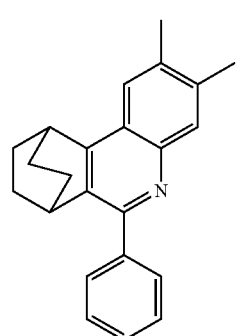 | 23% |
| A28 | 134-32-7 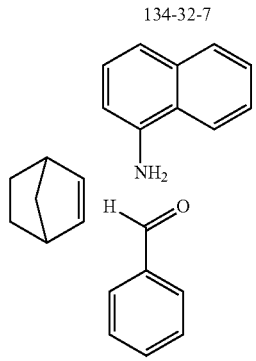 | 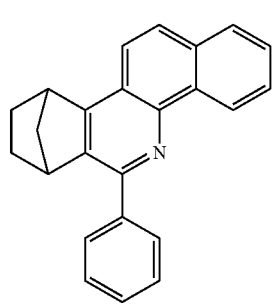 [SMILES: c1ccc(-c2nc3c(ccc4ccccc43)c3c2C2CCC3C2)cc1] | 34% |

-continued

| Ex. | Reactants | Product | Yield |
|---|---|---|---|
| A29 | 91-59-8 | | 45% |
| A30 | 124575-66-2 | | 46% |
| A31 | | | 50% |

| Ex. | Reactants | Product | Yield |
|---|---|---|---|
| A32 | 578-66-5 | | 53% |
| A33 | 61049-1 | | 33% |
| A34 | 2876-22-4 | | 28% |
| A35 | 613-13-8 | | 23% |

-continued

| Ex. | Reactants | Product | Yield |
|---|---|---|---|
| A36 | 21850-03-3 | | 30% |
| A37 | 974-73-9 | | 46% |
| A38 | | | 47% |

-continued

| Ex. | Reactants | Product | Yield |
|---|---|---|---|
| A39 | 1606-67-3 | | 51% |
| A40 | 220955-80-6 | | 49% |
| A41 | 105-07-7 | | 47% |

US 10,205,106 B2
-continued
| Ex. | Reactants | Product | Yield |
|---|---|---|---|
| A42 | 1732-23-6 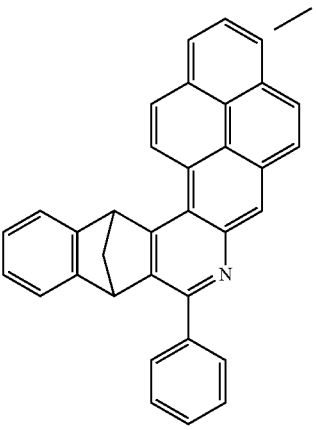 | 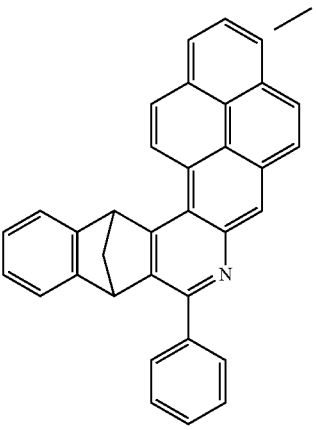 | 44% |
| A43 | 20492-13-1 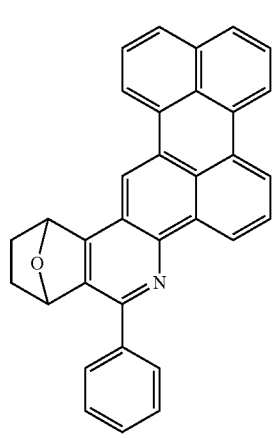 [SMILES: c1ccc(-c2nc3c(cc4c5cccc6cccc(c7cccc3c74)c65)c3c2C2CCC3O2)cc1] | 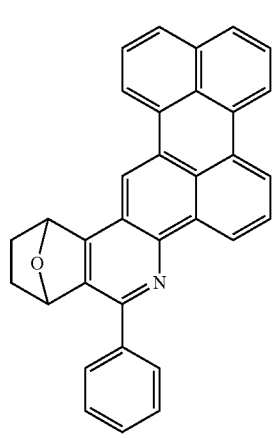 [SMILES: c1ccc(-c2nc3c(cc4c5cccc6cccc(c7cccc3c74)c65)c3c2C2CCC3O2)cc1] | 43% |
| A44 | 384362-01-0 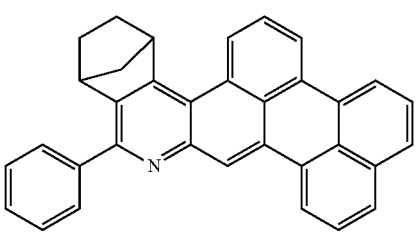 [SMILES: c1ccc(-c2nc3cc4c5cccc6cccc(c7cccc(c3c3c2C2CCC3C2)c74)c65)cc1] | 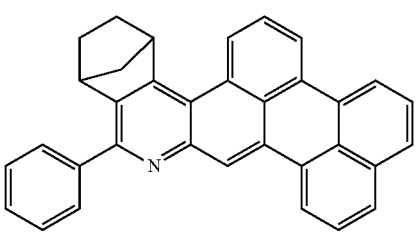 [SMILES: c1ccc(-c2nc3cc4c5cccc6cccc(c7cccc(c3c3c2C2CCC3C2)c74)c65)cc1] | 38% |

-continued
| Ex. | Reactants | Product | Yield |
|---|---|---|---|
| A45 | 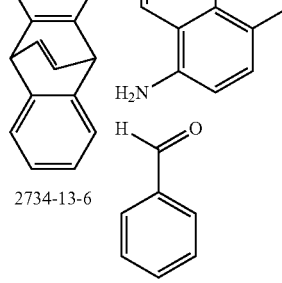 | 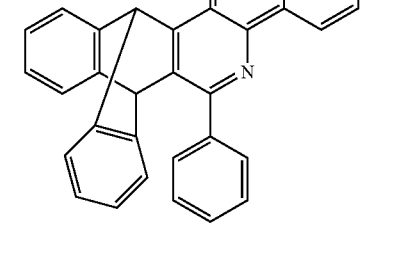 | 45% |
| A46 | 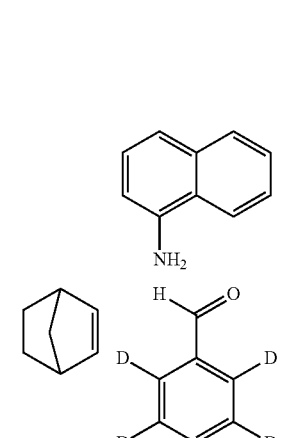 | 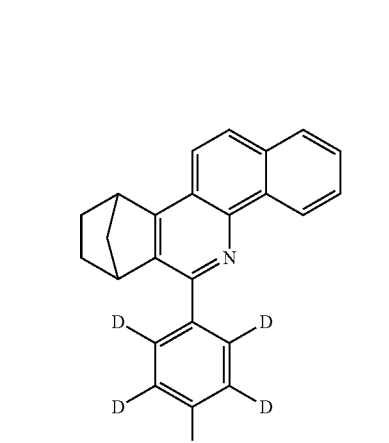 | 47% |
| A47 | 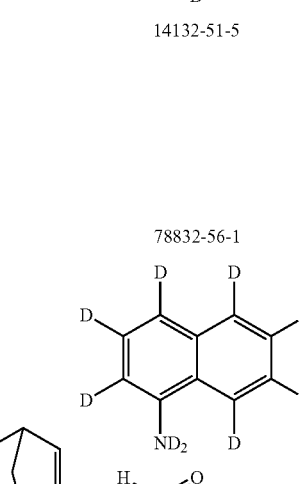 | 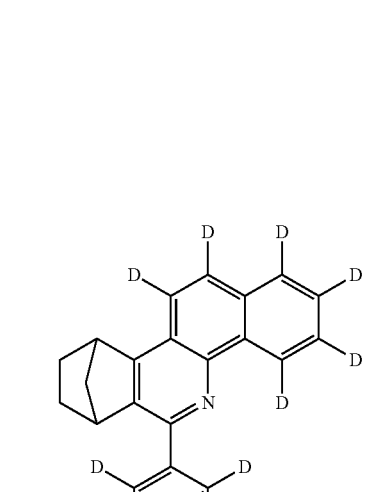 | 48% |

-continued
| Ex. | Reactants | Product | Yield |
|---|---|---|---|
| A48 | 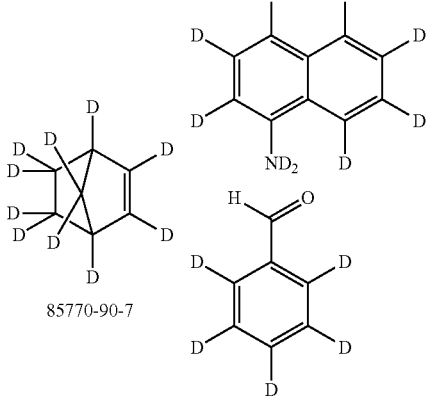 85770-90-7 | 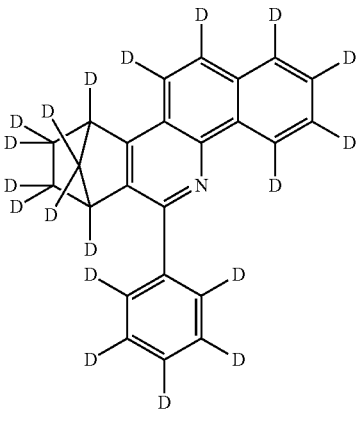 [SMILES: [2H]c1c([2H])c([2H])c(-c2nc3c(c([2H])c([2H])c4c([2H])c([2H])c([2H])c([2H])c43)c3c2C2([2H])C([2H])([2H])C([2H])([2H])C3([2H])C2([2H])[2H])c([2H])c1[2H]] | 48% |
| A49 | 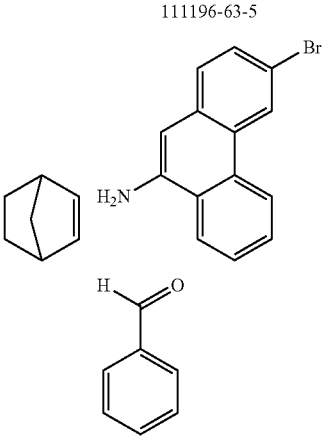 111196-63-5 | 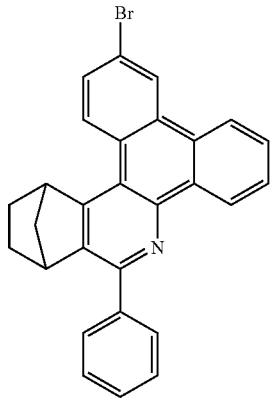 [SMILES: Brc1ccc2c(c1)c1ccccc1c1nc(-c3ccccc3)c3c(c21)C1CCC3C1] | 50% |
| A50 | 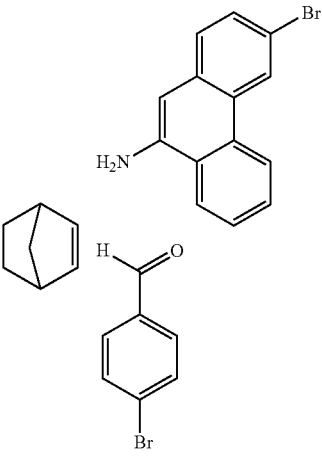 1122-91-4 | 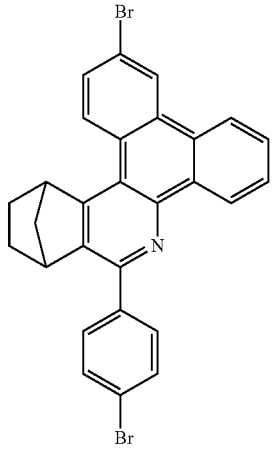 [SMILES: Brc1ccc(-c2nc3c4ccccc4c4cc(Br)ccc4c3c3c2C2CCC3C2)cc1] | 49% |

-continued
| Ex. | Reactants | Product | Yield |
|---|---|---|---|
| A51 | 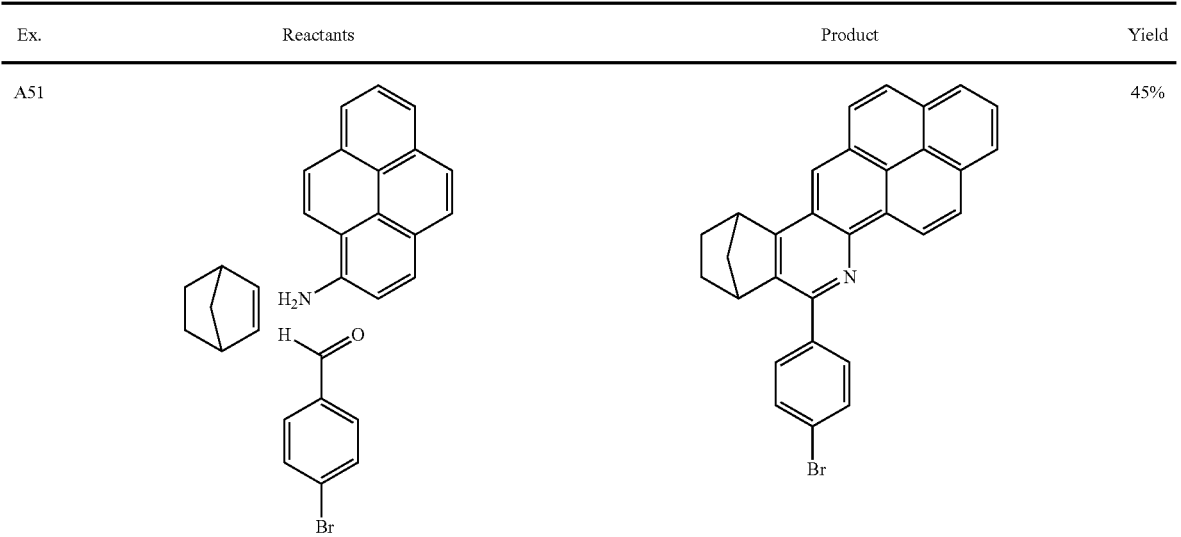 | | 45% |
| A52 | 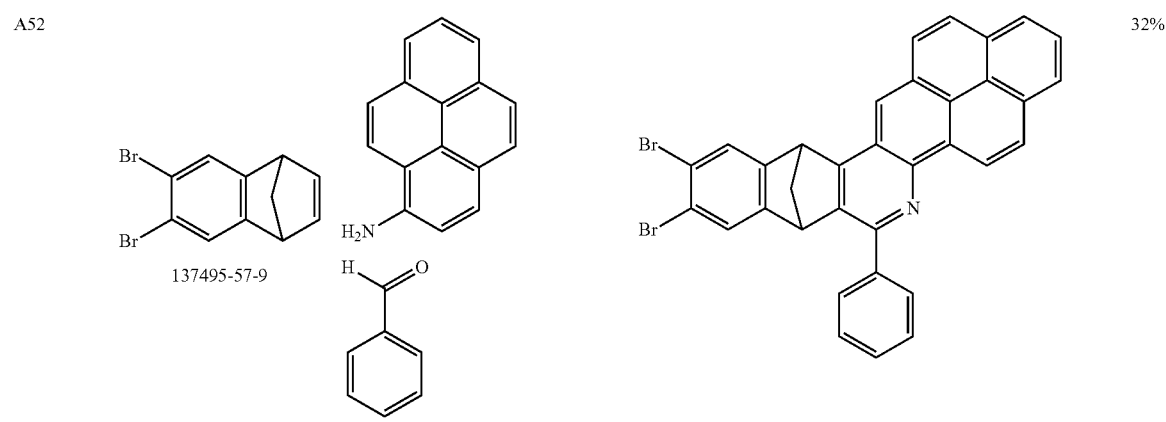 | | 32% |
Type B: Dialdehyde + monoamine + monoolefin
| B1 | 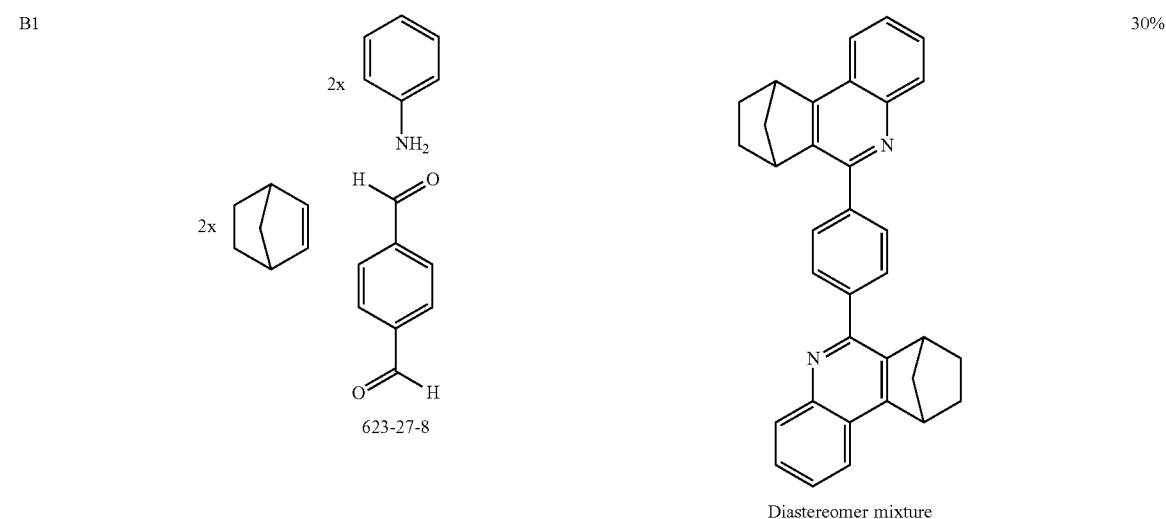 | | 30% |
Diastereomer mixture -continued
| Ex. | Reactants | Product | Yield |
|---|---|---|---|
| B2 | 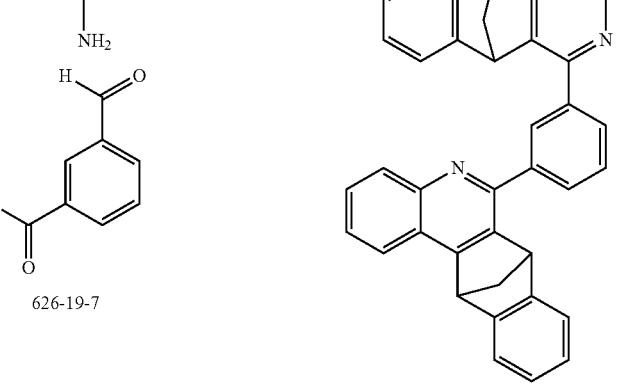 2x <br> 2x aniline <br> 626-19-7 (isophthalaldehyde) |  <br> Diastereomer mixture | 33% |
| B3 | 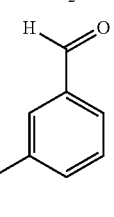 <br> 2437-75-4 <br> 2x aniline <br> terephthalaldehyde |  | 30% |
| B4 | 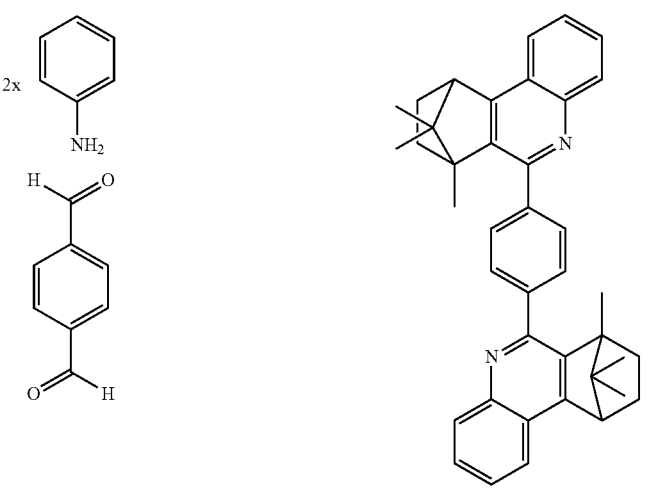 <br> 2x aniline <br> 7141-15-3 |  | 28% |

-continued
| Ex. | Reactants | Product | Yield |
|---|---|---|---|
| B5 | 2x norbornene; 2x 90-41-5 (2-aminobiphenyl); 252338-01-5 (pyrene-1,6-dicarbaldehyde) 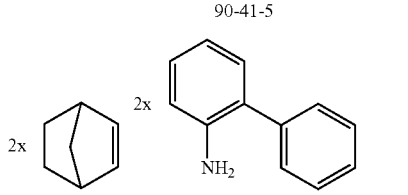 | 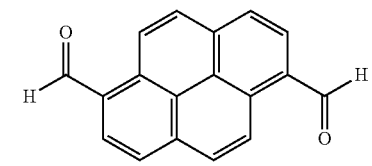 Diastereomer mixture | 35% |
| B6 | 2x norbornene; 2x 8-aminoquinoline; 856014-12-5 (spirobifluorene dialdehyde) 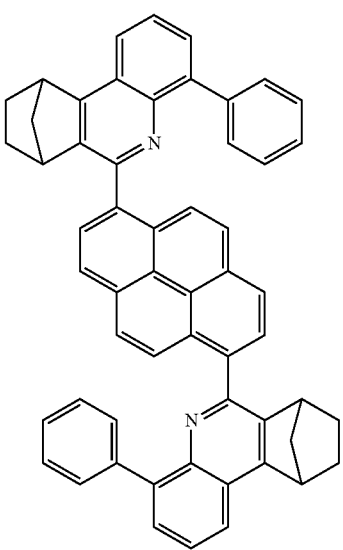 [SMILES: c1ccc(-c2cccc3c4c(c(-c5ccc6ccc7c(-c8nc9c(-c%10ccccc%10)cccc9c9c8C8CCC9C8)ccc8ccc5c6c87)nc23)C2CCC4C2)cc1] | 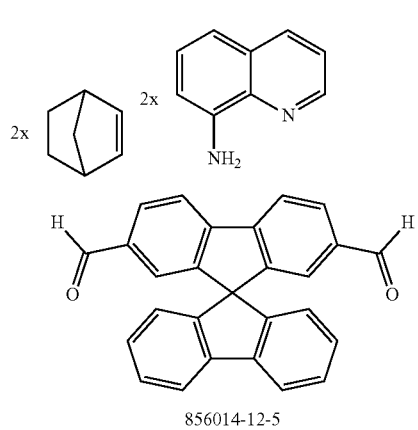 Diastereomer mixture | 23% |

-continued
| Ex. | Reactants | Product | Yield |
|---|---|---|---|
| B7 | 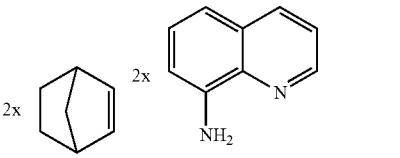 | 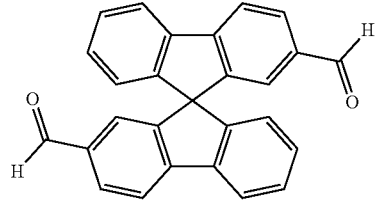 | 25% |
Diastereomer mixture
Type C: Trialdehyde + monoamine + monoolefin
| C1 | 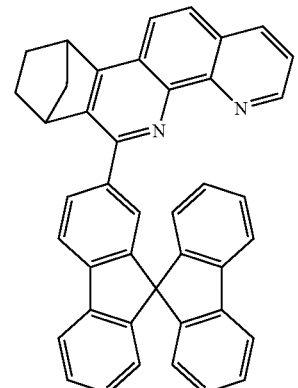 | 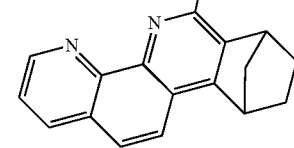 | 19% |
Diastereomer mixture
Type D: Monoaldehyde + diamine + monoolefin -continued
| Ex. | Reactants | Product | Yield |
|---|---|---|---|
| D1 | 106-50-3 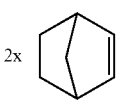 | 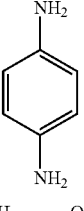<br>Diastereomer mixture | 27% |
| D2 | 108-45-2 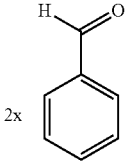 | 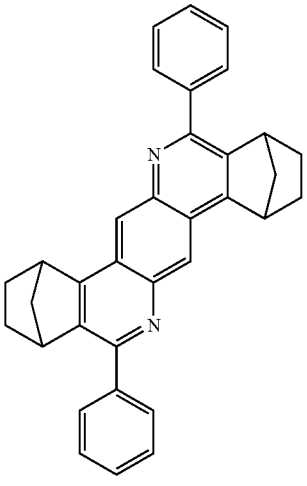 [SMILES: c1ccc(-c2nc3cc4c5c(c(-c6ccccc6)nc4cc3c3c2C2CCC3C2)C2CCC5C2)cc1]<br>Diastereomer mixture | 24% |
| D3 | 9554-5 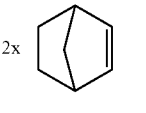 | 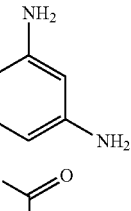<br>Diastereomer mixture | 30% |

-continued
| Ex. | Reactants | Product | Yield |
|---|---|---|---|
| D4 | 2243-62-1 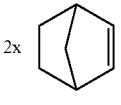 | 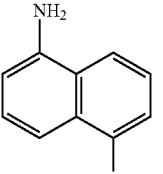 Diastereomer mixture | 29% |
| D5 | 64-761-26-8 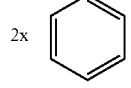 | 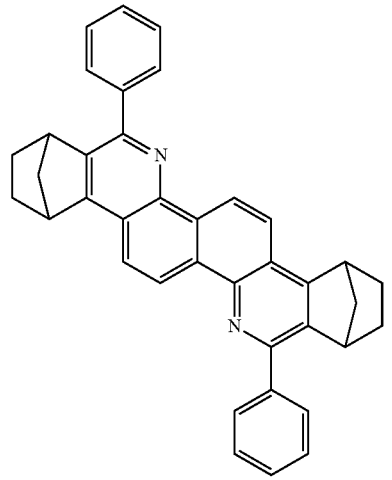 [SMILES: c1ccc(-c2nc3c(ccc4c3ccc3c5c(c(-c6ccccc6)nc34)C3CCC5C3)c3c2C2CCC3C2)cc1] Diastereomer mixture | 24% |
| D6 | 153354-32-6 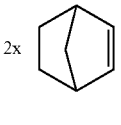 1204-60-0 | 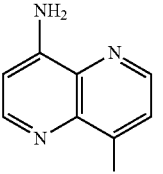 | 20% |

-continued
| Ex. | Reactants | Product | Yield |
|---|---|---|---|
| | | Diastereomer mixture | |
| D7 | 79015-49-9 | 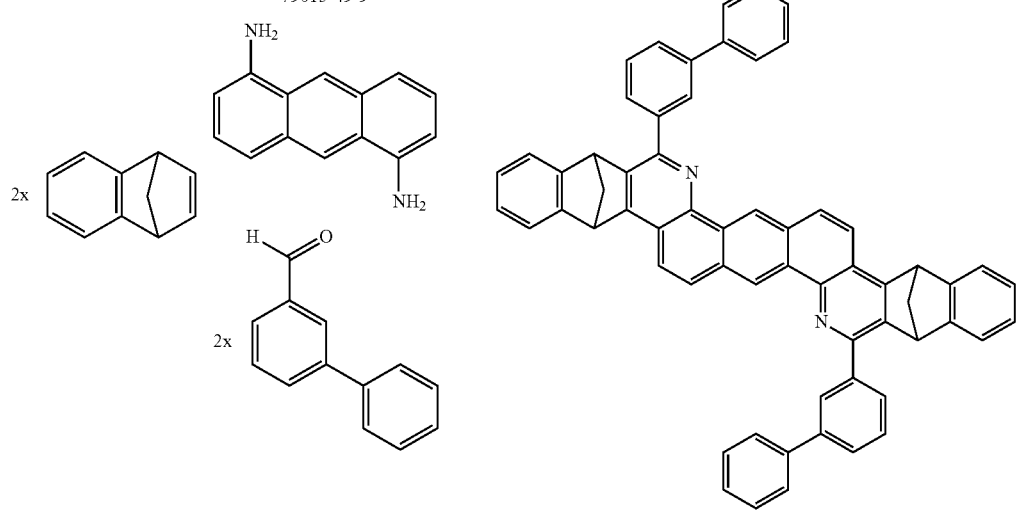 | 26% |
| | | Diastereomer mixture | |
| D8 | | 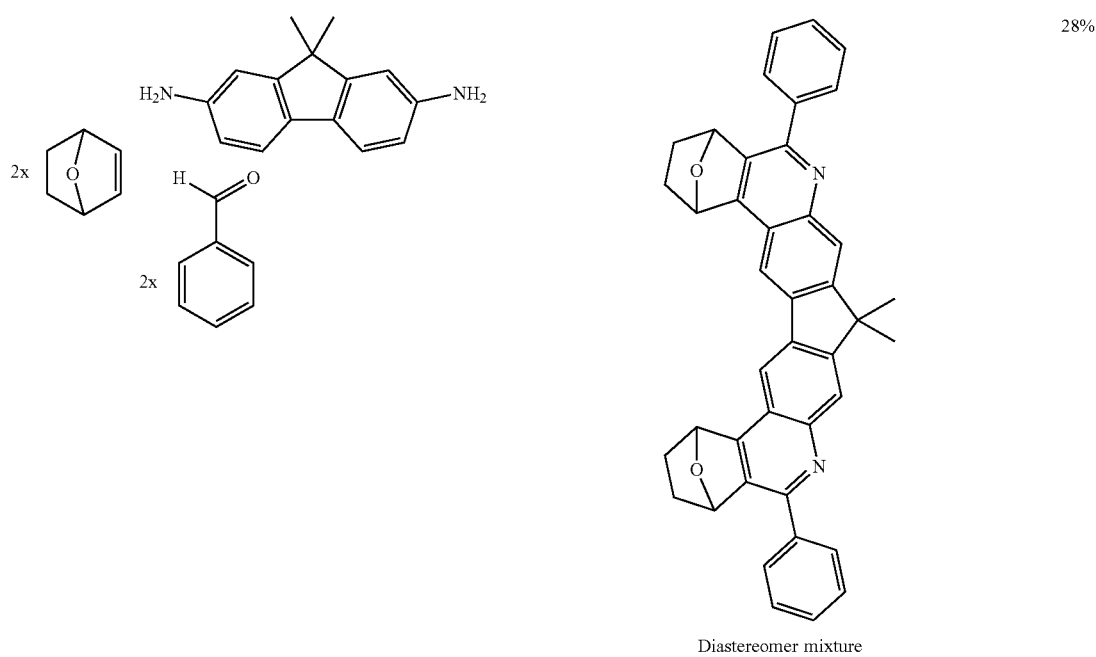 | 28% |
| | | Diastereomer mixture | |

| Ex. | Reactants | Product | Yield |
|---|---|---|---|
| D9 | | | 25% |
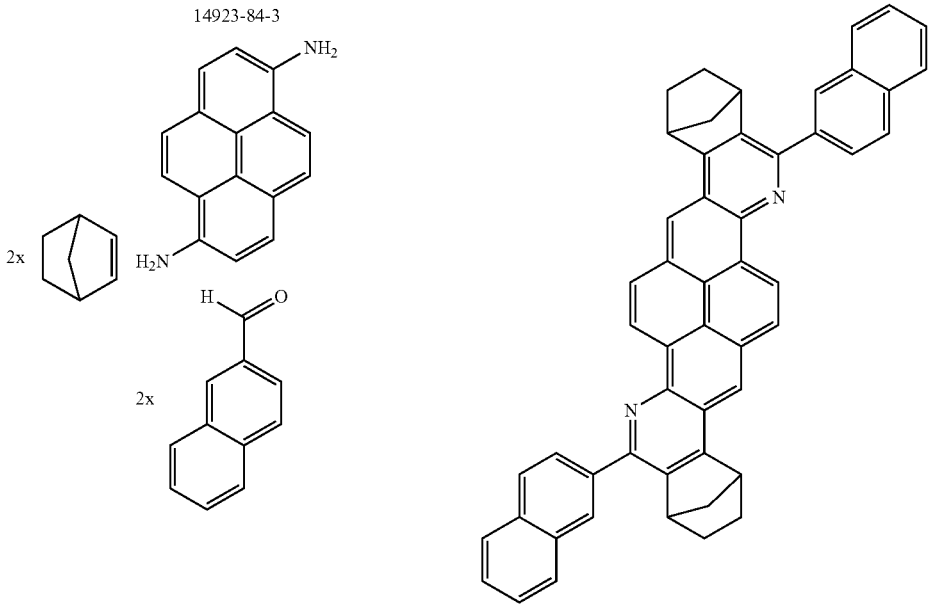
Diastereomer mixture
Type E: Monoaldehyde + triamine + monoolefin
| E1 | | | 19% |
|---|---|---|---|
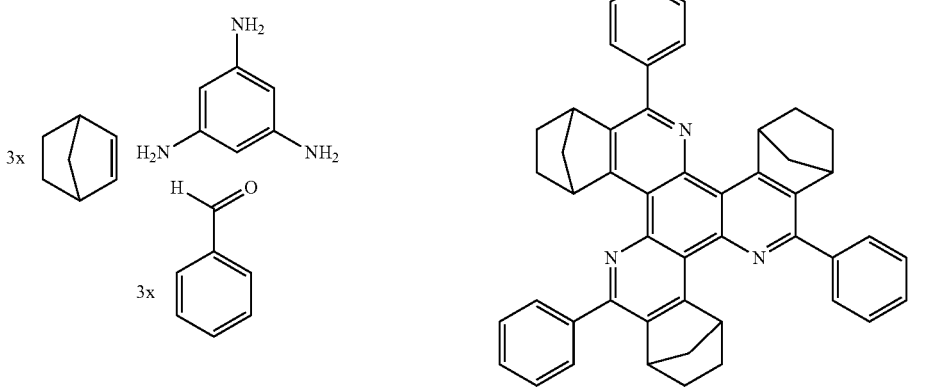
Diastereomer mixture
Type F: Monoaldehyde + monoamine + diolefin
| F1 | | | 26% |
|---|---|---|---|
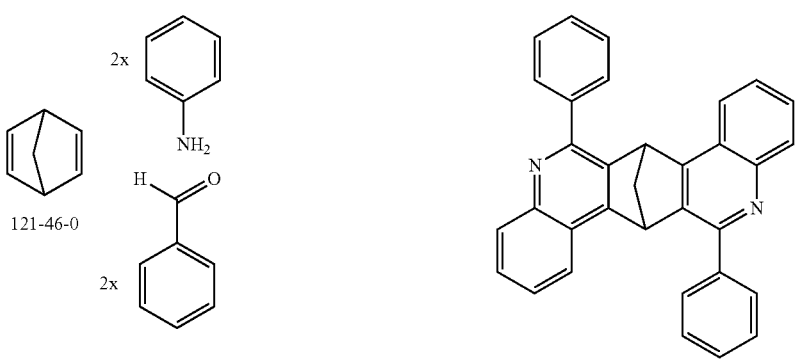

| Ex. | Reactants | Product | Yield |
|---|---|---|---|
| F2 | 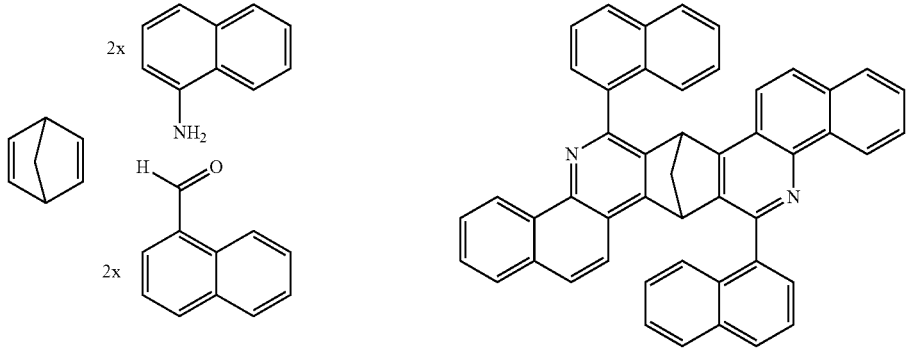 | 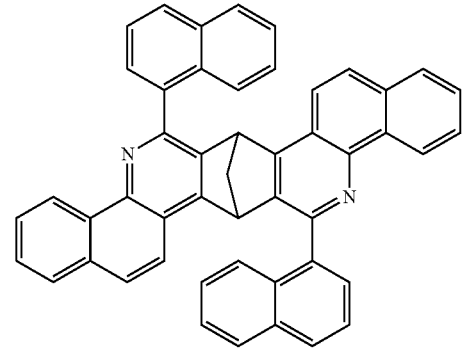 [SMILES: c1ccc2c(-c3nc4c(ccc5ccccc54)c4c3C3CC4c4c(-c5cccc6ccccc56)nc5c(ccc6ccccc65)c43)cccc2c1] | 25% |
| F3 | 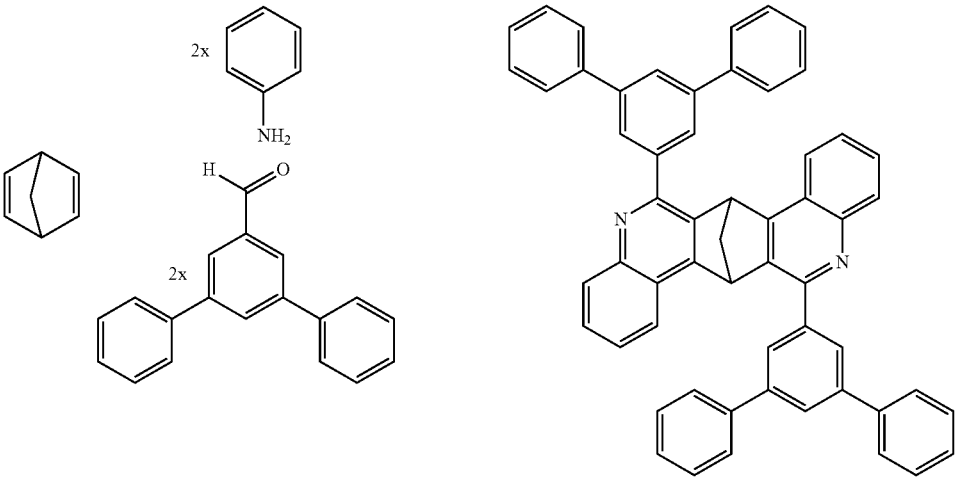 | 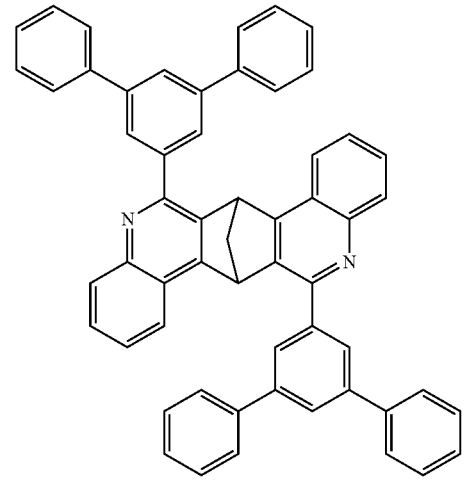 [SMILES: c1ccc(-c2cc(-c3ccccc3)cc(-c3nc4ccccc4c4c3C3CC4c4c(-c5cc(-c6ccccc6)cc(-c6ccccc6)c5)nc5ccccc5c43)c2)cc1] | 28% |
| F4 | 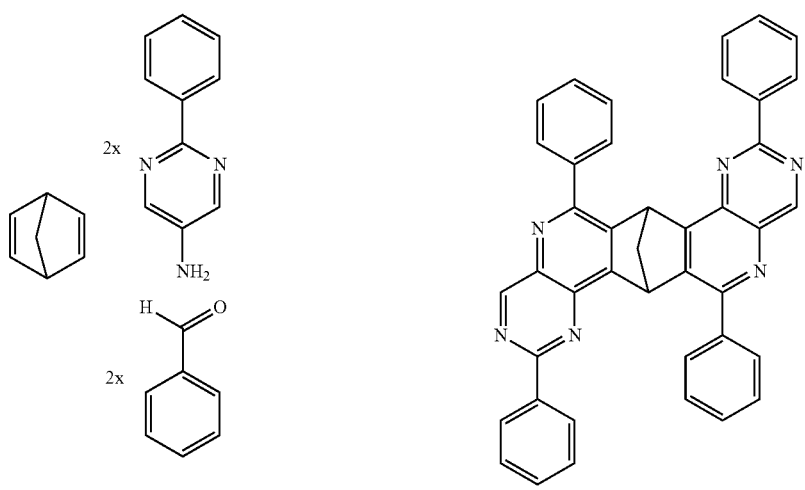 | 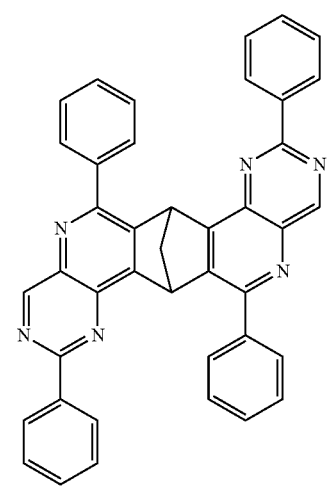 [SMILES: c1ccc(-c2ncc3nc(-c4ccccc4)c4c(c3n2)C2CC4c3c2c(-c2ccccc2)nc2cnc(-c4ccccc4)nc32)cc1] | 31% |

-continued
| Ex. | Reactants | Product | Yield |
|---|---|---|---|
| F5 | 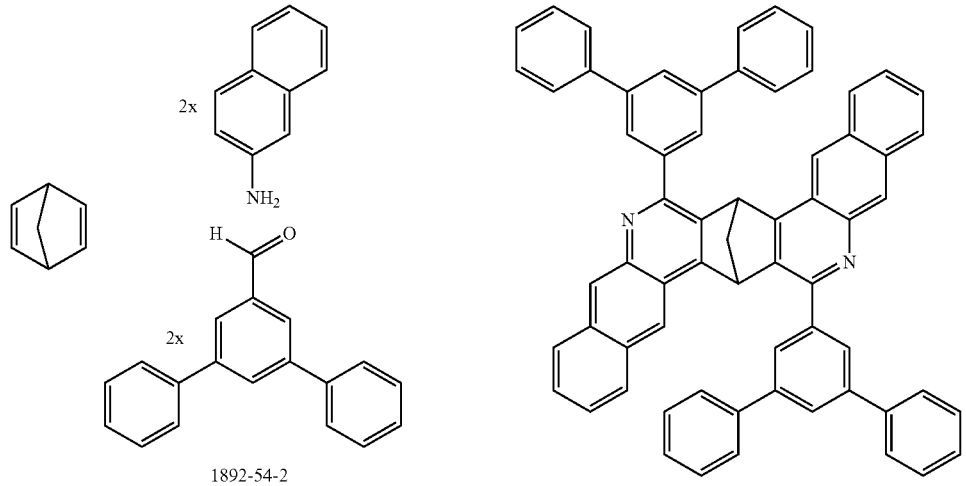 | | 20% |
| F6 | 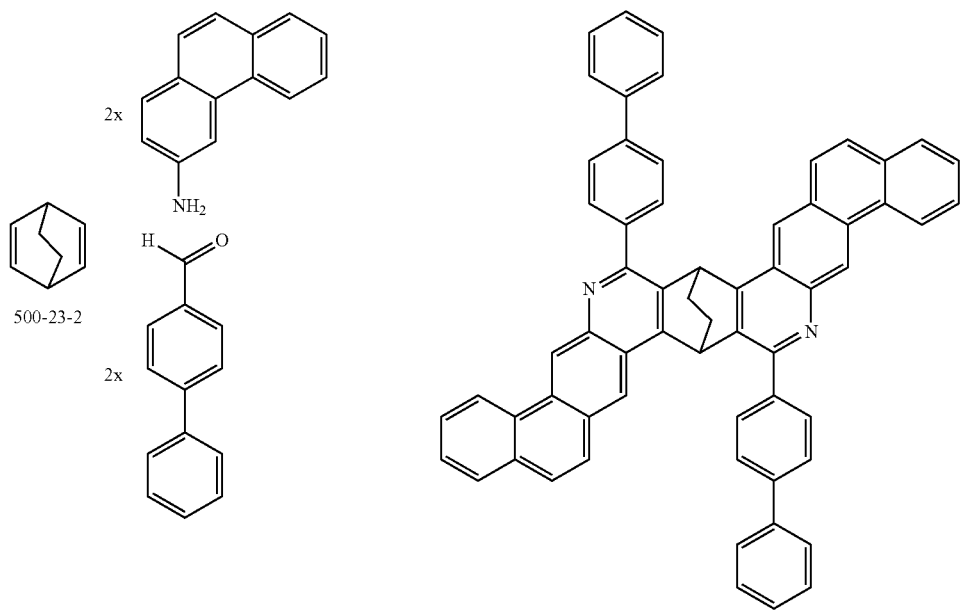 | | 25% |

| Ex. | Reactants | Product | Yield |
|---|---|---|---|
| F7 | 2x (phenanthren-2-amine); 7322-47-6; 2x (4-biphenylcarbaldehyde) 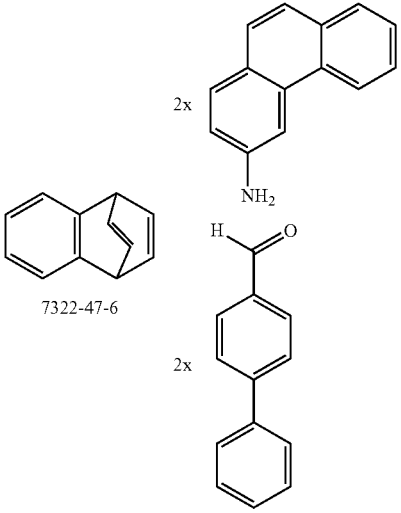 | 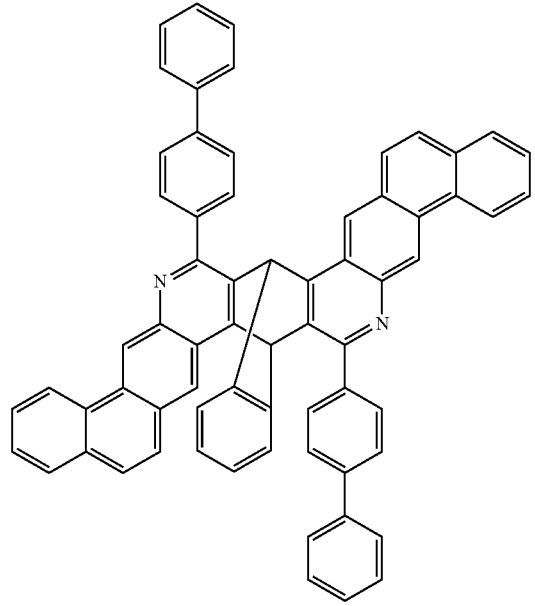 [SMILES: c1ccc(-c2ccc(-c3nc4cc5c(ccc6ccccc65)cc4c4c3C3c5ccccc5C4c4c(-c5ccc(-c6ccccc6)cc5)nc5cc6c(ccc7ccccc76)cc5c43)cc2)cc1] | 24% |
| Type G: Monoaldehyde + monoamine + triolefin ||||
|---|---|---|---|
| G1 | 2x aniline; 500-24-3; 2x benzaldehyde 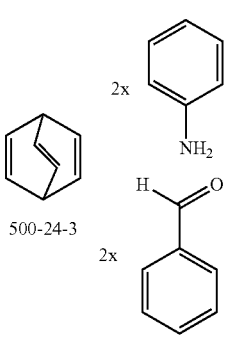 | 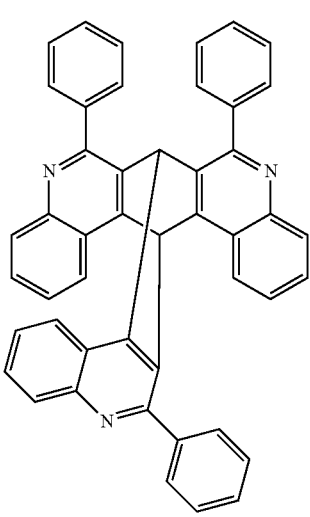 [SMILES: c1ccc(-c2nc3ccccc3c3c2C2c4c(c(-c5ccccc5)nc5ccccc45)C3c3c(-c4ccccc4)nc4ccccc4c32)cc1] | 13% |
The compounds of the A33 ff., B, D, D, E, F and G type may preferably find use as e-TMM, HBM, ETM, SMB and SEB.

Example A53

Functionalization of the Materials by Suzuki Coupling

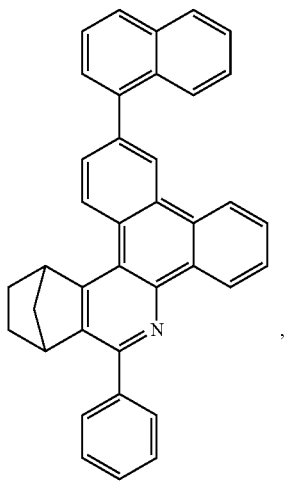 [SMILES: c1ccc(-c2nc3c4ccccc4c4cc(-c5cccc6ccccc56)ccc4c3c3c2C2CCC3C2)cc1]

,

A mixture of 22.5 g (50 mmol) of A49, 12.9 g (75 mmol) of 1-naphthylboronic acid, 31.8 g (150 mmol) of tripotassium phosphate, 224.5 mg (1 mmol) of palladium(II) acetate, 1.8 g (6 mmol) of tri-o-tolylphosphine, 200 mL of toluene, 50 mL of dioxane and 250 mL of water is heated under reflux with good stirring for 20 h. After cooling, the aqueous phase is removed, washed twice with 100 mL each time of water and once with 100 mL of sat. sodium chloride solution and then filtered through a Celite bed in order to remove palladium. After concentration, the residue is recrystallized five times from DMF and then fractionally sublimed twice under high vacuum (p about $10^{-5}$ mbar, T: 280-300° C.). Yield: 11.2 g (22.5 mmol), 45% of theory. Purity: 99.9% by HPLC.

In an analogous manner, it is possible to prepare the following compounds:

| Ex. | Bromide | Boronic acid | Product | Yield |
|---|---|---|---|---|
| A54 | A50 (Br-substituted) | 98-80-6 (4-bromophenyl-Ph, B(OH)₃) | | 64% |

| Ex. | Bromide Boronic acid | Product | Yield |
|---|---|---|---|
| A55 | A51 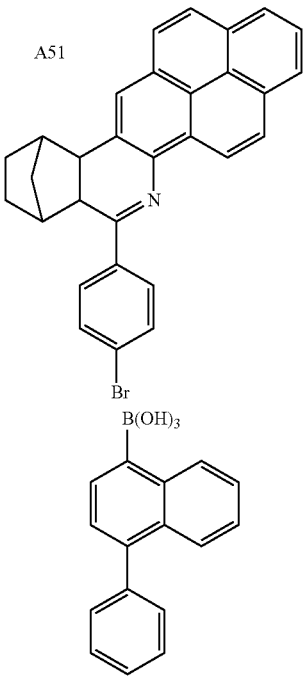 372521-91-0 | 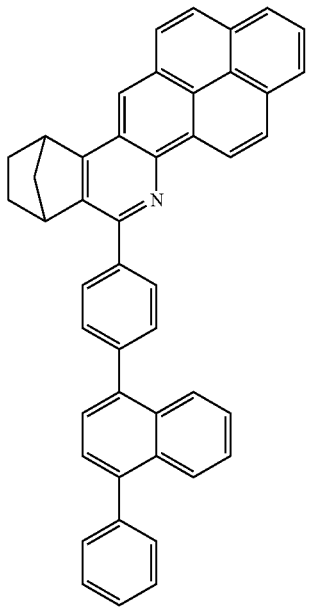 [SMILES: c1ccc(-c2ccc(-c3ccc(-c4nc5c(cc6ccc7cccc8ccc5c6c78)c5c4C4CCC5C4)cc3)c3ccccc23)cc1] | 74% |
| A56 | 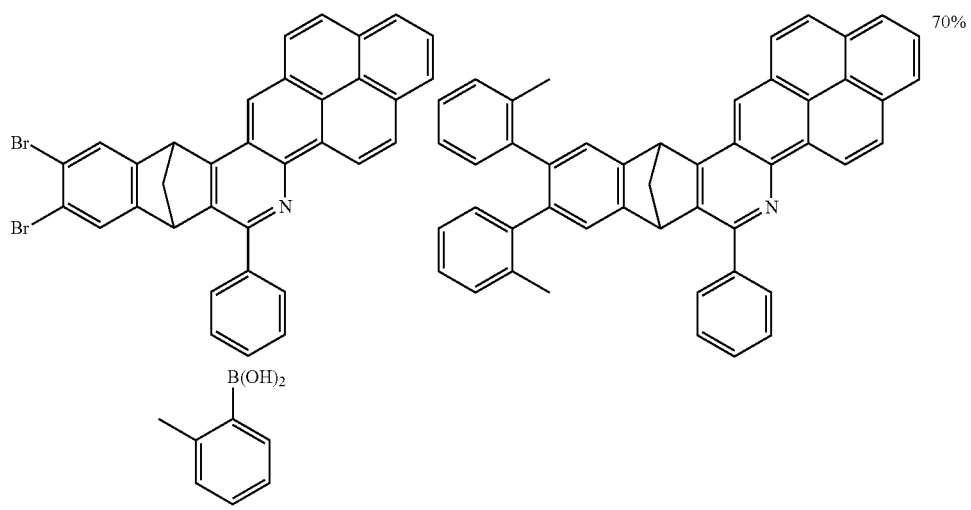 16419-60-6 | | 70% |

Example A57

Functionalization of the Materials by Buchwald Coupling

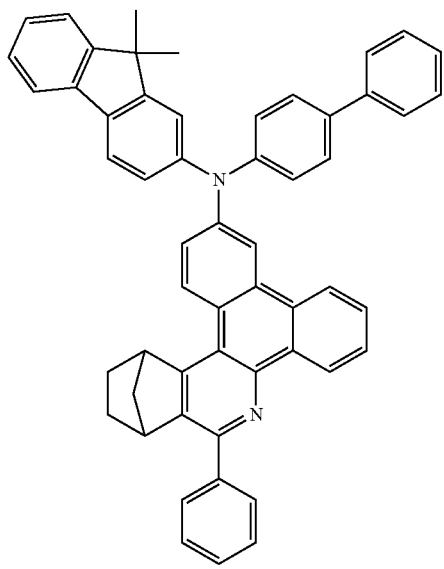 [SMILES: CC1(C)c2ccccc2-c2ccc(N(c3ccc(-c4ccccc4)cc3)c3ccc4c(c3)c3ccccc3c3nc(-c5ccccc5)c5c(c43)C3CCC5C3)cc21]

A mixture of 22.5 g (50 mmol) of A49, 22.6 g (60 mmol) of N-[1,1''-biphenyl]-4-yl-9,9-dimethyl-9H-fluorene [897671-69-1], 7.2 g (75 mmol) of sodium tert-butoxide, 224.5 mg (1 mmol) of palladium(II) acetate, 263 mg (1.3 mmol) of tri-tert-butylphosphine and 300 mL of toluene is heated under reflux with good stirring for 20 h. After cooling, the reaction mixture is washed twice with 100 mL each time of water and once with 100 mL of sat. sodium chloride solution and then filtered through a Celite bed in order to remove palladium. After concentration, the residue is recrystallized five times from DMF and then fractionally sublimed twice under high vacuum (p about $10^{-5}$ mbar, T: 300-310° C.). Yield: 14.3 g (19.5 mmol), 39% of theory. Purity: 99.9% by HPLC.

In an analogous manner, it is possible to prepare the following compounds:

| Ex. | Bromide | Amine/carbazole | Product | Yield |
|---|---|---|---|---|
| A58 | A50 25 mmol | 102113-98-4 | | 66% |

-continued

| Ex. | Bromide | Amine/carbazole | Product | Yield |
|---|---|---|---|---|
| A59 | A51 | 1257220-47-5 | | 54% |

Compound A1-A27 may find preferential use as bidentate chelate ligands for transition metals, for example iridium and platinum, and as electron-conducting triplex matrix material (eTMM) or electron transport material (ETM).

The compounds of the A28 ff., B, D, D, E, F and G type may preferably find use as electron-conducting triplex matrix material (e-TMM), hole blocker material (HBM), electron transport material (ETM), blue singlet material (SMB) and blue singlet emitter (SEB).

Example

Production of the OLEDs

1) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Glass plaques with structured ITO (50 nm, indium tin oxide) form the substrates to which the OLEDs are applied. The OLEDs basically have the following layer structure: substrate/hole transport layer 1 (HTL1) consisting of HTM doped with 3% NDP-9 (commercially available from Novaled), 20 nm/hole transport layer 2 (HTL2)/optional electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as M3:M2: $Ir(L1)_3$ (55%:35%:10%) mean here that the material M3 is present in the layer in a proportion by volume of 55%, M2 in a proportion of 35% and $Ir(L1)_3$ in a proportion of 10%. Analogously, the electron transport layer may also consist of a mixture of two materials. The exact structure of the OLEDs can be found in Table 1. The materials used for production of the OLEDs are shown in Table 4.

The OLEDs are characterized in a standard manner. For this purpose, the electroluminescence spectra, the power efficiency (measured in cd/A) and the voltage (measured at 1000 cd/m$^2$ in V) are determined from current-voltage-brightness characteristics (IUL characteristics). For selected experiments, the lifetime is determined. The lifetime is defined as the time after which the luminance has fallen from a particular starting luminance to a certain proportion. The figure LD50 means that the lifetime specified is the time at which the luminance has dropped to 50% of the starting luminance, i.e. from, for example, 1000 cd/m$^2$ to 500 cd/m$^=$. According to the emission color, different starting brightnesses are used. The values for the lifetime can be converted to a figure for other starting luminances with the aid of conversion formulae known to those skilled in the art. In this context, the lifetime for a starting luminance of 1000 cd/m$^2$ is a standard figure.

Use of Compounds of the Invention in OLEDs

The uses of the compounds of the invention include uses as HTM, TMM, ETM, HBM, SMB and SEB in OLEDs.

TABLE 1

| | | | Structure of the OLED | | |
|---|---|---|---|---|---|
| Ex. | HTL2 thickness | HTL-003 thickness | EML thickness | HBL thickness | ETL thickness |
| | | | Use as HTM | | |
| D-Vac 1 | HTM 220 nm | A57 10 nm | M1:M2:Ir-G (65%:30%:5%) 25 nm | — | ETM1:ETM2 (50%:50%) 20 nm |
| D-Vac 2 | HTM 220 nm | A58 10 nm | M1:M2:Ir-G (65%:30%:5%) 25 nm | — | ETM1:ETM2 (50%:50%) 20 nm |
| D-Vac 3 | HTM 220 nm | A57 10 nm | M1:M2:Ir-G (65%:30%:5%) 25 nm | A30 5 nm | ETM1:ETM2 (50%:50%) 20 nm |
| D-Vac 4 | HTM 220 nm | A57 10 nm | M1:M2:Ir-G (65%:30%:5%) 25 nm | HBM-Ref 5 nm | ETM1:ETM2 (50%:50%) 20 nm |
| | | | Use as TMM | | |
| D-Vac 5 | HTM 220 nm | — | A32:M2:Ir-G (65%:30%:5%) 25 nm | M1 10 nm | ETM1:ETM2 (50%:50%) 20 nm |
| D-Vac 5-Ref | HTM 220 nm | — | TMM-Ref:M2:Ir-G (65%:30%:5%) 25 nm | M1 10 nm | ETM1:ETM2 (50%:50%) 20 nm |
| D-Vac 6 | HTM 220 nm | — | A37:M2:Ir-R (65%:30%:5%) 30 nm | M1 10 nm | ETM1:ETM2 (50%:50%) 20 nm |
| D-Vac 7 | HTM 220 nm | — | B3:M2:Ir-R (60%:30%:10%) 30 nm | M1 10 nm | ETM1:ETM2 (50%:50%) 20 nm |
| D-Vac 8 | HTM 220 nm | — | B3:M2:Ir-R (60%:35%:5%) 30 nm | D3 10 nm | ETM1:ETM2 (50%:50%) 20 nm |
| D-Vac 9 | HTM 220 nm | — | M1:A59:Ir-R (60%:35%:5%) 30 nm | D3 10 nm | ETM1:ETM2 (50%:50%) 20 nm |
| D-Vac 10 | HTM 220 nm | — | F4:A59:Ir-R (60%:35%:5%) 30 nm | D3 10 nm | ETM1:ETM2 (50%:50%) 20 nm |
| | | | Use as ETM | | |
| D-Vac 11 | HTM 220 nm | — | M1:M2:Ir-G (65%:30%:5%) 25 nm | M1 10 nm | E1:ETM2 (50%:50%) 20 nm |
| D-Vac 12 | HTM 220 nm | — | D5:M2:Ir-R (45%:50%:5%) 25 nm | M1 10 nm | E1:ETM2 (50%:50%) 20 nm |
| | | | Use as SEB/SMB | | |
| D-Vac 13 | HTM 190 nm | — | D4::SEB (95%:5%) 20 nm | — | ETM1:ETM2 (50%:50%) 30 nm |
| D-Vac13-Ref | HTM 190 nm | — | SMB-Ref:SEB (95%:5%) 20 nm | — | ETM1:ETM2 (50%:50%) 30 nm |
| D-Vac 14 | HTM 190 nm | — | A39:SEB (95%:5%) 20 nm | — | ETM1:ETM2 (50%:50%) 30 nm |
| D-Vac 15 | HTM 190 nm | — | A42:SEB (95%:5%) 20 nm | — | ETM1:ETM2 (50%:50%) 30 nm |
| D-Vac 16 | HTM 190 nm | — | SMB:A44 (95%:5%) 20 nm | — | ETM1:ETM2 (50%:50%) 30 nm |

TABLE 2

Results for the vacuum-processed OLEDs

| Ex. | EQE (%) 1000 cd/m² | Voltage (V) 1000 cd/m² | CIE x/y 1000 cd/m² | LD50 (h) 1000 cd/m² |
|---|---|---|---|---|
| Use as HTM | | | | |
| D-Vac 1 | 18.3 | 3.5 | 0.34/0.63 | 55000 |
| D-Vac 2 | 19.4 | 3.5 | 0.34/0.64 | — |
| D-Vac 3 | 17.6 | 3.6 | 0.35/0.64 | 70000 |
| D-Vac 4 | 18.1 | 3.7 | 0.35/0.64 | 50000 |
| Use as TMM | | | | |
| D-Vac 5 | 18.8 | 3.6 | 0.35/0.64 | 70000 |
| D-Vac 5-Ref | 18.5 | 3.6 | 0.35/0.65 | 30000 |
| D-Vac 6 | 16.9 | 3.3 | 0.67/0.33 | 85000 |
| D-Vac 7 | 16.5 | 3.2 | 0.67/0.33 | — |
| D-Vac 8 | 16.7 | 3.1 | 0.67/0.33 | — |
| D-Vac 9 | 16.7 | 3.2 | 0.66/0.34 | — |
| D-Vac 10 | 16.3 | 3.3 | 0.67/0.33 | — |
| Use as ETM | | | | |
| D-Vac 11 | 17.0 | 3.3 | 0.35/0.64 | — |
| D-Vac 12 | 16.6 | 3.2 | 0.67/0.33 | — |
| Use as SEB/SMB | | | | |
| D-Vac 13 | 7.2 | 3.9 | 0.15/0.17 | 8000 |
| D-Vac 13-Ref | 7.0 | 4.2 | 0.15/0.17 | 6000 |
| D-Vac 14 | 7.0 | 4.0 | 0.15/0.17 | — |
| D-Vac 15 | 7.4 | 4.2 | 0.15/0.17 | — |
| D-Vac 16 | 5.5 | 3.9 | 0.16/0.24 | — |

2) Solution-Processed Devices:
A: From Soluble Functional Materials

The iridium complexes of the invention may also be processed from solution and lead therein to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/PEDOT (80 nm)/interlayer (80 nm)/emission layer (80 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in the cleanroom, as a buffer layer, an 80 nm layer of PEDOT (PEDOT is a polythiophene derivative (Baytron P VAI 4083sp.) from H. C. Starck, Goslar, which is supplied as an aqueous dispersion) is applied by spin-coating. The required spin rate depends on the degree of dilution and the specific spin-coater geometry (typical value for 80 nm: 4500 rpm). In order to remove residual water from the layer, the substrates are baked on a hotplate at 180° C. for 10 minutes. The interlayer used serves for hole injection; in this case, HIL-012 from Merck is used. The interlayer may alternatively also be replaced by one or more layers which merely have to fulfill the condition of not being leached off again by the subsequent processing step of EML deposition from solution. For production of the emission layer, the emitters of the invention are dissolved together with the matrix materials in toluene. The typical solids content of such solutions is between 16 and 25 g/L when, as here, the layer thickness of 80 nm which is typical of a device is to be achieved by means of spin-coating. The solution-processed devices contain an emission layer composed of (polystyrene):matrix1:matrix2:Ir-G-Sol (25%: 25%:40%:10%). The emission layer is spun on in an inert gas atmosphere, argon in the present case, and baked at 130° C. for 30 min. Lastly, a cathode composed of barium (5 nm) and then aluminum (100 nm) (high-purity metals from Aldrich, particularly barium 99.99% (cat. no. 474711); vapor deposition systems from Lesker or the like, typical vapor deposition pressure $5\times10^{-6}$ mbar) is applied by vapor deposition. It is optionally possible first to apply a hole blocker layer and then an electron transport layer and only then the cathode (e.g. Al or LiF/Al) by vapor deposition under reduced pressure. In order to protect the device from air and air humidity, the device is finally encapsulated and then characterized. The OLED examples cited are yet to be optimized; table 3 summarizes the data obtained.

TABLE 3

Results with materials processed from solution

| Ex. | Matrix1 Matrix2 | EQE (%) 1000 cd/m² | Voltage (V) 1000 cd/m² | CIE x/y 1000 cd/m² |
|---|---|---|---|---|
| Green OLEDs | | | | |
| D-Sol1 | A57 M1 | 18.3 | 5.4 | 0.35/0.63 |
| D-Sol2 | M2 C1 | 18.6 | 5.7 | 0.34/0.64 |

TABLE 4

Structural formulae of the materials used

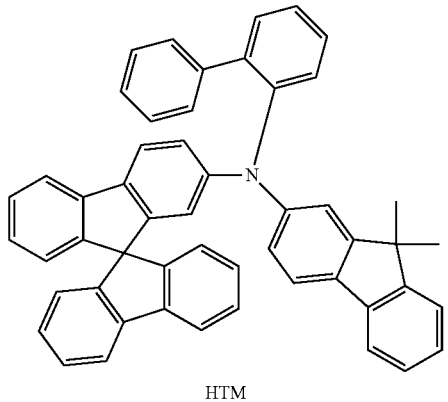

HTM

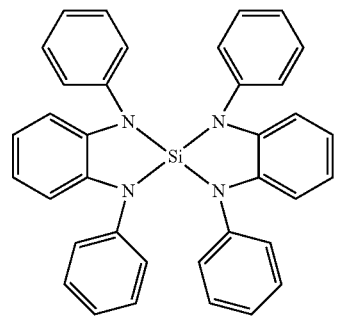

EBM = M10

TABLE 4-continued
Structural formulae of the materials used
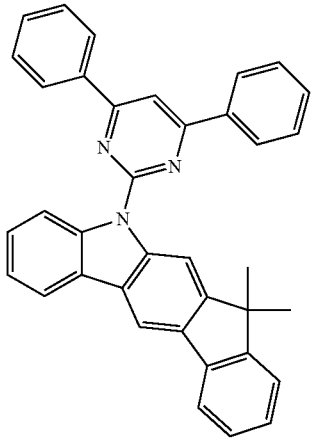
M1 = HBM
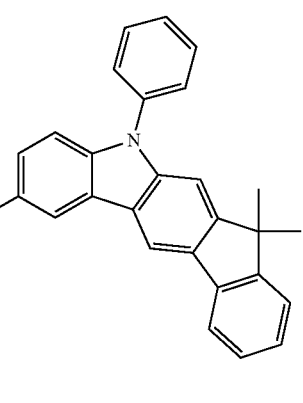
M2
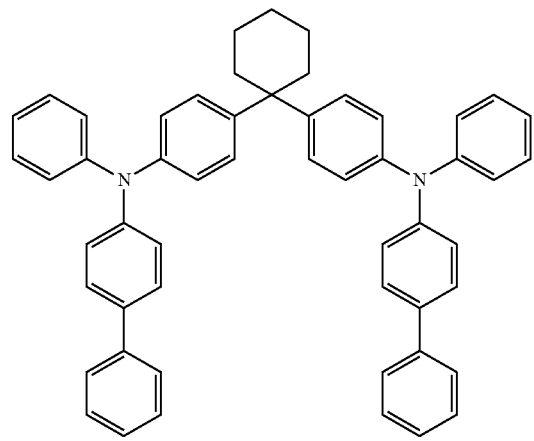
M3
TABLE 4-continued
Structural formulae of the materials used
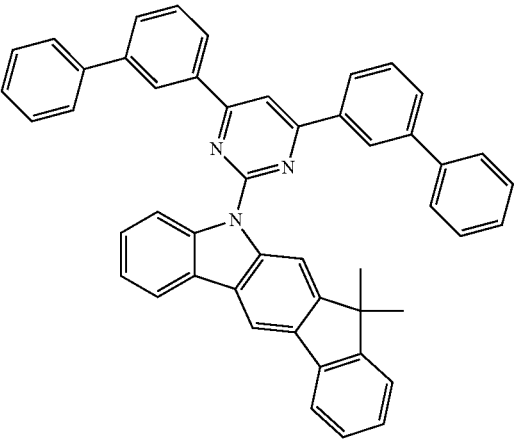
M4
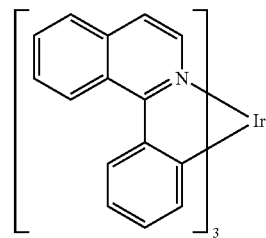
Ir-R
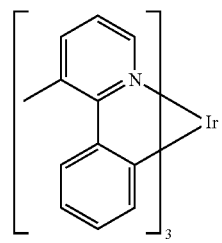
Ir-G
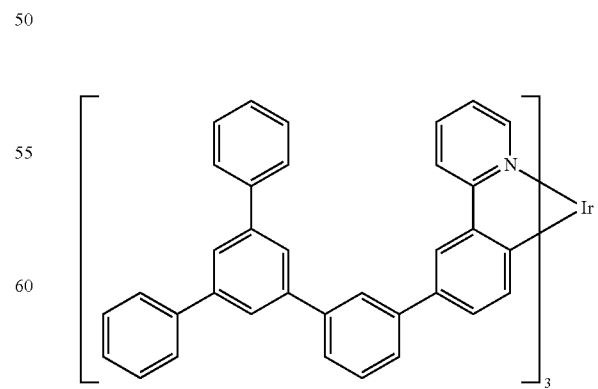
Ir-G-Sol TABLE 4-continued
Structural formulae of the materials used
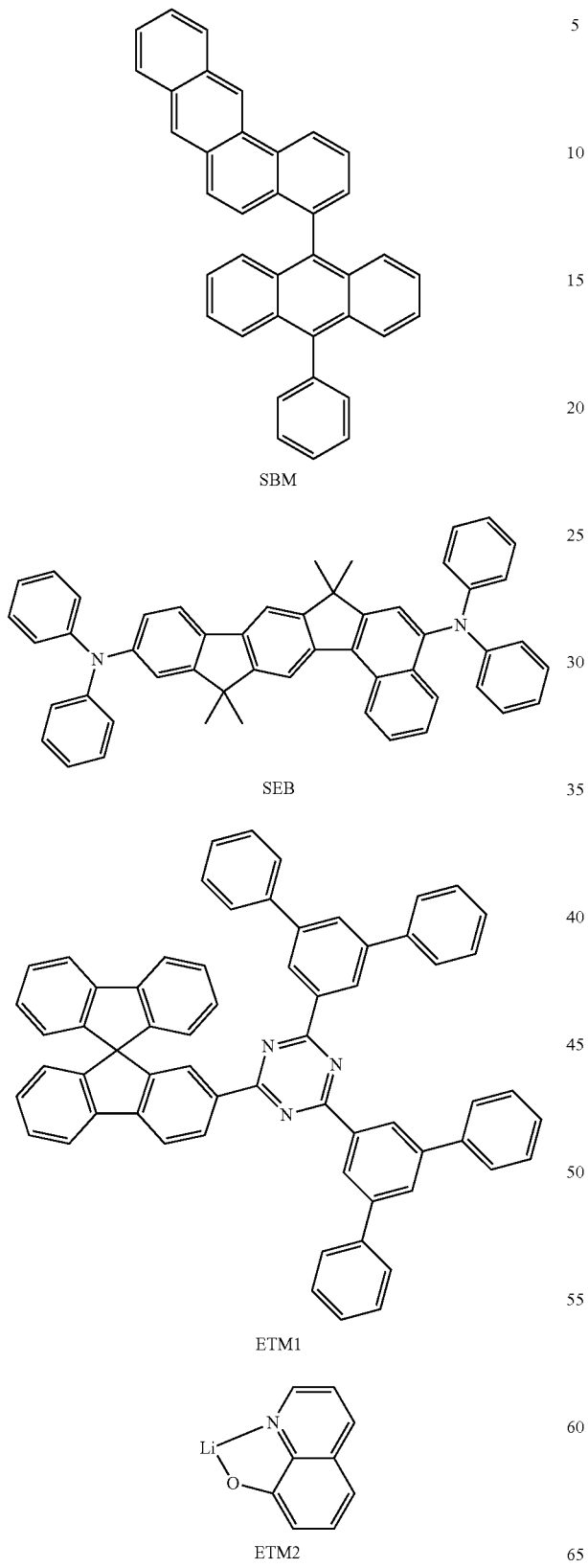
SBM
SEB
ETM1
ETM2
TABLE 4-continued
Structural formulae of the materials used
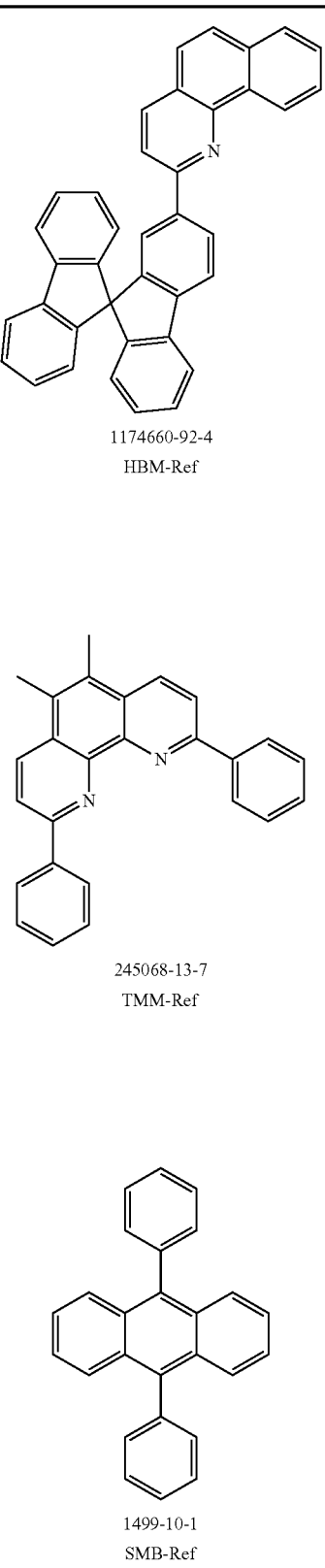
1174660-92-4
HBM-Ref
245068-13-7
TMM-Ref
1499-10-1
SMB-Ref

The invention claimed is:
1. A compound of formulae (Ia) or (IIa):

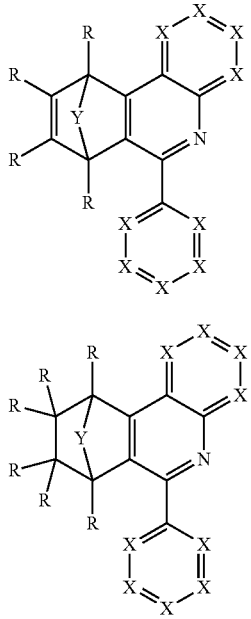

wherein
X is the same or different in each instance and is CR or N;
Y is or phenyl;
R is the same or different in each instance and is H, D, F, Cl, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy, or thioalkoxy group having 1 to 20 carbon atoms or an alkenyl or alkynyl group having 2 to 20 carbon atoms or a branched or cyclic alkyl, alkoxy, or thioalkoxy group having 3 to 20 carbon atoms, each of which is optionally substituted by one or more $R^1$ radicals, wherein one or more hydrogen atoms are optionally replaced by D or F, an aromatic or heteroaromatic ring system which has 5 to 60 aromatic ring atoms and is optionally substituted in by one or more $R^1$ radicals, an aryloxy or heteroaryloxy group which has 5 to 40 aromatic ring atoms and is optionally substituted by one or more $R^1$ radicals, an aralkyl or heteroaralkyl group which has 5 to 40 aromatic ring atoms and is optionally substituted by one or more $R^1$ radicals, or a diarylamino group, diheteroarylamino group, or arylheteroarylamino group which has 10 to 40 aromatic ring atoms and is optionally substituted by one or more $R^1$ radicals; and wherein two adjacent R radicals together optionally define a mono- or polycyclic, aliphatic, aromatic, or heteroaromatic ring system;
$R^1$ is the same or different in each instance and is H, D, F, Cl, Br, I, $N(R^2)_2$, CN $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 20 carbon atoms or an alkenyl or alkynyl group having 2 to 20 carbon atoms or a branched or cyclic alkyl, alkoxy, or thioalkoxy group having 3 to 20 carbon atoms, each of which is optionally substituted by one or more $R^2$ radicals, wherein one or more nonadjacent $CH_2$ groups are optionally replaced by $R^2C=CR^2$, $C\equiv C$, $Si(R^2)_2$, $C=O$, $NR^2$, O, S, or $CONR^2$ and wherein one or more hydrogen atoms are optionally replaced by D, F, Cl, Br, I, CN, or $NO_2$, an aromatic or heteroaromatic ring system which has 5 to 60 aromatic ring atoms and is optionally substituted by one or more $R^2$ radicals, an aryloxy or heteroaryloxy group which has 5 to 40 aromatic ring atoms and is optionally substituted by one or more $R^2$ radicals, an aralkyl or heteroaralkyl group which has 5 to 40 aromatic ring atoms and is optionally substituted by one or more $R^2$ radicals, or a diarylamino group, diheteroarylamino group, or arylheteroarylamino group which has 10 to 40 aromatic ring atoms and is optionally substituted by one or more $R^2$ radicals; and wherein two or more adjacent $R^1$ radicals together, or $R^1$ together with R, optionally define a mono- or polycyclic, aliphatic, aromatic, or heteroaromatic ring system;
$R^2$ is the same or different in each instance and is H, D, F, or an aliphatic, aromatic, and/or heteroaromatic hydrocarbyl radical having 1 to 20 carbon atoms, wherein one or more hydrogen atoms are optionally replaced by F; and wherein two or more $R^2$ radicals together optionally define a mono- or polycyclic aliphatic ring system.

2. The compound of claim 1, wherein the compound comprises a structure of formulae (Ia1), (Ia2), (IIa1), or (IIa2):

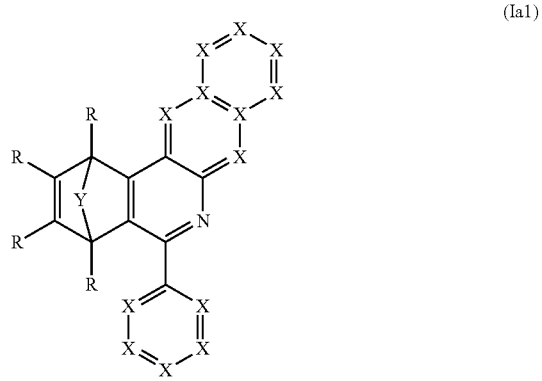

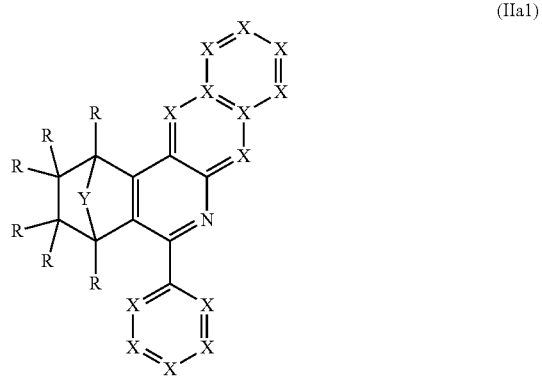

-continued
(Ia2)
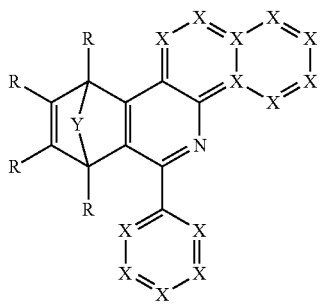
(IIa2)
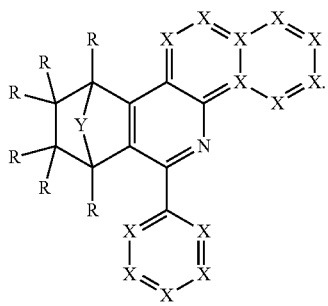
3. The compound of claim 1, wherein the compound comprises a structure of formulae (Ia3) or (Ia4):
(Ia3)
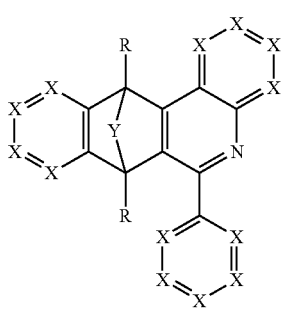
(Ia4)
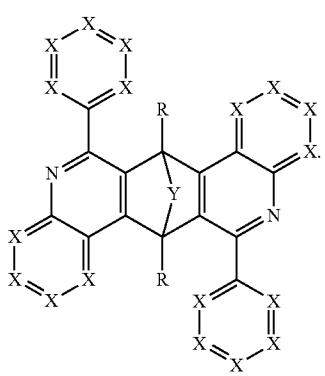
4. The compound of claim 1, wherein the compound comprises structures of formula CyE-(CyF)$_n$, wherein:
n is 2 or 3
CyE is a structural element selected from the group consisting of formulae (CyE-1) through (CyE-27):
(CyE-1)
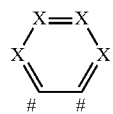
(CyE-2)
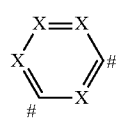
(CyE-3)
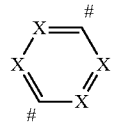
(CyE-4)
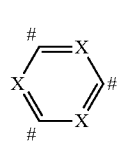
(CyE-5)
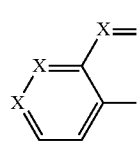
(CyE-6)
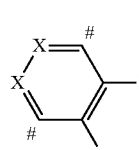
(CyE-7)
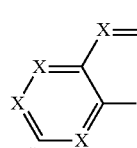
(CyE-8)
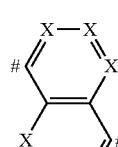
(CyE-9)
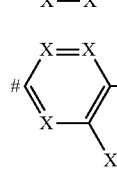
(CyE-10)

(CyE-11)
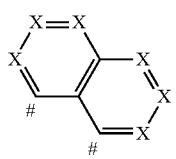
(CyE-12)
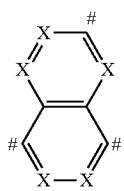
(CyE-13)
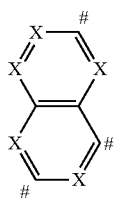
(CyE-14)
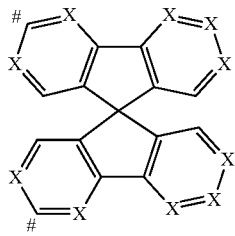
(CyE-15)
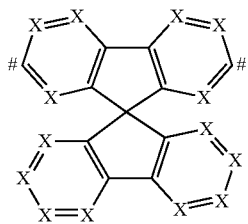
(CyE-16)
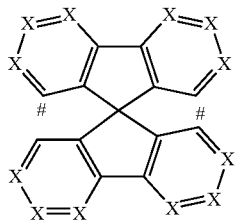
(CyE-17)
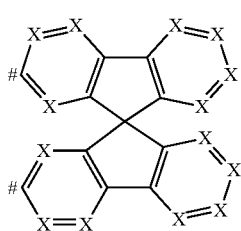
(CyE-18)
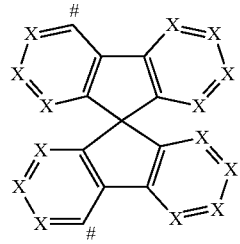
(CyE-19)
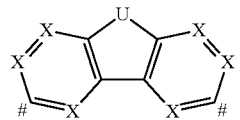
(CyE-20)
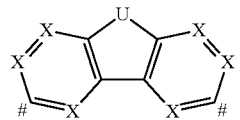
(CyE-21)
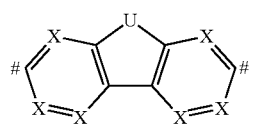
(CyE-22)
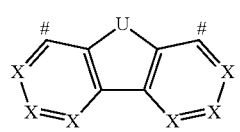
(CyE-23)
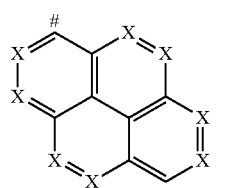
(CyE-24)
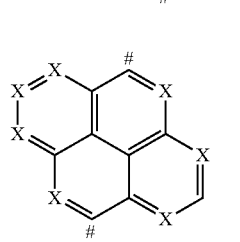
(CyE-25)
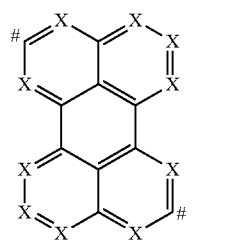

-continued (CyE-26)
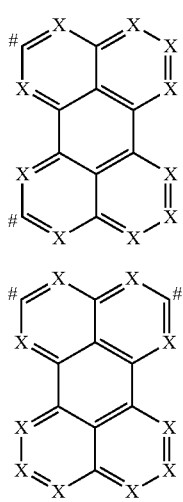
(CyE-27)

CyF is at least one structural element selected from the group consisting of formulae (CyF-3) and (CyF-4):

(CyF-3)
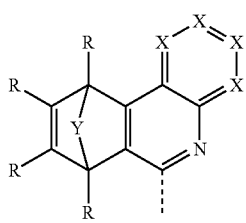

(CyF-4)
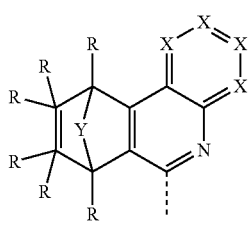

wherein
U is selected from the group consisting of O, S, C(R)$_2$, N(R), B(R), Si(R)$_2$, C=O, S=O, SO$_2$, P(R) and P(=O)R; and the dotted line in formulae (CyF-3) and (CyF-4) denotes the bond to the CyE group, and CyF group bonds to CyE in each case at the position denoted by #.

5. The compound of claim 1, wherein the compounds have structures of formula CyG(CyH)$_n$, wherein CyG and CyH together in each case defined a ring and:
n is 2 or 3
CyG is a structural element selected from the group consisting of formulae (CyG-1) through (CyG-17):

(CyG-1)
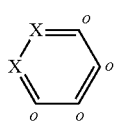

-continued (CyG-2)
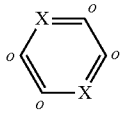

(CyG-3)

(CyG-4)
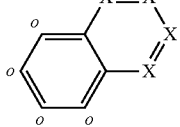

(CyG-5)
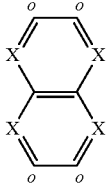

(CyG-6)
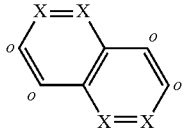

(CyG-7)
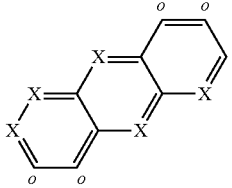

(CyG-8)
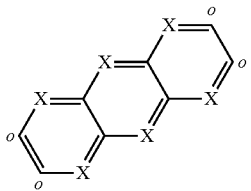

(CyG-9)
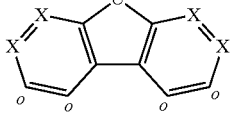

(CyG-10)
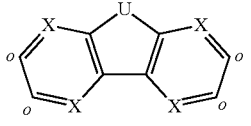

-continued (CyG-11)
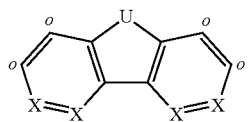

(CyG-12)
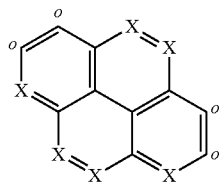

(CyG-13)
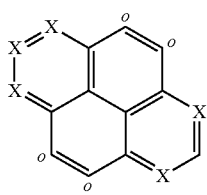

(CyG-14)
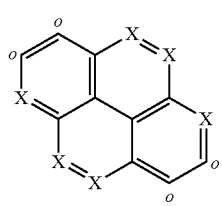

(CyG-15)
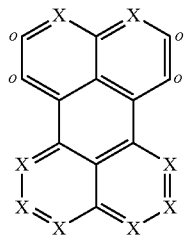

(CyG-16)
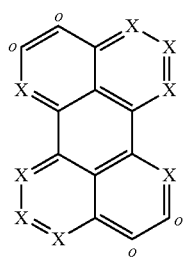

(CyG-17)
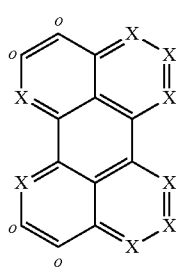

and
CyH is at least one structural element selected from the group consisting of formulae (CyH-1) (CyH-2)

(CyH-1)
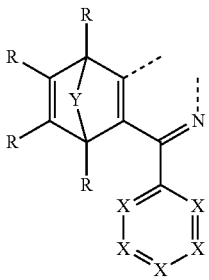

(CyH-2)
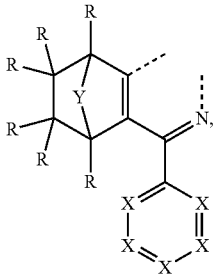

wherein
U is selected from the group consisting of O, S, $C(R)_2$, N(R), B(R), $Si(R)_2$, C=O, S=O, $SO_2$, P(R), and P(=O)R; and
the dotted line in formulae CyH-1 and CyH-2 denotes the bond to CyG, and CyH bonds to CyG in each case at the positions denoted by o so as to define a ring.

6. The compound of claim 1, wherein the compound is in the form of an enantiomer mixture.

7. The compound of claim 1, wherein the definitions for X are selected such that the ratio of CR to N is greater than or equal to 3.

8. The compound of claim 1, wherein the compound has a glass transition temperature of at least 110° C.

9. The compound of claim 1, wherein the compound has a molecular weight of not more than 5000 g/mol.

10. A composition comprising at least one compound of claim 1 and at least one further organic functional material selected from the group consisting of fluorescent emitters, phosphorescent emitters, host materials, matrix materials, electron transport materials, electron injection materials, hole conductor materials, hole injection materials, electron blocker materials, and hole blocker materials.

11. A formulation comprising at least one compound of claim 1 and at least one solvent.

12. An electronic device comprising at least one compound of claim 1.

13. The electronic device of claim 12, wherein the electronic device is selected from the group consisting of organic electroluminescent devices.

14. The compound of claim 6, wherein the compound is in the form of a diastereomer mixture.

15. The electronic device of claim 13, wherein the electronic device is an organic electroluminescent device selected from the group consisting of organic laser diodes, organic light-emitting transistors, organic light-emitting diodes, organic light-emitting electrochemical cells, organic integrated circuits, organic field-effect transistors, organic thin-film transistors, organic solar cells, organic optical detectors, organic photoreceptors, and organic field quench devices.

16. The compound of claim 1, wherein the compound is selected from the group consisting of compounds 1-13, 14a, 14b, 16, 17, 20, 26-36, 38-42, 44-46, 48-84, A32, A39, A42, A44, B3, D4, A57, A58, and A59:
1
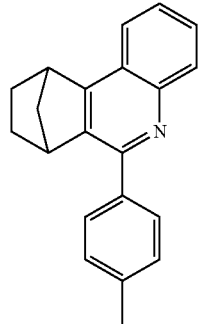
2
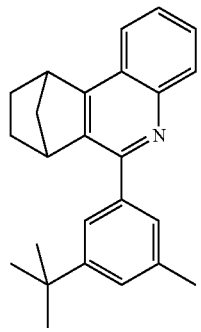
3
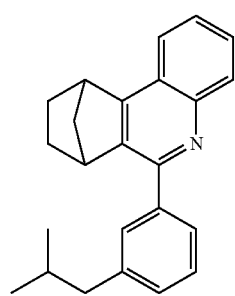
4
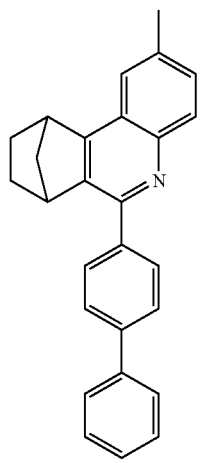
5
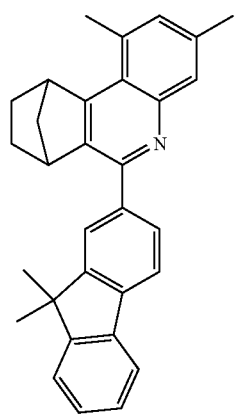
6
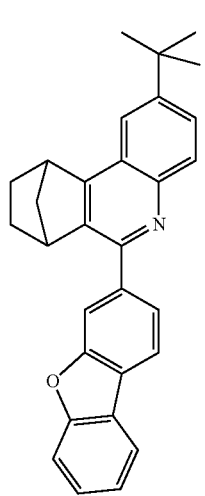

-continued
7
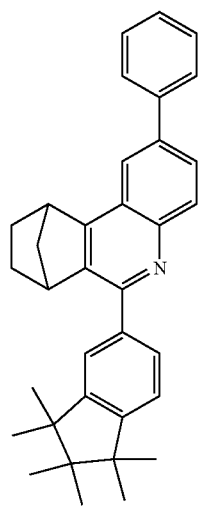
8
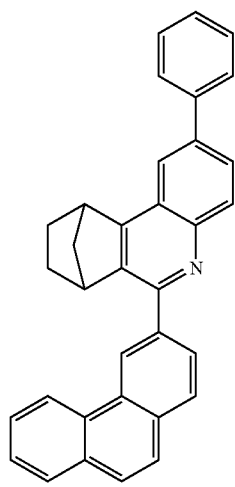
9
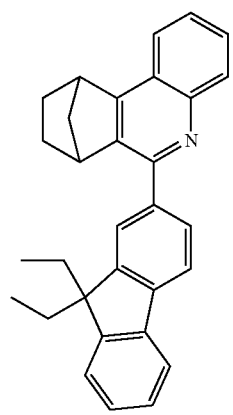
10
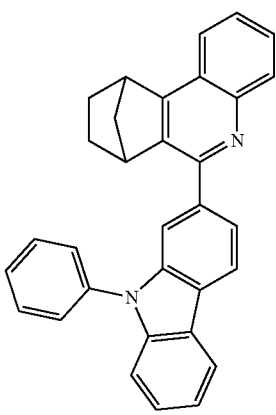
11
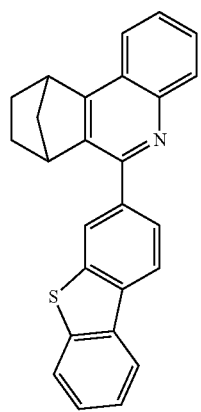
12
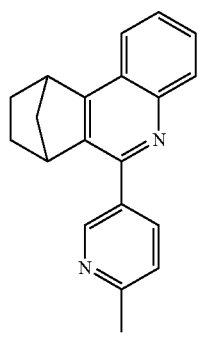

-continued
13
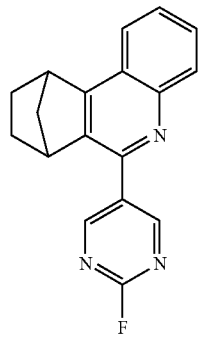
14a
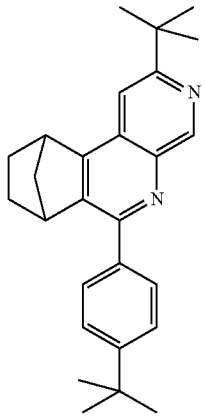
14b
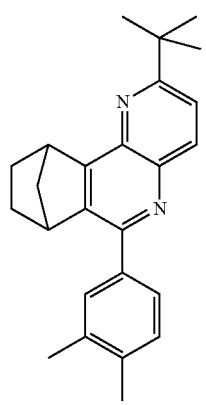
16
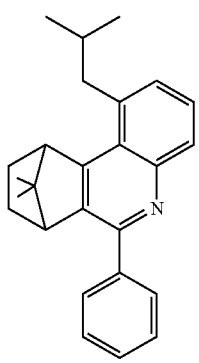
17
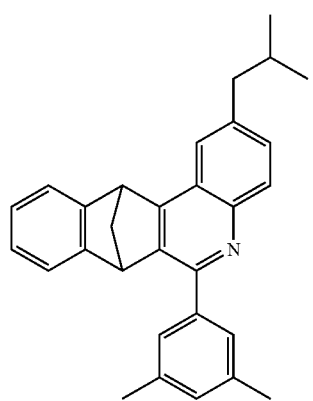
20
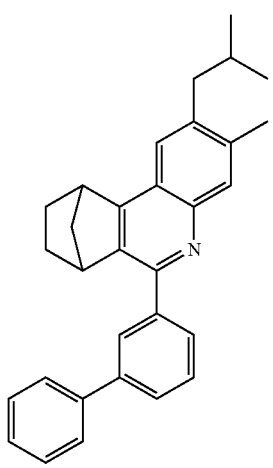

-continued
26
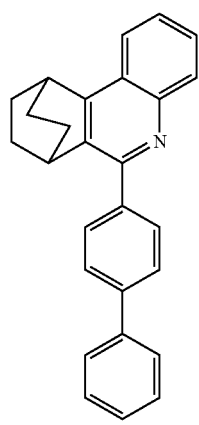
27
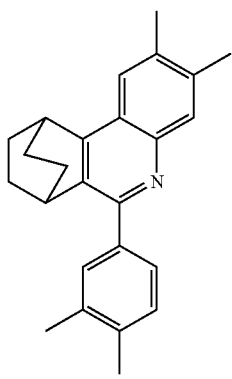
28
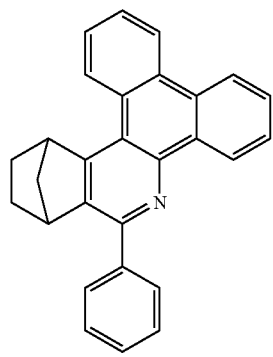
29
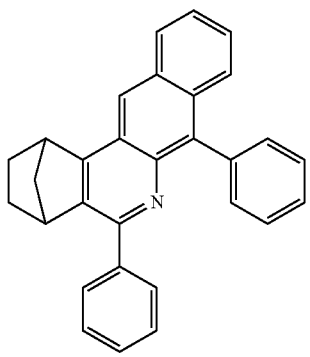
30
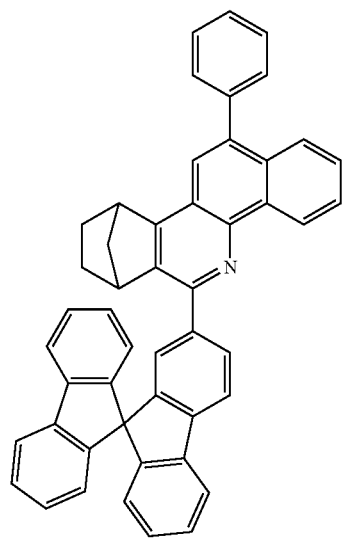
31
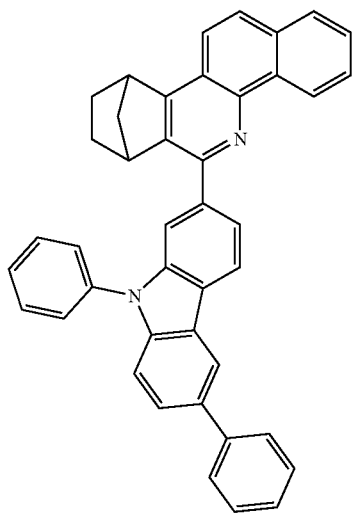

-continued
31
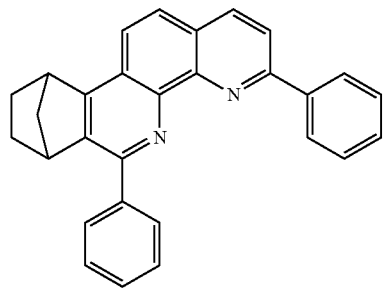
32
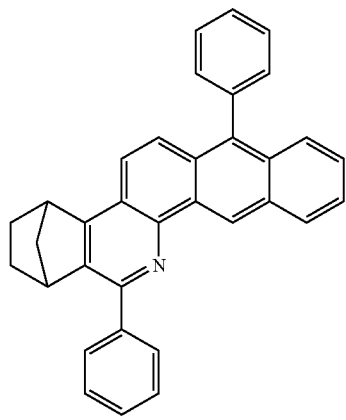
33
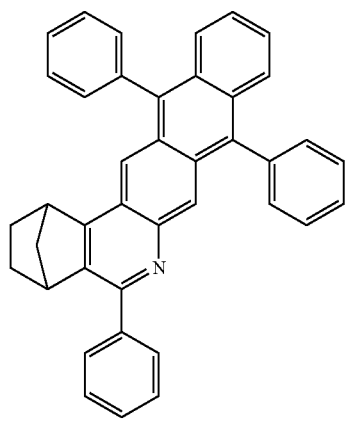
34
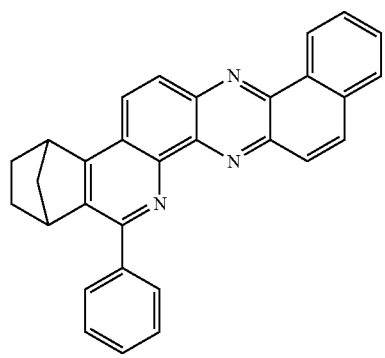
35
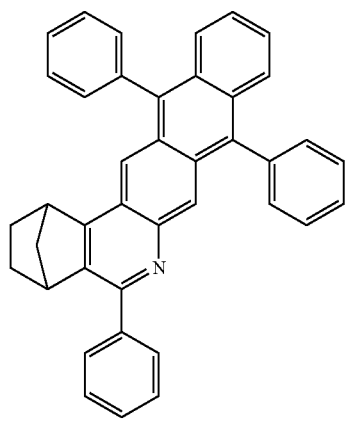
36
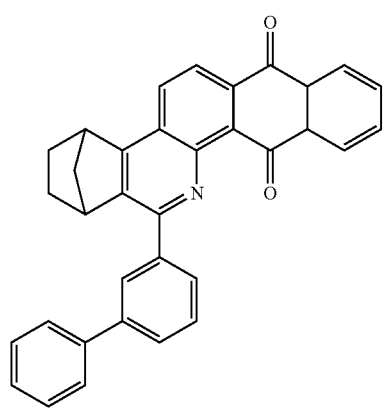
38
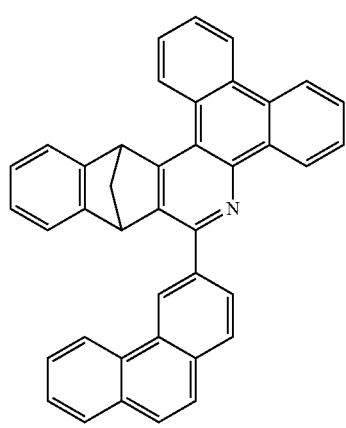

-continued
39
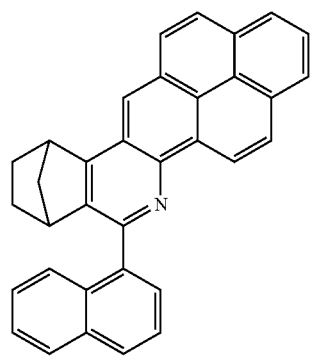
40
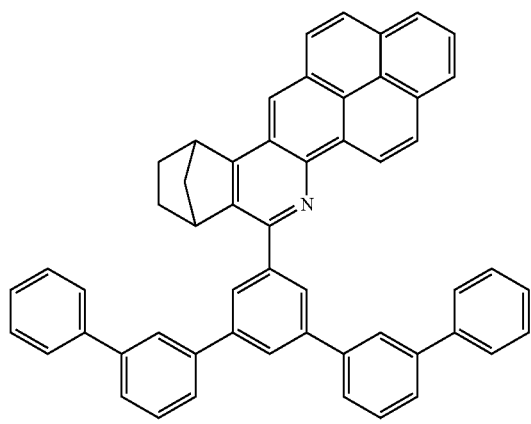
41
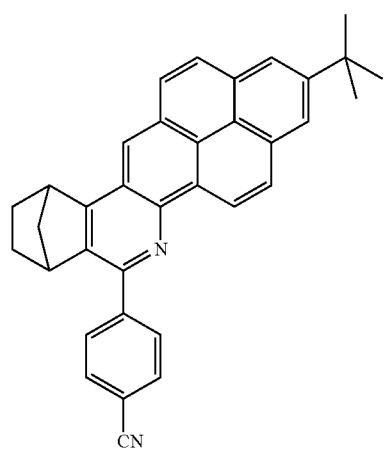
42
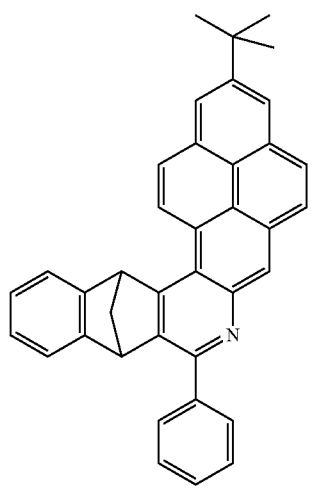
44
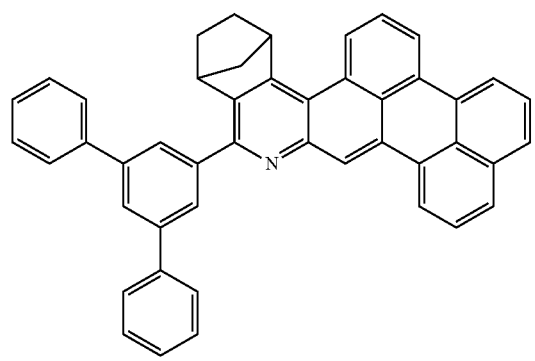
45
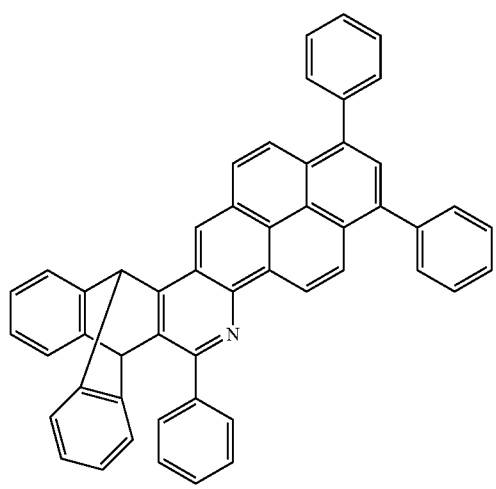

-continued
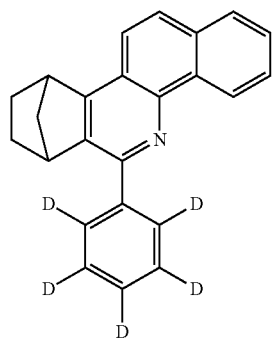
46
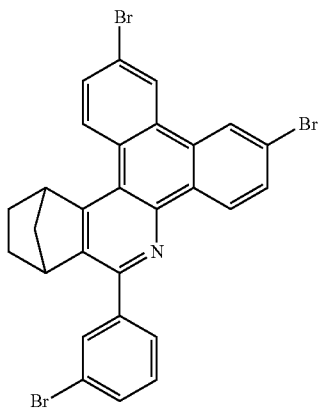
48
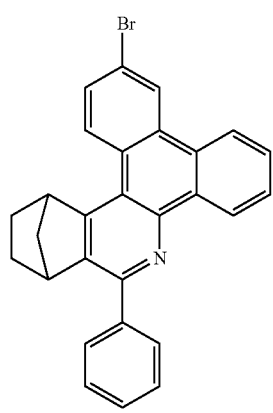
49
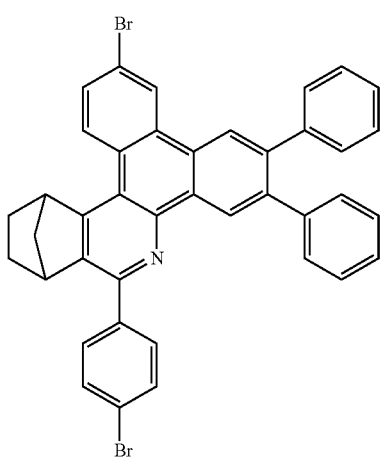
50
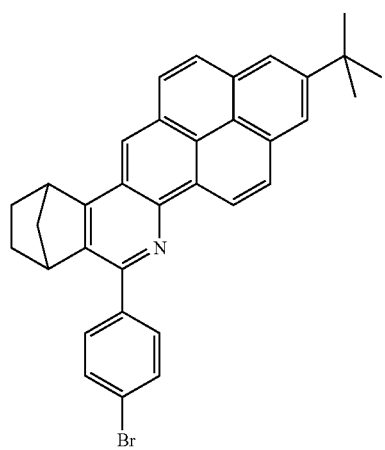
51
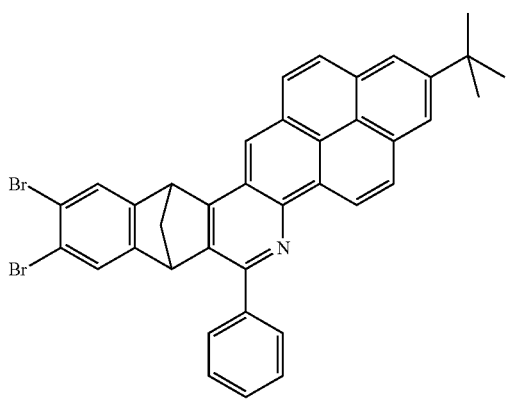
52

-continued
53
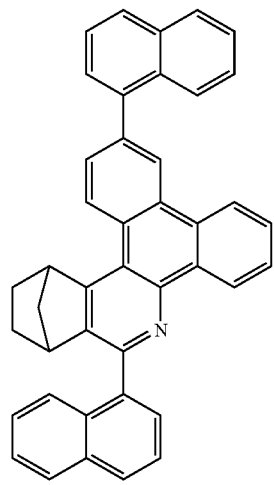
54
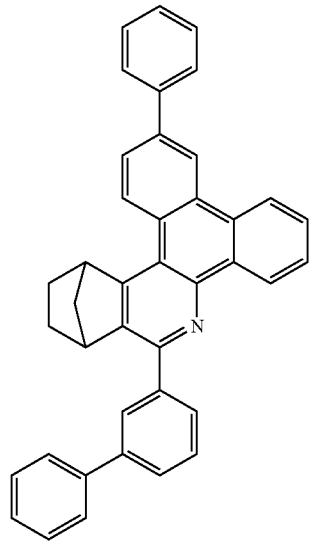
55
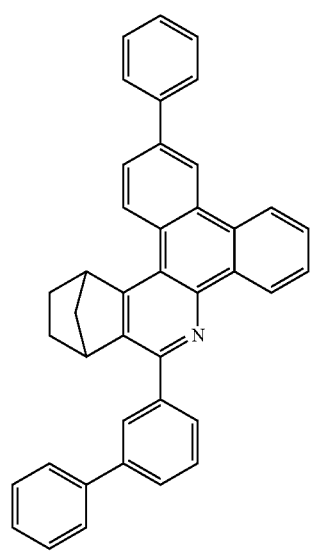
56
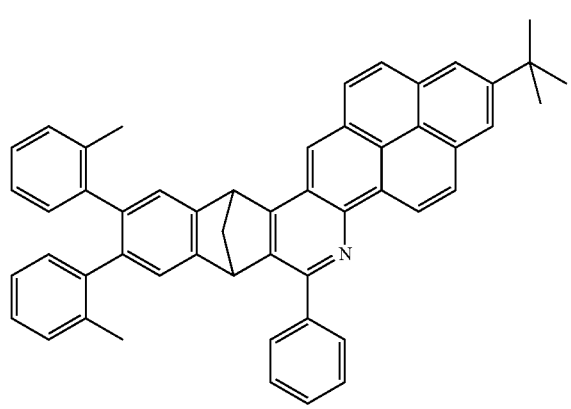

-continued
57
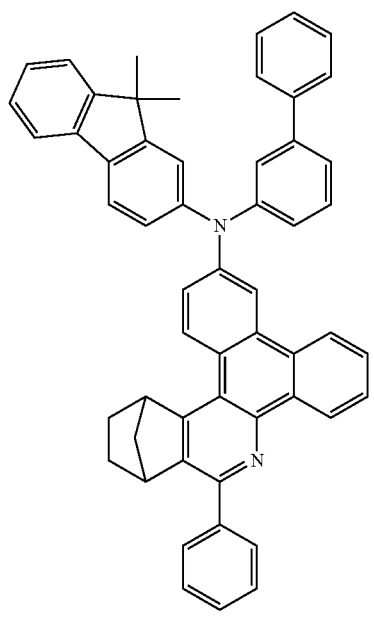
58
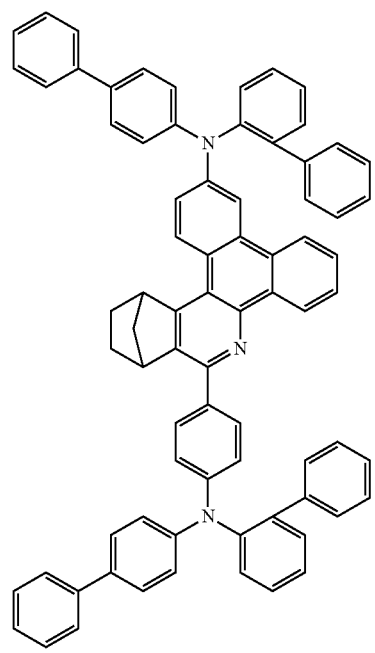
59
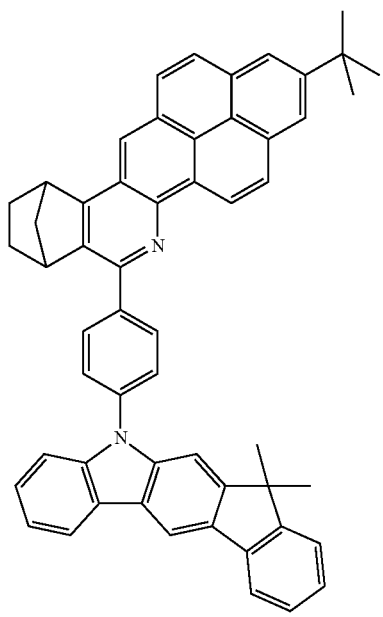
60
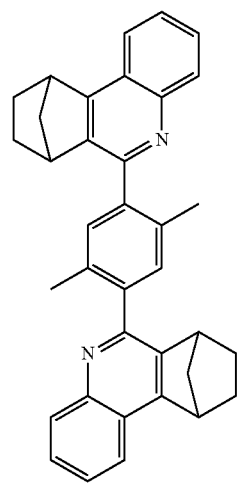

-continued
61
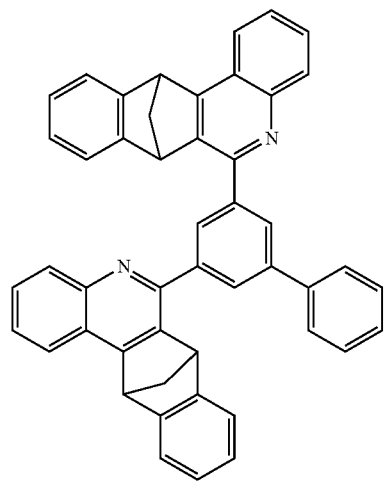
62
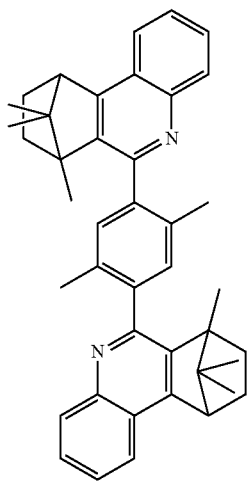
63
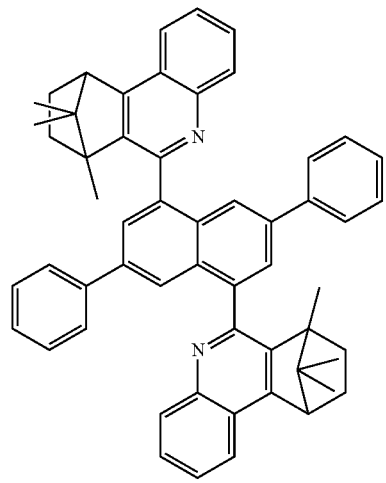
64
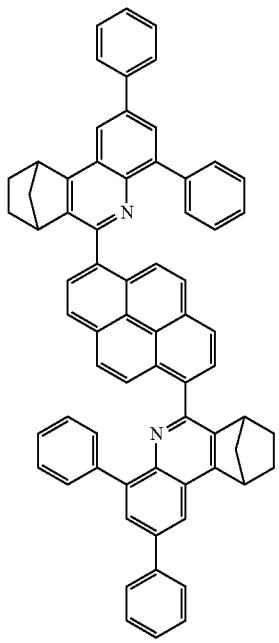

-continued
65
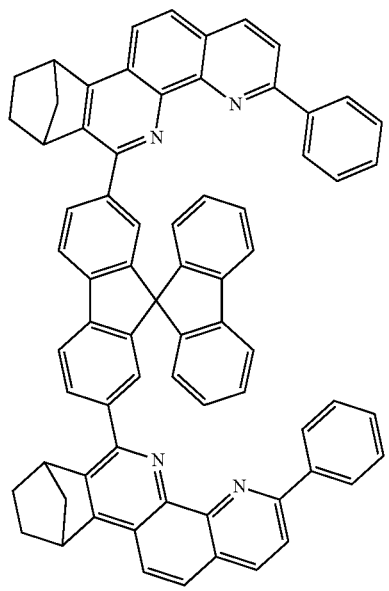
66
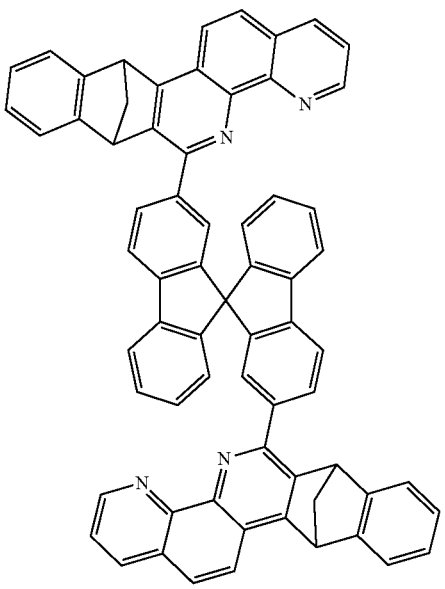
67
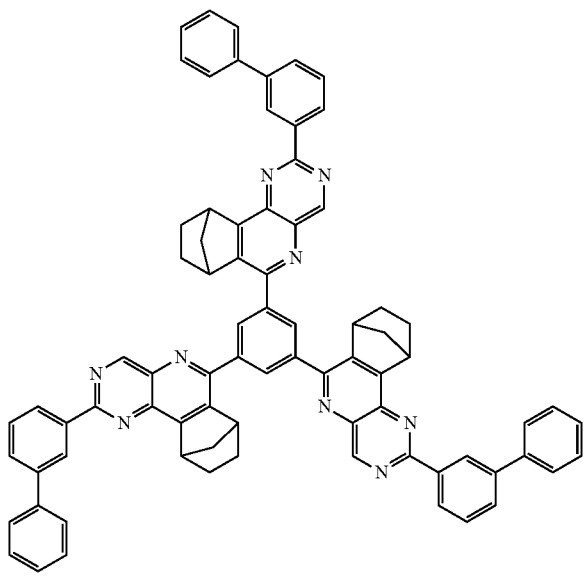
68
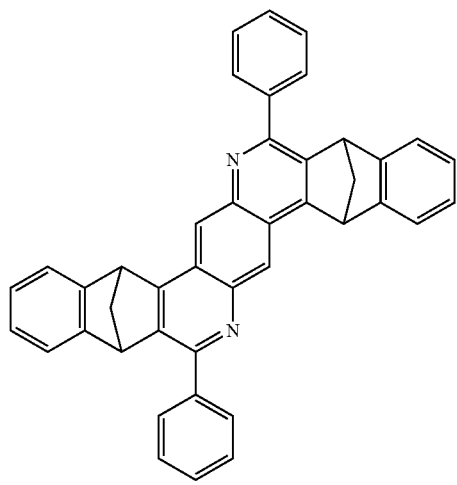
69
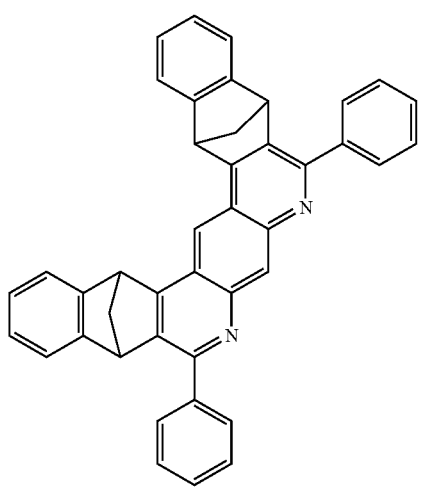
70
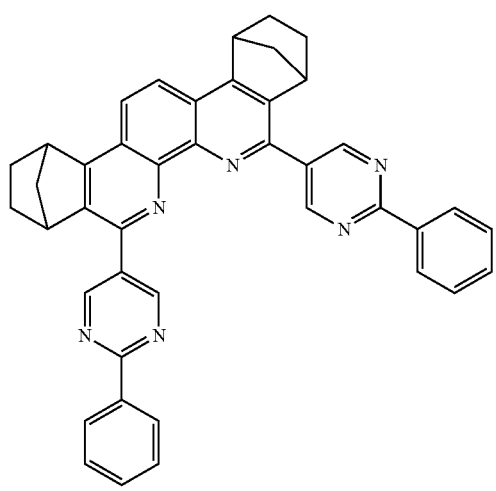

-continued
71
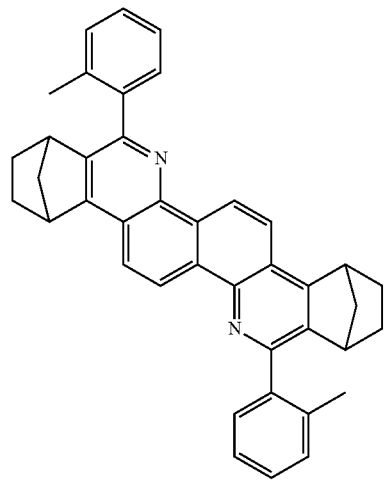
72
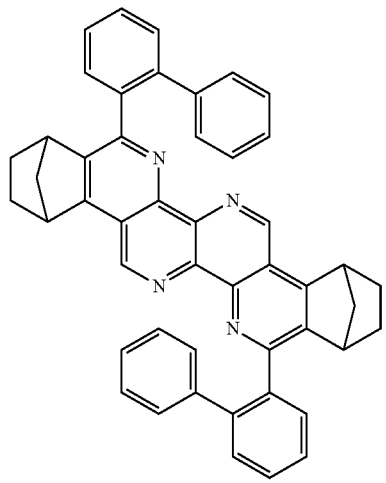
73
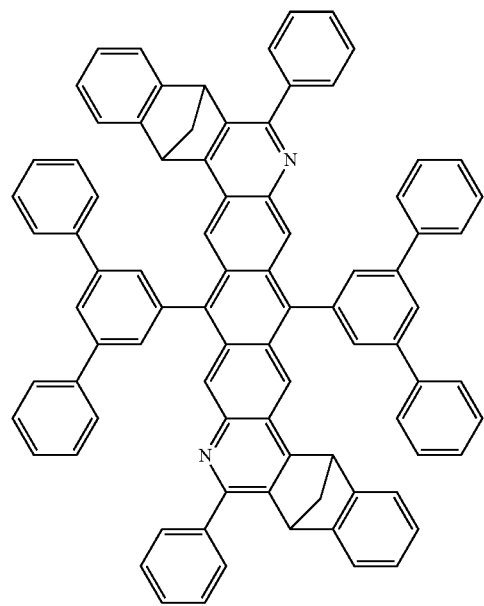
74
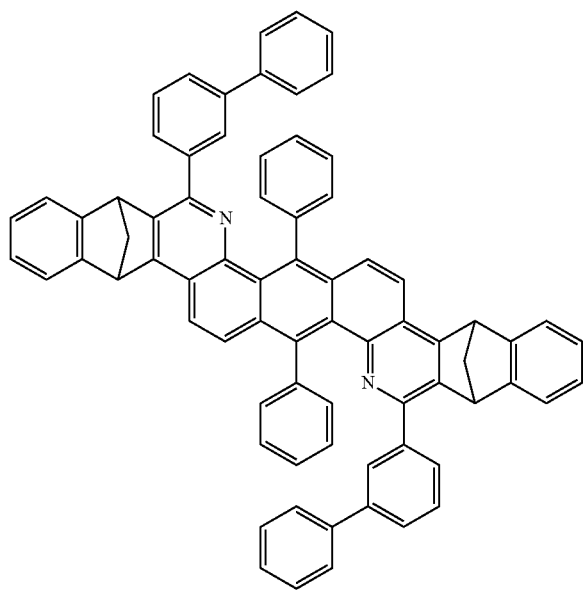

-continued
75
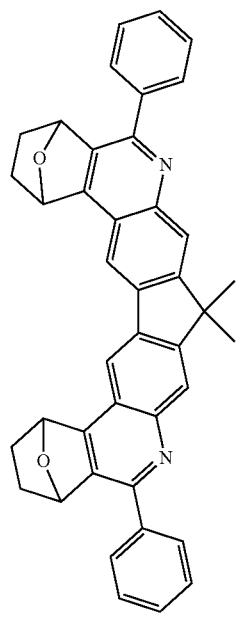
76
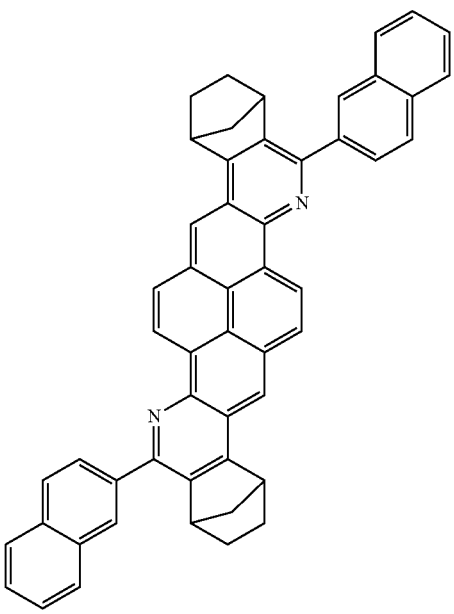
77
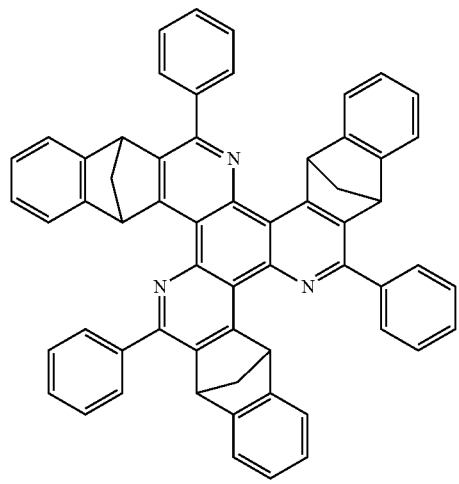
78
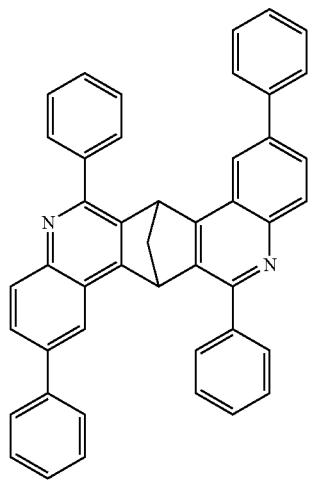
79
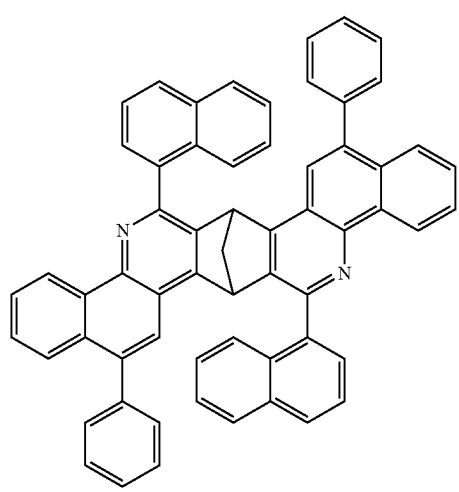
80
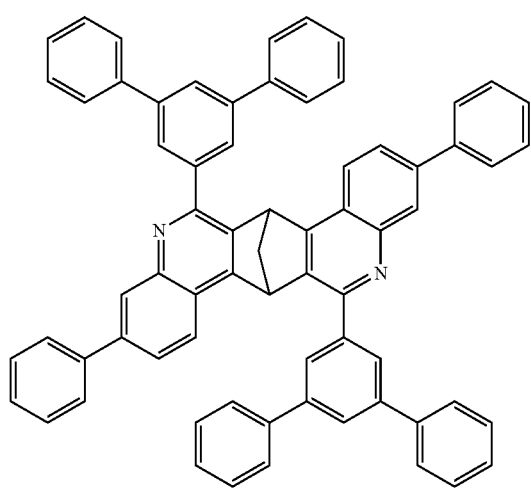

-continued
81
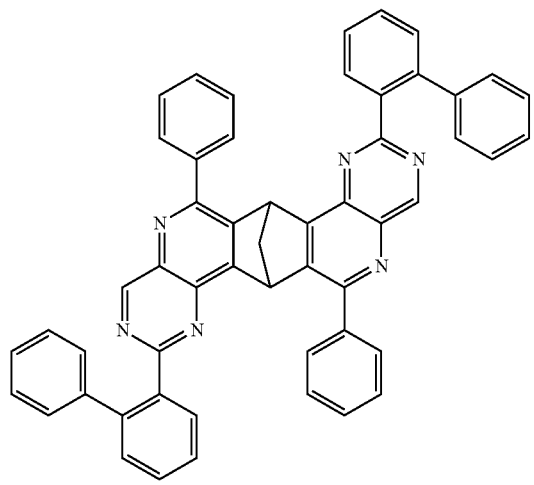
82
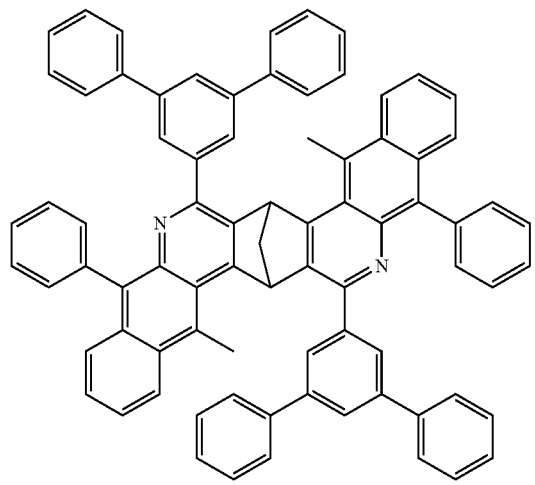
83
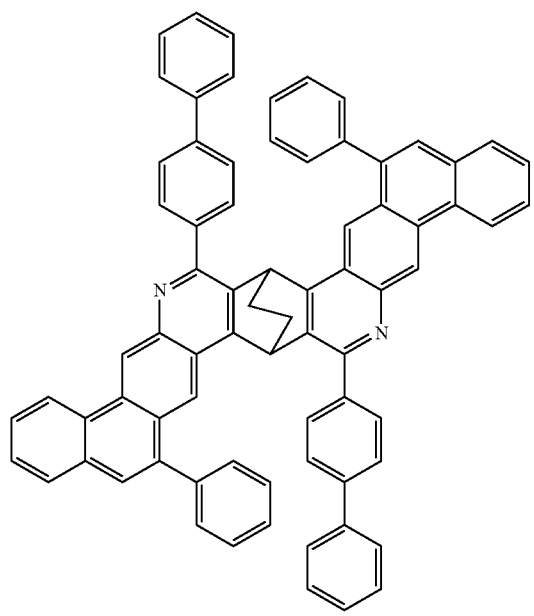
84
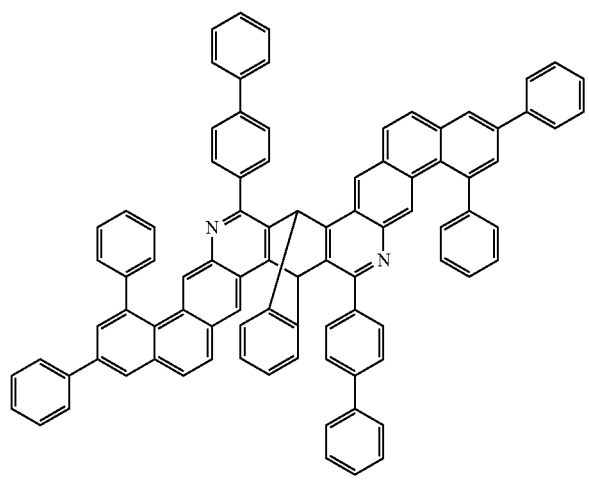
A32
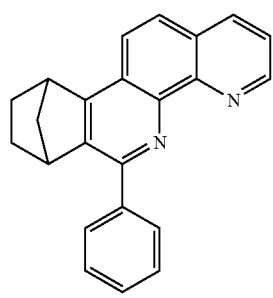
A39
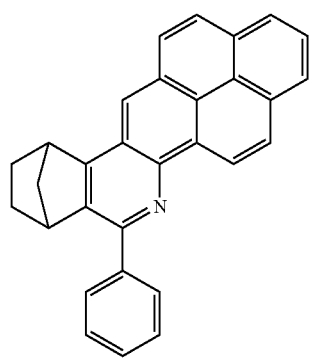

-continued
A42
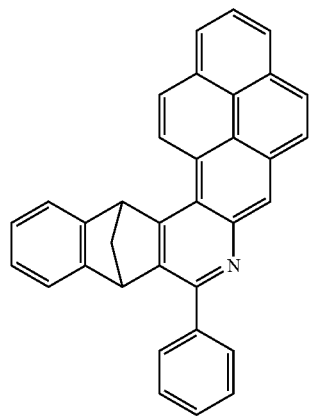
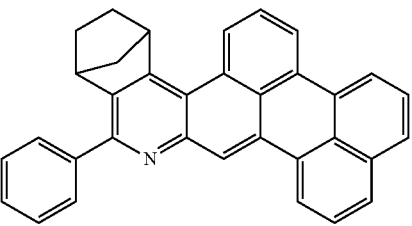
A44
B3
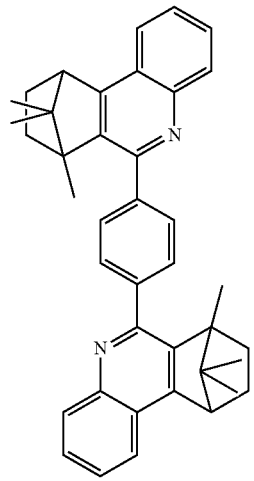
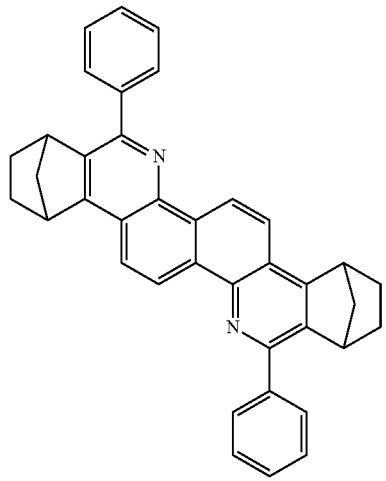
D4
A57
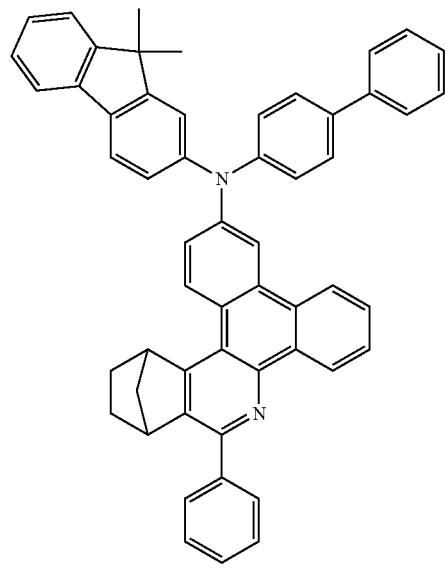
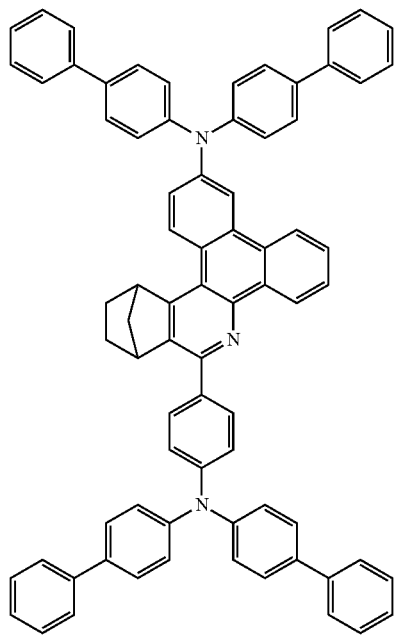 [SMILES: c1ccc(-c2ccc(N(c3ccc(-c4ccccc4)cc3)c3ccc(-c4nc5c6ccccc6c6cc(N(c7ccc(-c8ccccc8)cc7)c7ccc(-c8ccccc8)cc7)ccc6c5c5c4C4CCC5C4)cc3)cc2)cc1]
A58

-continued
A59
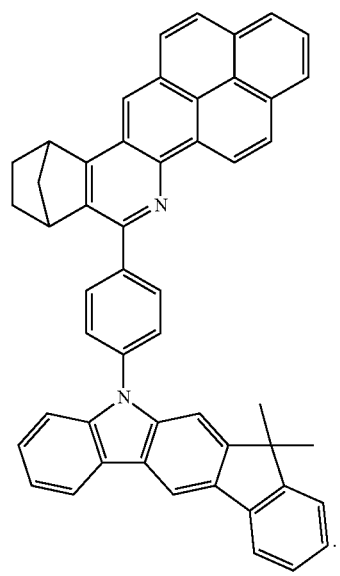
* * * * *